(12) United States Patent
Cardinale et al.

(10) Patent No.: US 9,119,629 B2
(45) Date of Patent: *Sep. 1, 2015

(54) APPLICATOR INSTRUMENTS FOR DISPENSING SURGICAL FASTENERS DURING OPEN REPAIR PROCEDURES

(71) Applicant: Ethicon, Inc., Somerville, NJ (US)

(72) Inventors: Michael Cardinale, Morristown, NJ (US); Doug Souls, Andover, NJ (US); Simon Cohn, Lebanon, NJ (US); Jonathan B. Gabel, Randolph, NJ (US); Matthew Daniel, Ann Arbor, MI (US); Danial Paul Ferreira, Milford, CT (US)

(73) Assignee: Ethicon, Inc., Somerville, NJ (US)

( * ) Notice: Subject to any disclaimer, the term of this patent is extended or adjusted under 35 U.S.C. 154(b) by 237 days.

This patent is subject to a terminal disclaimer.

(21) Appl. No.: 13/906,596

(22) Filed: May 31, 2013

(65) Prior Publication Data

US 2013/0304092 A1    Nov. 14, 2013

Related U.S. Application Data

(63) Continuation of application No. 13/470,022, filed on May 11, 2012, now Pat. No. 8,518,055.

(51) Int. Cl.
| | | |
|---|---|---|
| *A61B 17/10* | (2006.01) | |
| *A61B 17/128* | (2006.01) | |
| *A61B 17/068* | (2006.01) | |
| *A61B 17/064* | (2006.01) | |
| *A61B 19/00* | (2006.01) | |

(52) U.S. Cl.
CPC ......... *A61B 17/1285* (2013.01); *A61B 17/0682* (2013.01); *A61B 17/064* (2013.01); *A61B 2019/481* (2013.01); *A61B 2019/4836* (2013.01)

(58) Field of Classification Search
CPC ............. A61B 17/0682; A61B 17/064; A61B 17/1285; A61B 2019/4836; A61B 17/068; A61B 17/07207
See application file for complete search history.

(56) References Cited

U.S. PATENT DOCUMENTS

| | | |
|---|---|---|
| 3,740,994 A | 6/1973 | DeCarlo, Jr. |
| 4,196,836 A | 4/1980 | Becht |
| 4,325,376 A | 4/1982 | Klieman et al. |
| 4,471,780 A | 9/1984 | Menges et al. |
| 4,478,220 A | 10/1984 | DiGiovanni et al. |
| 4,921,326 A | 5/1990 | Wild et al. |
| 5,104,394 A | 4/1992 | Knoepfler |
| 5,174,487 A | 12/1992 | Rothfuss et al. |
| 5,203,864 A | 4/1993 | Phillips |
| 5,290,297 A | 3/1994 | Phillips |

(Continued)

*Primary Examiner* — Katherine M Shi
(74) *Attorney, Agent, or Firm* — Doherty IP Law Group LLC

(57) ABSTRACT

An applicator instrument for dispensing surgical fasteners includes a housing, a firing system disposed in the housing and being moveable in distal and proximal directions along a first axis, and an elongated shaft extending from the housing, the elongated shaft having a proximal section and a distal section that is oriented at an angle relative to the proximal section. A plurality of surgical fasteners are disposed in the elongated shaft. The applicator instrument has a handle that extends upwardly from the housing along a second axis that defines an acute angle with the first axis. A trigger is mounted on the handle, and a linkage couples the trigger with the handle and the firing system. When the trigger is squeezed, the linkage guides the trigger along a linear path of movement relative to the handle.

18 Claims, 36 Drawing Sheets

(56) References Cited

U.S. PATENT DOCUMENTS

| | | | |
|---|---|---|---|
| 5,395,381 | A | 3/1995 | Green et al. |
| 5,470,010 | A | 11/1995 | Rothfuss et al. |
| 5,484,095 | A | 1/1996 | Green et al. |
| 5,507,797 | A | 4/1996 | Suzuki et al. |
| 5,582,616 | A | 12/1996 | Bolduc et al. |
| 5,601,573 | A | 2/1997 | Fogelberg et al. |
| 5,607,436 | A | 3/1997 | Pratt et al. |
| 5,624,453 | A | 4/1997 | Ahmed |
| 5,626,587 | A | 5/1997 | Bishop et al. |
| 5,676,674 | A | 10/1997 | Bolanos et al. |
| 5,810,882 | A | 9/1998 | Bolduc et al. |
| 5,830,221 | A | 11/1998 | Stein et al. |
| 5,833,700 | A | 11/1998 | Fogelberg et al. |
| 5,921,997 | A | 7/1999 | Fogelberg et al. |
| 6,066,144 | A * | 5/2000 | Wolf et al. ............ 606/139 |
| 6,193,653 | B1 * | 2/2001 | Evans et al. ............ 600/210 |
| 6,221,007 | B1 | 4/2001 | Green |
| 6,258,105 | B1 | 7/2001 | Hart et al. |
| 6,334,446 | B1 | 1/2002 | Beyar |
| 6,425,900 | B1 | 7/2002 | Knodel et al. |
| 6,779,701 | B2 | 8/2004 | Bailly et al. |
| 7,172,605 | B2 | 2/2007 | Berreklouw |
| 7,442,167 | B2 | 10/2008 | Dunki-Jacobs et al. |
| 7,455,208 | B2 | 11/2008 | Wales et al. |
| 7,648,514 | B1 | 1/2010 | Nakao |
| 7,666,193 | B2 | 2/2010 | Starksen et al. |
| 7,766,207 | B2 | 8/2010 | Mather et al. |
| 7,886,953 | B2 | 2/2011 | Schwemberger et al. |
| 8,518,055 | B1 | 8/2013 | Cardinale et al. |
| 2002/0050277 | A1 | 5/2002 | Beyar |
| 2002/0068947 | A1 | 6/2002 | Kuhns et al. |
| 2002/0095181 | A1 | 7/2002 | Beyar |
| 2002/0183762 | A1 | 12/2002 | Anderson et al. |
| 2005/0139629 | A1 | 6/2005 | Schwemberger et al. |
| 2005/0234297 | A1 | 10/2005 | Devierre et al. |
| 2005/0261555 | A1 | 11/2005 | Guzman et al. |
| 2007/0043384 | A1 | 2/2007 | Ortiz et al. |
| 2007/0191868 | A1 | 8/2007 | Theroux et al. |
| 2008/0214895 | A1 | 9/2008 | Campos |
| 2009/0299382 | A1 | 12/2009 | Zergiebel |
| 2010/0048988 | A1 | 2/2010 | Pastorelli et al. |
| 2010/0057102 | A1 | 3/2010 | Sorrentino et al. |
| 2010/0234687 | A1 | 9/2010 | Azarbarzin et al. |
| 2010/0292710 | A1 | 11/2010 | Daniel et al. |
| 2010/0292712 | A1 | 11/2010 | Nering et al. |
| 2010/0292713 | A1 | 11/2010 | Cohn et al. |
| 2010/0292715 | A1 | 11/2010 | Nering et al. |
| 2010/0327042 | A1 | 12/2010 | Amid et al. |
| 2011/0079627 | A1 * | 4/2011 | Cardinale et al. .......... 227/176.1 |
| 2012/0149982 | A1 | 6/2012 | Fonger et al. |
| 2012/0175401 | A1 | 7/2012 | Bachman |
| 2013/0245681 | A1 | 9/2013 | Straehnz et al. |
| 2013/0267970 | A1 | 10/2013 | Cardinale et al. |
| 2013/0304091 | A1 | 11/2013 | Straehnz et al. |

\* cited by examiner

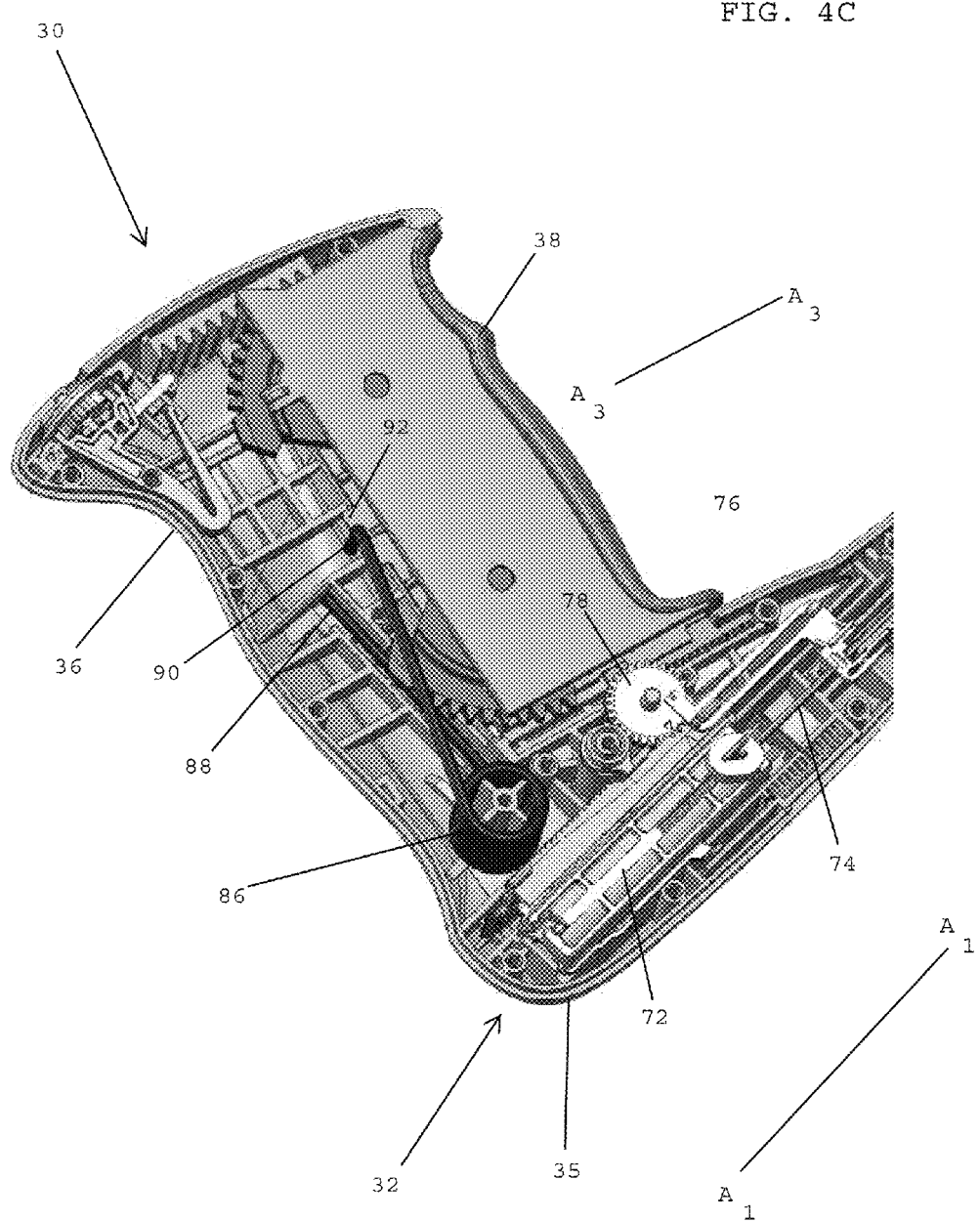

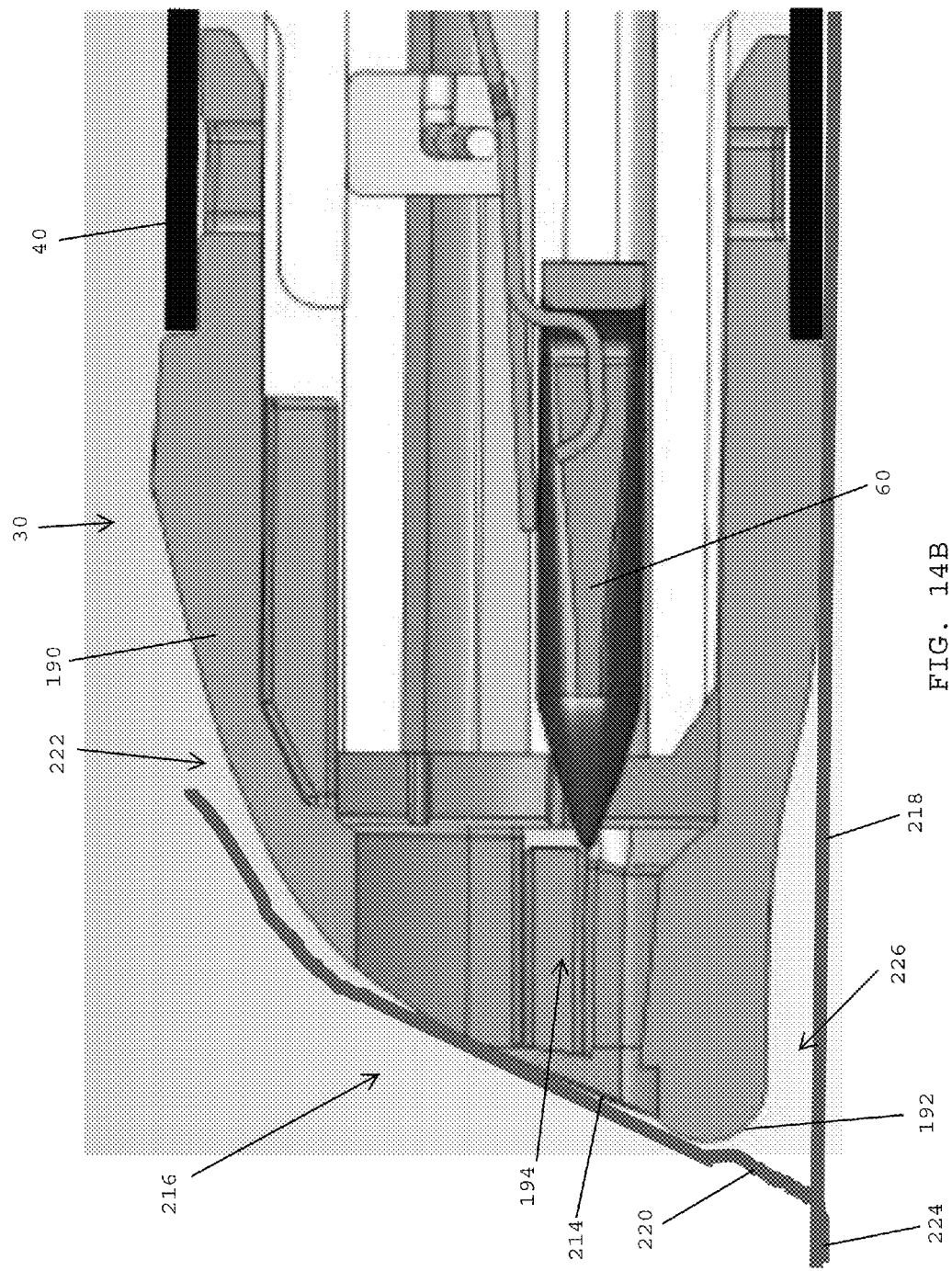

APPLICATOR INSTRUMENTS FOR DISPENSING SURGICAL FASTENERS DURING OPEN REPAIR PROCEDURES

CROSS REFERENCE TO RELATED APPLICATIONS

The present application is a continuation of commonly assigned U.S. patent application Ser. No. 13/470,022, filed May 11, 2012, now U.S. Pat. No. 8,518,055, and is related to commonly assigned U.S. patent application Ser. No. 13/470,065, filed May 11, 2012, and U.S. Patent Appln. Publication Nos. 2010/0292715, now U.S. Pat. No. 8,894,669, 2010/0292712, now U.S. Pat. No. 8,579,920, 2010/0292710, now U.S. Pat. No. 8,728,098, 2010/0292713, now U.S. Pat. No. 8,728,099, and 2011/079627, now U.S. Pat. No. 8,920,439, the disclosures of which are hereby incorporated by reference herein.

BACKGROUND OF THE INVENTION

1. Field of the Invention

The present invention generally relates to medical devices and surgical procedures for correcting defects, and more specifically relates to applicator instruments, surgical fasteners and methods used during open hernia repair procedures, such as ventral hernias.

2. Description of the Related Art

Hernia is a condition whereby a small loop of bowel or intestine protrudes through a weak place or defect within the abdominal muscle wall or groin of a patient. This condition commonly occurs in humans, particularly males. Hernias of this type may result from a congenital defect, or may be caused by straining or lifting heavy objects. Lifting heavy objects can generate a large amount of stress upon the abdominal wall, which may rupture or tear to create the defect or opening. In any case, the patient may be left with an unsightly bulge of abdominal contents protruding through the defect, which may result in pain, reduced lifting abilities, and in some cases, impaction of the bowel, or possibly other complications if the flow of blood is cut off to the protruding tissue.

A common solution to the above-described problem may be surgery. During an open surgical procedure, the defect is accessed and carefully examined through an open incision. Careful examination is required due to the network of vessels and nerves which exist in the area of a typical defect, which requires a surgeon to conduct a hernia repair with great skill and caution. Within this area can be found vascular structures such as gastric vessels, the external iliac vessels, and the inferior epigastric vessels.

Once the surgeon is familiar with the anatomy of a patient, the surgeon carefully places the viscera back into the patient's abdomen through the defect. Repairing the defect can involve closure of the defect with sutures or fasteners but generally involves placing a surgical prosthetic such as a mesh patch over the open defect, and attaching the mesh patch to the abdominal wall or inguinal floor with conventional suture or with surgical fasteners. The mesh patch acts as a barrier and prevents expulsion of bowel through the defect.

At present, there are a variety of surgical instruments and fasteners available for attaching a mesh patch to tissue. One type of instrument is a surgical stapler whereby a stack of unformed staples are contained within a cartridge in a serial fashion sequentially advanced within the instrument by a spring mechanism. A secondary feeding mechanism separates a distal-most staple from the stack, holds back the remainder of the stack, and feeds the distal-most staple into a staple forming mechanism. Feeding mechanisms of this type are found in U.S. Pat. No. 5,470,010 to Rothfuss et al., and in U.S. Pat. No. 5,582,616, to Bolduc et al.

Another hernia mesh attachment instrument uses a helical wire fastener that resembles a small section of spring. Multiple helical wire fasteners may be stored serially within a 5 mm shaft, and may be corkscrewed or rotated into tissue. A load spring may be used to bias or feed the plurality of helical fasteners distally within the shaft. A protrusion extends into the shaft to possibly prevent the ejection of the stack of fasteners by the load spring and may permit passage of a rotating fastener. Instruments and fasteners of these types are found in U.S. Pat. No. 5,582,616 to Bolduc et al., U.S. Pat. No. 5,810,882 to Bolduc et al., and in U.S. Pat. No. 5,830,221 to Stein et al.

The above-listed references teach using a spring mechanism to feed a plurality of fasteners through the surgical instrument. Spring mechanisms typically use a long soft coil spring to push a stack of fasteners through a guide or track within the shaft of the surgical instrument. These types of feeding mechanisms may be generally simple and reliable, however, they require a supplemental valving mechanism to separate and feed the lead surgical fastener from the stack.

Other instruments dispense surgical fasteners using either a reloadable single shot instrument or a rotary magazine that holds a small number of fasteners. These types of surgical fastening instruments can be found in U.S. Pat. No. 5,203,864 and U.S. Pat. No. 5,290,297, both to Edward Phillips. These instruments have not gained acceptance by the surgical community, possibly due to their single shot capabilities and the large size of the rotary magazine, which can restrict the use of such an instrument to an open procedure.

An instrument with a reciprocating feeding mechanism is described in U.S. Pat. Nos. 5,601,573; 5,833,700; and 5,921,997 to Fogelberg et al. The Fogelberg et al. references teach a clip applier with a feeding mechanism that utilizes a reciprocating feed bar to feed a serial stack of clips. A feeder shoe may operably engage with and move with the distally moving feed bar and may slidingly engage with the proximally moving feed bar. Thus, the feeder shoe may index or push the stack of clips distally with the distally moving feed bar and remains stationary relative to the proximally moving feed bar. A supplemental valving mechanism separates the distal-most clip from the stack and holds the remainder of the stack stationary as the distal-most clip is applied onto a vessel. Although the Fogelberg et al. references teach a reciprocating feeding mechanism with a single reciprocating member, they do not teach the use of the clip applier in the attachment of hernia mesh, nor do they teach the individual driving or feeding of each clip by a moving member.

Another fastener feeding mechanism that uses reciprocation is that disclosed in U.S. Pat. No. 4,325,376 to Klieman et al. A clip applier that stores a plurality of clips in a serial fashion within a clip magazine is disclosed. The clips are in a stack wherein the proximal most clip may be pushed or fed distally by a pawl that may be ratcheted or indexed distally by a reciprocating member or ratchet blade with each actuation of the instrument. As the pawl indexes distally, it can push the stack of clips distally. A secondary valving mechanism may be also described. Thus, the feeding mechanism of Klieman et al. teaches the use of a single reciprocating member and pawl to push or feed the stack of clips distally, and may require a secondary valving mechanism to feed the distal most clip.

U.S. Pat. No. 3,740,994 to DeCarlo Jr. describes a novel reciprocating feeding mechanism that may index a plurality of staples or clips, and may ready them for discharge by reciprocating one of a pair of opposing leaf spring assemblies. The staples reside serially within a guide rail with a fixed leaf spring assembly extending into the plane of the guide rail. A reciprocating leaf spring assembly may oppose and extend inwardly toward the fixed leaf spring assembly. As the reciprocating leaf spring assembly moves distally, each of individual leaf springs of the assembly may engage a staple and move it distally. The distally moving staples deflect the local individual leaf springs of the fixed leaf spring assembly, and the deflected leaf springs may return to the un-deflected position after passage of the staple. As the moving leaf spring assembly moves proximally, the leaf springs of the fixed leaf spring assembly hold the staples stationary and prevent proximal movement thereof. A secondary guide rail and valving mechanism may be provided to separate a single staple from the stack for forming and can hold the stack of staples stationary as the single clip is formed.

Additionally, similar feeding mechanisms are disclosed in U.S. Pat. No. 4,478,220 to DiGiovanni et al. and U.S. Pat. No. 4,471,780 to Menges et al. Both of these related patents teach a reciprocating feeding mechanism that uses one fixed member and one reciprocating member to feed or index a plurality of clips distally. Angled flexible fingers may be hingedly attached to the reciprocating member and operatively engage the clips when moving distally, and slidingly engage with the clips when moving proximally. The angled flexible fingers within the fixed member deflect out of the way when the clips move distally and spring up to stop proximal movement of the clip after the clip has passed. A secondary valving mechanism is also disclosed.

Commonly assigned U.S. Patent Application Publication No. 2002/0068947, the disclosure of which is hereby incorporated by reference herein, teaches a device for delivering a plurality of individual surgical fasteners. In one embodiment, the delivery device includes a drive mechanism having distal and proximal ends. The drive mechanism has a moving member and a fixed opposing member, whereby the moving member is moveable proximally and distally with respect to the delivery device. The moving member has a sharpened distal end for piercing tissue. The device includes at least one surgical fastener located between the first and the second members. Each of the surgical fasteners has a proximal end and a distal end. The device also has an actuator having at least two sequential positions. A first position for advancing the moving member distally and piercing tissue, and a second position for retracting the moving member proximally, thereby deploying the distal end of the fastener.

Tacks for mesh fixation have generally been made of metal, such as stainless steel, nitinol, or titanium. The metal tacks were necessary to provide for sufficient holding strength, penetration of various prosthetic meshes, and for ease of manufacture. Until recently, there were no absorbable tacks available on the market, and surgeons could only use absorbable sutures in order to provide a fixation means that did not permanently stay in the body. However, using sutures is exceedingly difficult for some repair procedures. With surgical trends leading to minimum foreign body accumulation, an absorbable tack with minimum profile is needed.

In spite of the above advances, there remains a need for further improvements. In particular, there remains a need for applicator instruments that enable surgeons to accurately and easily dispense surgical fasteners into tissue for tissue repair procedures, there remains a need for applicator instruments that enable surgical fasteners to be accurately and easily dispensed in small areas, and for surgical fasteners that are absorbable.

SUMMARY OF THE INVENTION

In one embodiment, an applicator instrument is a multi-fire device having a curved shaft that delivers surgical fasteners for the fixation of mesh material to soft tissue. The applicator instrument may be used for open surgical repair procedures that address ventral hernias. In one embodiment, a series of surgical fasteners are housed within the shaft of the applicator instrument and the distal end of the shaft is oriented at an angle relative to the proximal end of the shaft that is attached to a handle.

In one embodiment, the multi-fire applicator instrument has a series of strap implants or surgical fasteners stored along the length of the shaft. The applicator has a firing system including a pair of flat stampings with tabbed features. One stamping is stationary and the other stamping cycles in distal and proximal directions to facilitate incremental feeding of the surgical fasteners along the length of the shaft. The flat nature of the stampings facilitates assembly and flexibility as the stampings are guided through a curved path. In one embodiment, a pair of long, molded guide components creates the curved path of travel with minimal friction and distortion. The molded components are desirably contained within the shaft, which may be a stainless steel cannula.

In one embodiment, at the distal end of the shaft, a wire staging spring applies a downward force on the distal end of the stationary tabbed stamping. The force applied by the wire spring positions and aligns the surgical fasteners with the dispensing end of the device. When a surgical fasteners reaches a lead position at the distal end of the shaft, the cycled stamping is retracted, and the wire spring moves the lead fastener downward from the advancing channel into the firing channel. From the firing channel, the fastener is dispensed via a firing system including a firing rod and a stored energy system in the handle. The wire spring provides a spring force mechanism that is more economical and easier to assemble within a system.

In one embodiment, a contoured tip or cap is attached to the distal end of the shaft. The contours on the cap make the distal end of the applicator instrument atraumatic to a skirted mesh.

In one embodiment, the cap has a lower distal edge that may be pronounced and that may have a curved bottom surface. The lower distal edge is preferably advanced into the seam of a skirted mesh, and fits into the pocket areas or corners of various brands and sizes of skirted meshes, which ensures that that the surgical fastener delivery window is a set distance above and from the seam or hem of the skirted mesh.

In one embodiment, the cap has extensions or wing-like features that are in line with and lateral to the lower distal edge. The lower distal edge and the lateral extensions preferably allow the applicator instrument to slide more freely within the seam of the mesh and distribute forces over a broader area of mesh when a physician is applying forward forces on the handle of the applicator instrument and counter pressure on opposing tissue. The extensions also stabilize and orient the tip of the device to ensure straps are delivered upward into the targeted upper layer of a skirted mesh implant.

In one embodiment, the cap has a sloped distal face that slopes upwardly and proximally from the lower distal edge to ply the top mesh piece of an open skirt mesh away from mesh seam area. In one embodiment, the cap has a bottom surface that is abutted against a bottom mesh piece of the open skirt mesh.

The cap is desirably affixed to the distal end of the shaft so that it does not rotate or translate relative to the shaft. In one embodiment the proximal end of the cap transitions into a cylindrical shape that matches the outer diameter (e.g. 8 mm OD) of the shaft.

The contoured, atraumatic cap has no sharp edges at the distal end of the shaft. Thus, a physician may slide the cap along the inside of the seam of an open skirt mesh when positioning or repositioning the device for initial and subsequent surgical fastener deployment, and the cap will not catch on meshes of varying pore size.

In one embodiment, the handle and the trigger or actuation portion of the applicator instrument is re-positioned above the housing or main body of the device. This configuration places the trigger of the applicator instrument in a position that provides multiple advantages to the user. First, the handle is located in a position that is ergonomically acceptable and allows the user's elbow to be in a neutral position when ready to fire. In one embodiment, the handle is angled forward toward the distal end of the applicator instrument to facilitate a neutral position for the user's wrist, as well. The position of the handle above the main body portion of the applicator instrument enables the device to clear the body of the patient, which is preferable in open abdominal procedures.

The combination of an upward curvature of a curved shaft and a forward angulation of the handle complement each other to facilitate the delivery of surgical fasteners upward in the intended direction of fixation. In one embodiment, the applicator instrument has a counter/indicator that shows how many surgical fasteners have been fired or remain in the applicator instrument. The counter/indicator is preferably positioned at the top of the handle to provide easy visibility when the handle is in the upright and ready to fire position. Coupled with a lockout mechanism, the counter/indicator also indicates when the straps are running out and when the instrument is empty.

In one embodiment, the trigger has a linear motion that enables the actuation of the device to feel secure and stable in a surgeon's hand. The orientation of the trigger and the location of the counter/indicator suggests the proper orientation or intended use of the device. In one embodiment, the trigger has an index finger groove on the surface of the trigger that further suggests the proper orientation of the device.

The linear motion of the trigger provides consistency regarding the force and distance required to squeeze the trigger no matter where up or down the length of the trigger that the finger forces are concentrated.

In one embodiment, an upright handle orientation is required for correctly orienting the surgical fasteners with the position of the hernia mesh against the abdominal wall. The geometry of the tip's sloped face also preferably ensures that when the device is oriented correctly, a surgical fastener may be delivered in the correct orientation relative to the mesh and the abdominal wall tissue, and positioned a preferred distance away from the seam of the skirted mesh.

The trigger moves along a linear path, which facilitates a unique rack and pinion type linkage to translate motion to the firing system located in the housing of the applicator instrument. In one embodiment, the firing system includes a stored energy system used to apply energy to dispense a surgical fastener. The firing system has a compression spring, also referred to herein as a firing spring, disposed within a box-like component, a linkage coupled with the trigger for compressing the firing spring for storing energy in the firing spring, and a firing spring release for releasing the compressed spring at a predetermined load and timed interval relative to the trigger position.

In one embodiment, the trigger is supported internally by a pair of rotating members. The trigger preferably has only two rotation point contacts so that the potential risks of binding are eliminated. The rotating members are coupled to each other with a gear system, which ensures that the two members will rotate at the same rate. In addition, a torsional return spring may be connected between the rotating members to ensure that after actuation of the trigger, the trigger and the firing system are returned to an initial stage of a firing cycle and the lowest energy state. The configuration of the trigger return spring and its position relative to the trigger may allow for a low, near-uniform trigger return force (pre-load and travel force of the trigger alone to the operator's hand), which is an improvement over the high trigger forces required in earlier applicator instruments. An alternative embodiment may include a torsional spring that acts directly onto the trigger. The torsional spring provides a moment that effectively counteracts any moment applied by the user during device actuation.

In one embodiment, an applicator instrument for dispensing surgical fasteners includes a housing defining a bottom of the applicator instrument, a firing system disposed in the housing and being moveable in distal and proximal directions along a first axis, and a handle extending upwardly from the housing along a second axis that defines an acute angle with the first axis, the handle having an upper end that defines a top of the applicator instrument. In one embodiment, the handle is located at a proximal end of the applicator instrument and is angled to lean toward a distal end of the applicator instrument. The applicator instrument preferably includes a trigger mounted on the handle for actuating the firing system.

The applicator instrument preferably has an elongated shaft extending from the housing. In one embodiment, a plurality of surgical fasteners is loaded into the elongated shaft for being dispensed from the distal end of the elongated shaft when the trigger is pulled. The elongated shaft desirably has a proximal section that extends along the first axis and a distal section that is oriented at an angle relative to the proximal section for extending upwardly toward the top of the application instrument. In one embodiment, the shaft has a curve between the proximal shaft section and the distal shaft section.

In one embodiment, the applicator instrument includes a linkage coupling the trigger with the handle and the firing system. In one embodiment, the linkage preferably constrains movement of the trigger to a linear path that extends along a third axis that defines an acute angle with the first axis and that is perpendicular to the second axis of the handle.

In one embodiment, the trigger is moveable along a linear path that extends along the third axis for moving toward the proximal end of the applicator instrument for activating the linkage, which, in turn, moves the firing system along the first axis toward the distal end of the applicator instrument.

In one embodiment, the applicator instrument desirably includes a guide member disposed inside the elongated shaft and extending along the length of the elongated shaft. The guide member may be angled or curved. In one embodiment, the guide member is curved and has a curved conduit that extends along the length of the guide member. The curved conduit may include an advancing channel for advancing the surgical fasteners toward the distal end of the elongated shaft, and a firing channel for dispensing the surgical fasteners one at a time from the distal end of the elongated shaft.

In one embodiment, the applicator instrument preferably includes an advancer element disposed in the advancer element channel and being moveable in distal and proximal directions for advancing the surgical fasteners toward the distal end of the elongated shaft, and an anti-backup member disposed in the advancer element channel and opposing the advancer element for preventing the surgical fasteners from moving toward the proximal end of the elongated shaft.

In one embodiment, a firing rod is disposed in the firing channel and is moveable between a retracted position and an extended position for dispensing a lead surgical fastener from the distal end of the elongated shaft. A distal-most end of the anti-backup member desirably includes a staging leaf that receives a leading one of the surgical fasteners from the advancer element and transfers the leading one of the surgical fasteners from the advancer element channel to the firing channel for being aligned with the firing rod. The applicator instrument desirably has a wire staging spring attached to the guide member and having a distal end that contacts the staging leaf for applying a spring force for urging the staging leaf into alignment with the firing channel.

In one embodiment, the guide member desirably includes a window formed in an outer wall thereof that is in alignment with the staging leaf. The distal end of the wire staging spring preferably passes through the window for engaging the staging leaf.

In one embodiment, the advancer element and the anti-backup member are flat, elongated metal stampings with tabs extending therefrom that project toward the distal end of the elongated shaft. In one embodiment, the tabs on the anti-backup member extend toward the advancer element, and the tabs on the advancer element extend toward the anti-backup member.

In one embodiment, the linkage may also include a first rotating link having upper gear teeth and lower gear teeth, the first rotating link being disposed inside an upper portion of the trigger, and a first pivot pivotally securing the first rotating link to the upper portion of the trigger. The linkage may also include a second rotating link having upper gear teeth and lower gear teeth, the second rotating link being disposed inside a lower portion of the trigger, and a second pivot pivotally securing the second rotating link to the lower portion of the trigger. The lower gear teeth of the first rotating link preferably mesh with the upper gear teeth of the second rotating link so that when the trigger is squeezed the first and second rotating links rotate at the same rate.

In one embodiment, the applicator instrument desirably includes a first rack located near the upper end of the handle for meshing with the upper gear teeth of the first rotating link and a second rack located near an upper end of the housing of the applicator instrument for meshing with the lower gear teeth of the second rotating link.

In one embodiment, a first elongated slot is formed in an upper section of the handle for receiving the first pivot. The first elongated slot desirably extends along a fourth axis that is parallel to the third axis, and first pivot is moveable in proximal and distal directions within the first elongated slot. In one embodiment, a second elongated slot is formed in a lower section of the handle for receiving the second pivot. The second elongated slot preferably extends along a fifth axis that is parallel to both the third axis and the fourth axis, and the second pivot is moveable in proximal and distal directions within the second elongated slot. In one embodiment, when the trigger is squeezed, the first and second pivots desirably move simultaneously through the respective first and second elongated slots and toward the proximal end of the applicator instrument. The first and second elongated slots ensure that the two rotating links rotate at the same rate and may be used instead of the gear teeth and the racks described in the previous embodiment.

In one embodiment, the applicator instrument desirably includes a trigger rack connected with a lower end of the trigger for moving simultaneously with the trigger in distal and proximal directions along the third axis, and a drive gear having a first set of gear teeth that mesh with the trigger rack and a second set of gear teeth that mesh with teeth on a sliding yoke that slides in distal and proximal directions along the first axis. The trigger rack is separate from the trigger component, allowing for some amount of play and rotation between the two components. Further, as a separate component, the trigger rack can be made of a stronger material and in a more economical manner.

In one embodiment, when the trigger is squeezed and moves proximally, the drive gear moves the firing system distally. In one embodiment, when the trigger moves distally, the drive gear desirably moves the firing system proximally.

In one embodiment, the applicator instrument preferably includes a counter located at an upper end of the handle for indicating the number of surgical fasteners dispensed from and/or remaining in the applicator instrument. In one embodiment, the counter desirably includes a counter window formed at the upper end of the handle, a rotatable disc visible through the counter window, a rotatable gear connected with the rotatable disc and having teeth extending below the rotatable disc, and a lockout counter pivotally secured to the handle for toggling between a forward position and a rear position. The lockout counter preferably has a first tooth that engages the rotatable gear teeth when in the forward position and a second tooth that engages the rotatable gear teeth when in the rear position. The counter preferably includes a lockout counter spring in contact with the lockout counter for normally urging the lockout counter into the forward position. In one embodiment, when the trigger is fully squeezed, the first rotating link contacts the lockout counter for overcoming the force of the lockout counter spring for toggling the lockout counter into the rear position, whereby the first and second teeth of the lockout counter engage the teeth of the rotatable gear for rotating the rotatable disc. The spring member on the lockout counter allows for additional over travel of the rotating link after the counter completes its counting cycle.

In one embodiment, an applicator instrument for dispensing surgical fasteners desirably includes a housing defining a bottom of the applicator instrument, a firing system disposed in the housing and being moveable in distal and proximal directions, and a handle extending upwardly from the housing and being angled toward a distal end of the applicator instrument, the handle having an upper end that defines a top of the applicator instrument. The applicator instrument desirably includes a shaft extending distally from the housing near the bottom of the applicator instrument, the shaft having a proximal section that extends along a longitudinal axis of the applicator instrument and a distal section that is oriented at an angle relative to the proximal section for extending upwardly toward the top of the application instrument. A plurality of surgical fasteners is preferably loaded in series into the shaft, and a cap is secured to the distal end of the shaft, the cap having a lower distal edge and a distal face that slopes upwardly and proximally from the lower distal edge. The cap preferably includes a delivery window formed in the distal face, the delivery window having a lower end that is spaced from the lower distal edge. A trigger is desirably mounted on the handle for actuating the firing system for dispensing the surgical fasteners through the delivery window.

In one embodiment, the applicator instrument preferably includes a guide member disposed inside the shaft and extending along the length of the shaft, the guide member having a curved conduit that extends along the length of the guide member. The curved conduit desirably includes an advancing channel for advancing the surgical fasteners toward the distal end of the shaft, and a firing channel for dispensing the surgical fasteners through the dispensing window of the cap. An advancer element is preferably disposed in the advancer element channel and is moveable in distal and proximal directions for advancing the surgical fasteners toward the distal end of the shaft, and a stationary anti-backup member is preferably disposed in the advancer element channel and opposes the advancer element for preventing the surgical fasteners from moving toward the proximal end of the shaft.

In one embodiment, a firing rod is disposed in the firing channel and is moveable between a retracted position and an extended position for dispensing the surgical fasteners from the distal end of the shaft. The stationary anti-backup member preferably has a staging leaf at a distal end thereof that receives a leading one of the surgical fasteners from the advancer element and transfers the leading one of the surgical fasteners from the advancer element channel to the firing channel for being aligned with the firing rod. In one embodiment, a wire staging spring is attached to the guide member and has a distal end that contacts the staging leaf for urging the staging leaf into alignment with the firing channel.

In one embodiment, an applicator instrument for dispensing surgical fasteners includes a housing, a firing system disposed in the housing, an actuator coupled with the housing for actuating the firing system, an elongated shaft extending from the housing, the elongated shaft having an outer diameter, and a cap secured to the distal end of the elongated shaft, whereby the cap has a lower distal edge that extends laterally beyond the outer diameter of the elongated shaft.

In one embodiment, the housing defines a bottom of the applicator instrument. The applicator instrument preferably has a handle extending upwardly from the housing and that is angled or leans toward the distal end of the elongated shaft. In one embodiment, the handle has an upper end that defines a top of the applicator instrument. The actuator may be a trigger that is mounted onto the handle.

The firing system is desirably disposed in the housing and is moveable in distal and proximal directions along the first axis. The handle preferably extends along a second axis that defines an acute angle with the first axis of about 70-80° and more preferably about 75°.

In one embodiment, the lower distal edge of the cap desirably has a length that is greater than the outer diameter of the elongated shaft. In one embodiment, the cap has a distal end face that slopes upwardly and proximally from the lower distal edge.

In one embodiment, the cap preferably has a surgical fastener delivery window formed in the distal end face for dispensing surgical fasteners. The delivery window desirably has a lower end that is spaced from the lower distal edge. In one embodiment, the cap has a bottom surface, and the lower distal edge of the cap has a thickness extending between the bottom surface of the cap and the lower end of the delivery window.

In one embodiment, the proximal end of the cap has an outer diameter of about 6-12 mm and more preferably about 8 mm that matches and conforms to the outer diameter of the elongated shaft.

In one embodiment, the elongated shaft is mounted to the housing and extends distally from the housing. In one embodiment, the elongated shaft has a proximal section that extends along a first axis and a distal section that is oriented at an angle relative to the proximal section for extending upwardly toward the top of the applicator instrument. In one embodiment, the elongated shaft has a curve located between the proximal shaft section and the distal shaft section.

These and other preferred embodiments of the present invention will be described in more detail below.

BRIEF DESCRIPTION OF THE DRAWING

FIG. 4C shows a perspective view of the proximal end of the applicator instrument shown in FIG. 4A.

FIG. 6A-1 shows the counter of FIGS. 5A-5C during the first stage of the firing cycle shown in FIG. 6A.

FIG. 6B-1 shows the counter during the second stage of the firing cycle shown in FIG. 6B during which a rotating link has begun to contact a counter.

FIG. 6C-1 shows the counter during the third stage of the firing cycle shown in FIG. 6C during which the counter has begun to deflect a dwell beam of the counter.

FIG. 6D-1 shows the counter during the fourth stage of the firing cycle shown in FIG. 6D during which the counter has pivoted to a rear position.

FIG. 6E-1 shows the counter during the fifth stage of the firing cycle shown in FIG. 6E during which the dwell beam of the counter is deflected further by a rotating link.

FIG. 14B shows a magnified cross-sectional view of FIG. 14A.

DETAILED DESCRIPTION

Figure 1:
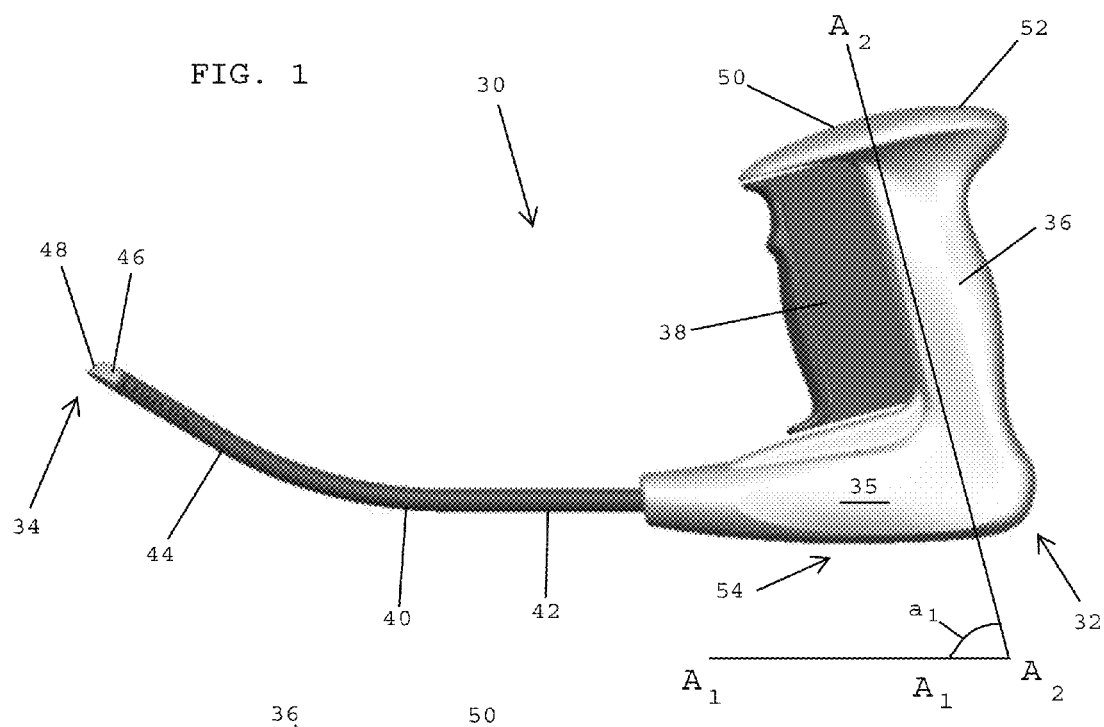
FIG. 1 shows a left side view of an applicator instrument for dispensing surgical fasteners, in accordance with one embodiment of the present invention.

Referring to FIG. 1, in one embodiment, an applicator instrument 30 for dispensing surgical fasteners has a proximal end 32, a distal end 34, and a longitudinal axis $A_1$-$A_1$ that extends between the proximal and distal ends. The applicator instrument 30 desirably includes a housing 35, a handle 36 extending upwardly from the housing, a trigger 38 mounted on the handle, and an elongated shaft 40 that extends distally from the housing 35. The elongated shaft 40 includes a first section 42 that extends along the longitudinal axis $A_1$-$A_1$ of the applicator instrument, and a second section 44 that is angled or curved relative to the first section 42.

In one embodiment, a cap 46 is secured to the distal end of the elongated shaft 40. The cap 46 preferably has a distal face 48 that slopes away from a lower distal edge of the cap and toward the proximal end 32 of the applicator instrument 30.

In one embodiment, the handle 36 includes an upper end 50 containing a counter 52 that indicates how many surgical fasteners have been dispensed and/or how many surgical fasteners remain loaded in the applicator instrument. In one embodiment, the counter 52 locks the applicator instrument from further use when the last surgical fastener has been dispensed.

In one embodiment, the counter 52 is visible at the upper end 50 of the handle 36 to provide a visual indicator of how many of the surgical fasteners have been dispensed. The upper end of the handle defines the top of the applicator instrument 30. The housing 35 has a lower end 54 that defines the bottom of the applicator instrument 30.

In one embodiment, the handle 36 preferably leans toward the distal end 34 of the applicator instrument 30 to provide improved ergonomics for a surgeon so that the surgeon may maintain his/her elbow and wrist in a neutral position. In one embodiment, the handle 36 preferably extends along a longitudinal axis $A_2$-$A_2$ that defines an acute angle α1 with the longitudinal axis $A_1$-$A_1$ of the applicator instrument. In one embodiment, the angle α1 is about 70-80° and more preferably about 75°. During a surgical procedure, the lower end 54 of the housing 35 preferably faces toward a patient and the upper end 50 of the handle 36 preferably faces away from the patient.

Figure 2:
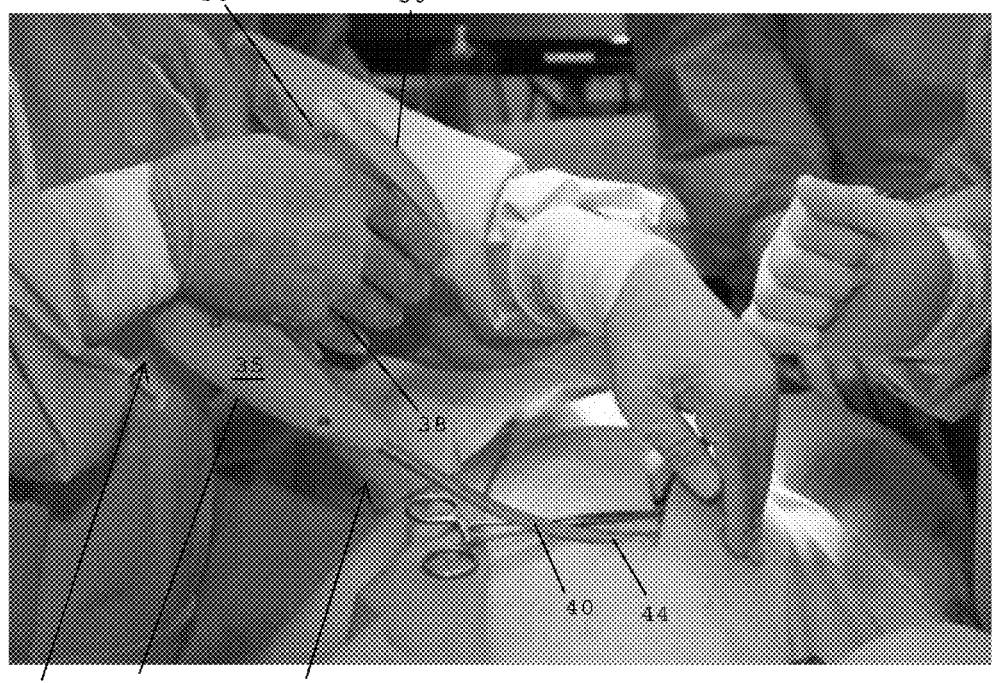
FIG. 2 shows a perspective view of a right side of the applicator instrument of FIG. 1 during a surgical procedure, in accordance with one embodiment of the present invention.

Referring to FIG. 2, in one embodiment, the applicator instrument 30 shown in FIG. 1 may be used for dispensing surgical fasteners during a surgical procedure such as an open hernia repair procedure. In one embodiment, the applicator instrument 30 has a plurality of surgical fasteners that are pre-loaded in the shaft 40 for being dispensed when the trigger 38 is squeezed. In one embodiment, a single surgical fastener is dispensed each time the trigger 38 is squeezed. In one embodiment, the applicator instrument 30 is used for dispensing surgical fasteners for the fixation of a mesh, such as a surgical mesh, to the soft tissue of a patient.

In FIG. 2, the angled second section 44 of the shaft 40 has been inserted into a surgical opening. The lower end 54 of the housing 35 faces toward the patient and the upper end 50 of the handle 36 faces away from the patient. A surgeon may grasp the handle 36 and squeeze the trigger 38 for dispensing a surgical fastener from the distal end of the shaft 40. In one embodiment, the surgeon pulls the trigger 38 proximally (i.e. toward the proximal end 32 of the applicator instrument) for dispensing the surgical fasteners. The surgeon preferably applies counter pressure on the patient's tissue that opposes the distal end of the applicator instrument. In one embodiment, a single surgical fastener is dispensed each time the surgeon pulls the trigger 38 proximally, and the system finishes the firing cycle when the trigger is released for allowing the trigger to return distally.

The second section 44 of the shaft 40 that is curved and/or angled relative to the first section 42 of the shaft preferably facilitates the accurate placement of surgical fasteners into soft tissue. In one embodiment, the applicator instrument 30 is used during an open surgical repair procedure for addressing ventral hernias. The distal-most end of the curved shaft 40 is inserted into a pocket of an open skirt mesh having a top mesh piece and a bottom mesh piece that are joined together at a peripheral seam, whereupon surgical fasteners are dispensed from the distal end of the applicator instrument for fixing the top mesh piece to soft tissue.

In one embodiment, the handle 36 and the trigger 38 are positioned above the housing 35 of the applicator instrument. This configuration places the trigger 38 in a position that provides multiple advantages to a surgeon. First, the handle 36 is located in a position that allows a surgeon's elbow to be in a neutral position. The handle 36 is also angled forward toward the distal end 34 of the applicator instrument 30 to facilitate a neutral position for the surgeon's wrist. In addition, the position of the handle 36 above the housing 35 of the applicator instrument 30 allows the bottom end 52 of the housing 35 to clear the body of the patient, which is particularly preferable for open abdominal procedures.

In one embodiment, the combination of an upward curvature of the shaft 40 and the forward angulation or lean of the handle 36 toward the distal end 34 of the applicator instrument complement each other to facilitate the delivery of surgical fasteners along an upward trajectory in the intended direction of fixation.

In one embodiment, the applicator instrument 30 is a multi-fire device including a plurality of surgical fasteners stored therein as disclosed in commonly assigned U.S. Patent Application Publication Nos. US 2010/0292715; US 2010/0292712; US 2010/0292710; US 2010/0292713; and US 2011/079627, the disclosures of which are hereby incorporated by reference herein. In one embodiment, the applicator instrument includes a plurality of surgical fasteners stored in series along the length of the shaft 40. The shaft 40 preferably includes a pair of flat stampings having tabbed features incorporated therein. One of the flat stampings is stationary for preventing the surgical fasteners from moving proximally within the shaft 40. The other flat stamping cycles in distal and proximal directions each time the trigger 38 is squeezed and then released to facilitate incremental advancement of the surgical fasteners along the length of the shaft 40. The flat nature of the stampings provides the stampings with flexibility so that the stampings may curve to conform to the curvature of the shaft while guiding the surgical fasteners along the curved path defined by the shaft 40.

In one embodiment, the applicator instrument includes a molded guide component that defines the curved path of travel for the surgical fasteners. The flat stampings are placed inside the molded guide component. The molded guide component preferably provides minimal friction and distortion upon the surgical fasteners, the advancer element and the anti-backup member as the surgical fasteners move distally through the shaft 40. In one embodiment, the guide component is made of molded plastic and includes two halves that are assembled together for being contained within a conduit extending through the elongated shaft 40.

Figure 3:
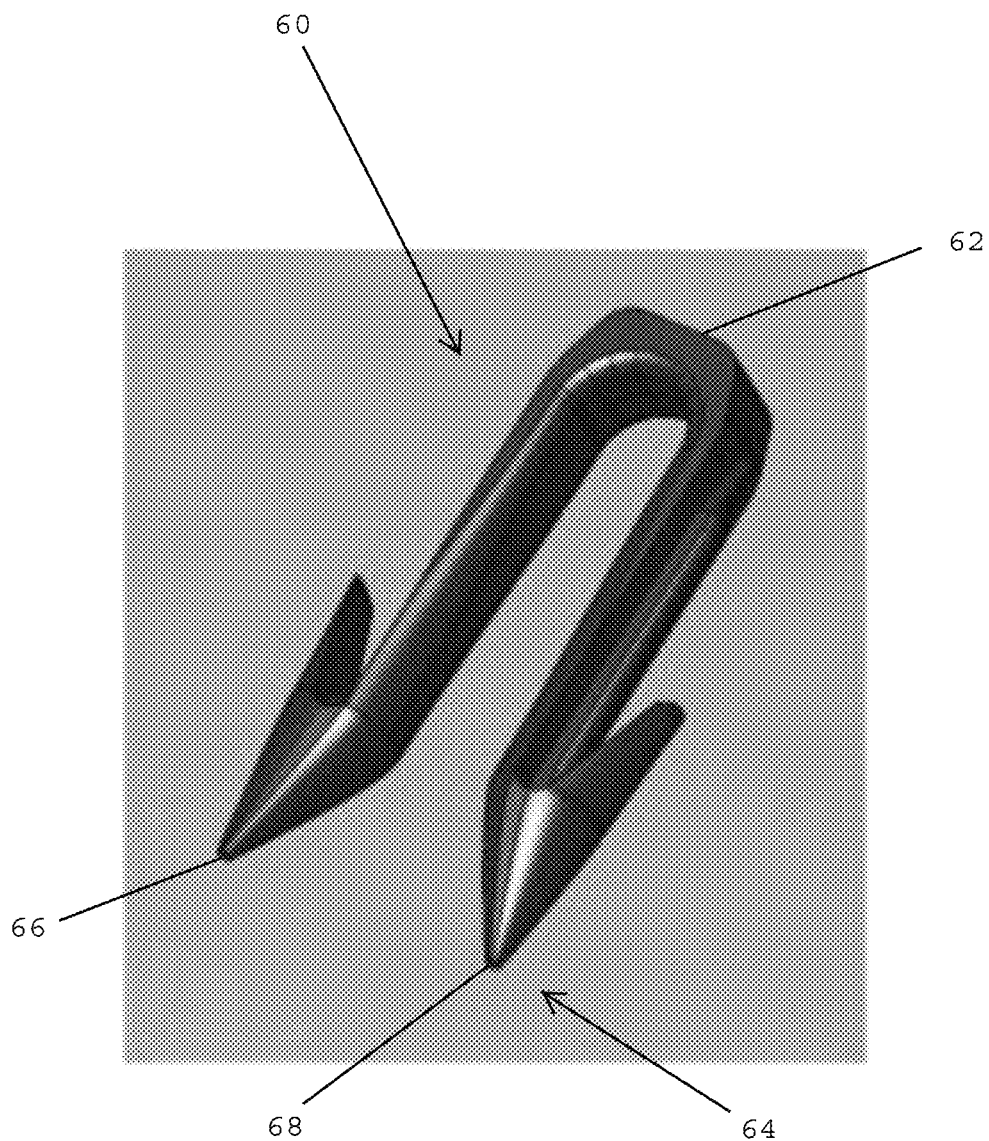
FIG. 3 shows a perspective view of a surgical fastener dispensed from the applicator instrument shown in FIGS. 1 and 2, in accordance with one embodiment of the present invention.

Referring to FIG. 3, in one embodiment, a plurality of surgical fasteners are pre-loaded into the shaft of the applicator instrument 30 shown in FIGS. 1 and 2. A single surgical fastener 60 includes a proximal end 62 and a distal end 64 having a pair of tapered ends 66, 68 that are spaced from one another for capturing mesh fibers between the tapered ends. In one embodiment, the surgical fastener 60 has one or more of the features disclosed in commonly assigned U.S. Patent Application Publication Nos. US 2010/0292715, US 2010/0292712, US 2010/0292710, US 2010/0292713, and US 2011/079627, the disclosures of which are hereby incorporated by reference herein.

Figure 4A:
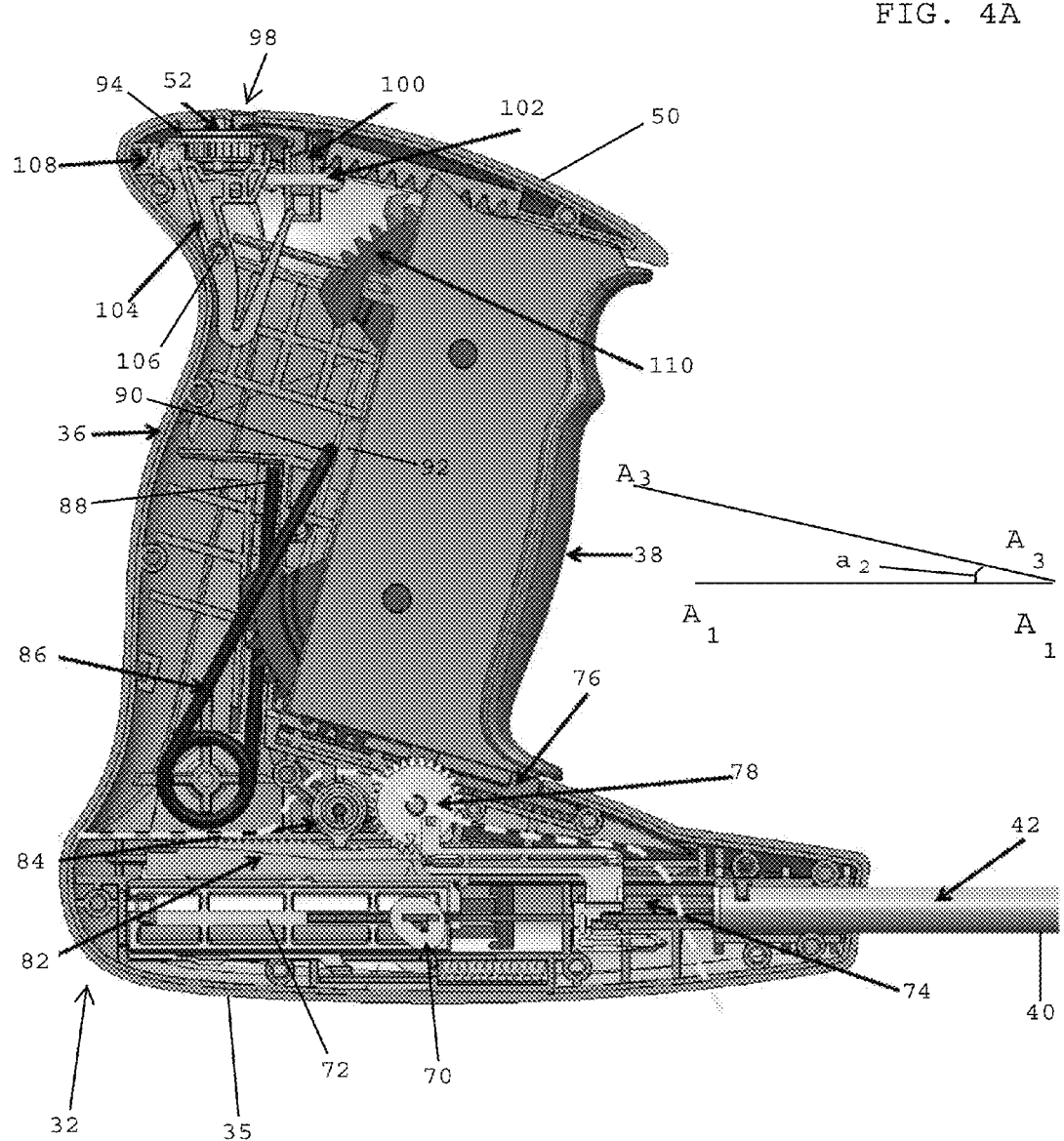
FIG. 4A shows a right side elevation view of a proximal end of an applicator instrument used for dispensing surgical fasteners with a right half of a handle removed for showing internal components, in accordance with one embodiment of the present invention.
Figure 4B:
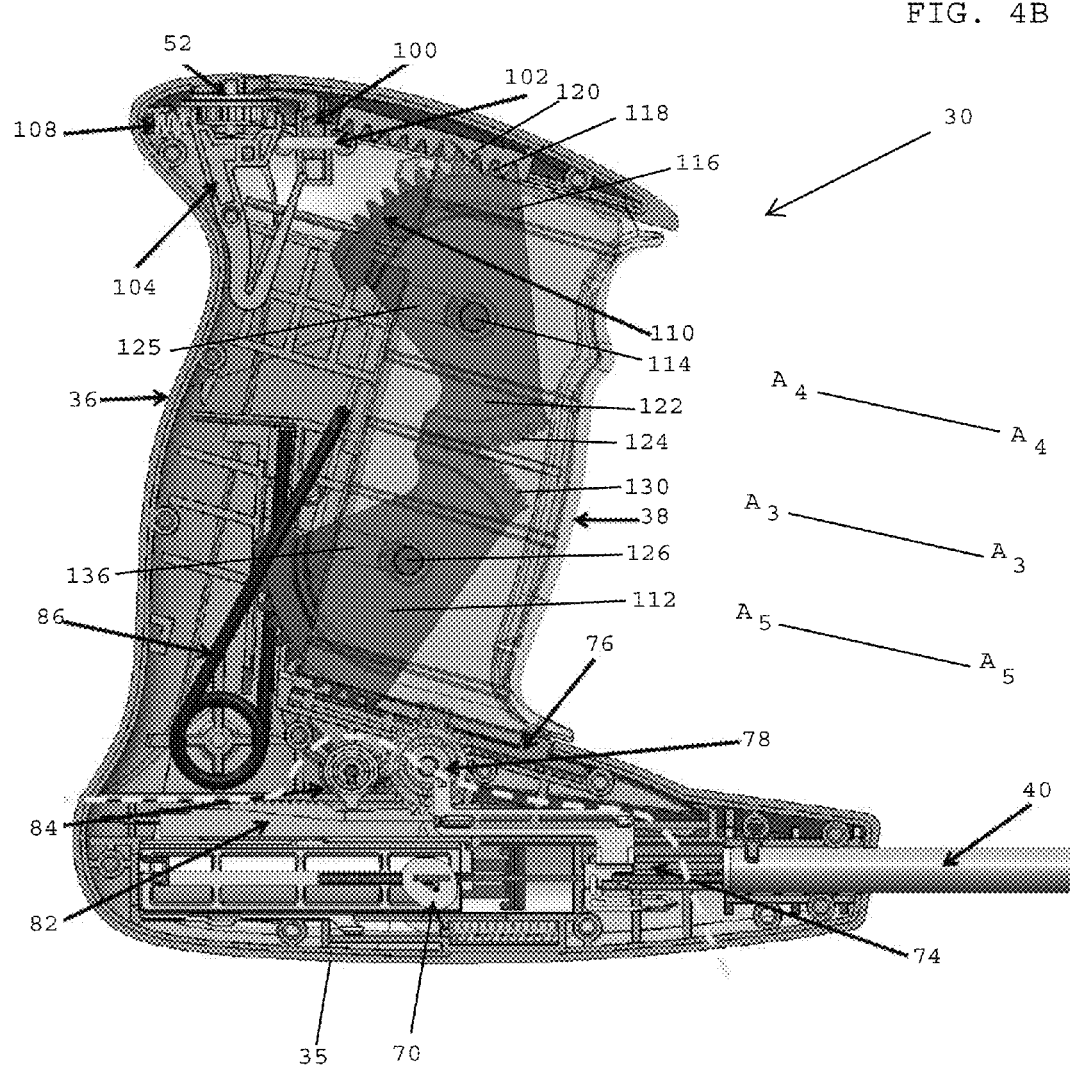
FIG. 4B shows the proximal end of the applicator instrument of FIG. 4A with a trigger and a two-step drive gear being transparent, in accordance with one embodiment of the present invention.

Referring to FIGS. 4A and 4B, in one embodiment, the applicator instrument 30 includes the housing 35 that contains a firing system, and a handle 36 projecting upwardly from the housing, whereby the handle has an upper end 50 that contains the counter 52. The handle includes the trigger 38 that is adapted to be pulled along a linear path toward the proximal end 32 of the applicator instrument 30. In one embodiment, the trigger 38 is adapted to move along a linear path $A_3$-$A_3$ that defines an angle $\alpha_2$ of about 10-20° and more preferably about 15° with the longitudinal axis $A_1$-$A_1$ of the applicator instrument 30.

In one embodiment, the applicator instrument 30 includes a firing system 70 having a spring block 72, a firing rod 74, and a firing spring that stores energy as the trigger 38 is squeezed. The firing system 70 preferably includes one or more features similar to those disclosed in commonly assigned U.S. Patent Application Publication Nos. US 2010/0292715, US 2010/0292712, US 2010/0292710, US 2010/0292713, and US 2011/079627, the disclosures of which are hereby incorporated by reference herein. The firing system 70 is desirably coupled with the trigger via a trigger rack 76 that slides proximally and distally with the trigger along the axis $A_3$-$A_3$. The trigger rack is coupled with a drive gear 78 that rotates in a counter-clockwise direction when the trigger 38 is squeezed toward the proximal end of the applicator instrument, and rotates in a clockwise direction when the trigger 38 is released and moves distally toward the distal end of the applicator instrument. The drive gear 78 has external gear teeth 80 that mesh with teeth provided at an upper end of a sliding yoke 82. As the drive gear 78 rotates in a counter-clockwise direction, the yoke 82 slides in a distal direction along the axis $A_1$-$A_1$. As the drive gear 78 rotates in a clockwise direction, the yoke 82 slides in a proximal direction along the axis $A_1$-$A_1$, preferably with a gear ratio of 0.9 to 1.5.

In one embodiment, the applicator instrument 30 includes a ratchet pawl 84 having a ratchet spring, which is similar to the subassembly disclosed in commonly assigned U.S. Patent Application Publication Nos. US 2010/0292715, US 2010/0292712, US 2010/0292710, US 2010/0292713, and US 2011/079627, the disclosures of which are hereby incorporated by reference herein. The ratchet pawl 84 ensures that the sliding yoke 82 moves to its distal-most position before it is able to change direction and move proximally back into the original position shown in FIG. 4A.

In one embodiment, the applicator instrument 30 includes a trigger return spring 86 that normally urges the trigger 38 to move distally. The trigger return spring 86 includes a first arm 88 that is secured within a molded portion of the handle 36, and a second arm 90 that preferably engages the trigger 38. In one embodiment, a proximal end of the trigger 38 has a tab 92 and the second arm 90 engages the tab for normally urging the trigger distally. The trigger return spring 86 preferably stores energy therein as the trigger 38 is squeezed and transfers the stored energy back to the trigger when the trigger is released for moving the trigger distally. In another embodiment, the trigger return spring 86 acts directly on the rotating links 110 and 112.

In one embodiment, the counter 52 includes a rotatable disc 94 having gear teeth 96. The counter 52 includes a window 98 that is formed in the upper end 50 the handle 36 to provide visual access to a top surface of the rotatable disc 94. The counter desirably includes a lock-out pin 100 and a lock-out pin spring (not shown) in contact with the lock-out pin. The applicator instrument desirably includes a lock-out pin cover 102 that partially covers a portion of the lock-out pin 100.

In one embodiment, the counter 52 has a lock-out counter 104 that is pivotally secured to the handle 36 via a lock-out counter pivot 106. The counter 52 also includes a lock-out counter spring 108 that normally urges the lock-out counter 104 to pivot toward the distal end of the applicator instrument 30. The lock-out counter 104 is adapted to toggle back and forth about the pivot 106 during each firing cycle.

FIG. 4B shows the applicator instrument 30 of FIG. 4A with the trigger being transparent for clearly showing a first rotating link 110 and a second rotating link 112 coupled with the trigger 38. In one embodiment, the first rotating link 110 is disposed inside the trigger 38 and is pivotally secured to the trigger 38 via a first pivot 114. The first rotating link 110 has an upper end 116 having upper gear teeth 118 that mesh with a rack 120 located inside the upper end of the handle 36. The first rotating link 110 has a lower end 122 having lower gear teeth 124. The trigger 38 includes a first internal slot 125 formed therein that is adapted to receive the first pivot 114 during assembly. Pivot 114 passes through a "snap fit" feature of the first internal slot 125 during assembly. This ensures that the two rotating links 110, 112 are pivotally secured.

The second rotating link 112 is pivotally secured to the trigger 38 via a second pivot 126. The second rotating link 112 has an upper end 128 with upper gear teeth 130 that mesh with the lower gear teeth 124 of the first rotating link 110. The first and second rotating links 110, 112 are coupled with one another via the opposing gear teeth 124, 130, which ensure that the first and second rotating links 110, 112 rotate at the same rate. The second rotating link 112 has a lower end 132 having bottom teeth 134 that mesh with opposing teeth molded into a second rack disposed above the housing 35 (not shown). The trigger 38 includes a second molded slot 136 that receives the second pivot 126 during assembly. Pivot 114 passes through a "snap fit" feature of internal slot 136 during assembly. This ensures that the two rotating links 110, 112 are pivotally secured. Further, the rotating gear links 110, 112 have paired offset teeth 124, 130 to allow synchronized timing between two gears made from the same mold.

The configuration of the first and second rotating links 110, 112 within the handle 36, and the pivotal connection of the first and second rotating links with the trigger 38 enables the trigger 38 to move along a single linear path, namely axis $A_3$-$A_3$. The linear motion of the trigger 38 allows the force and distance required to squeeze the trigger to remain consistent no matter where the squeezing forces are concentrated along the length of the trigger, which minimizes the likelihood of binding of the trigger.

Referring to FIG. 4C, in one embodiment, the trigger return spring 86 normally urges the trigger 38 to move distally. The trigger return spring 86 has the first arm 88 secured within a molded portion of the handle 36 and the second arm 90 that engages a tab 92 at a proximal face of the trigger 38. As the trigger is pulled toward the proximal end 32 of the applicator instrument 30, the tab 92 urges the second arm 90 of the trigger return spring 86 to move proximally for storing energy in the spring 86. After the trigger 38 has been pulled to its most-proximal position for dispensing a surgical fastener, the trigger 38 may be released, whereupon the second arm 90 of the spring 86 urges the trigger 38 to move distally for returning the trigger to the original position shown in FIG. 4C.

In one embodiment, the housing 35 and the handle 36 includes left and right halves that are assembled together. In one embodiment, the handle halves are assembled together with press fit pins. In one embodiment, the trigger 38 is captured between the left and right halves of the housing and the handle. In one embodiment, the trigger 38 travels in distal and proximal directions along a linear path having a total length of about 0.9 inches. The applicator instrument preferably has physical stops at the proximal and distal ends of the linear path of travel of the trigger rack 76 that halt the proximal and distal movement of the trigger along the linear path $A_3$-$A_3$. In one embodiment, the left and right halves are desirably made from a polymer such as glass reinforced polycarbonate. In one embodiment, the trigger is made of a polymer material such as a glass reinforced polycarbonate.

In one embodiment, the housing 35 contains a firing system having the firing spring, a spring block and a firing rod, as disclosed in commonly assigned U.S. Patent Applicant Publication Nos. US 2010/0292715, US 2010/0292712, US 2010/0292710, US 2010/0292713, and US 2011/079627, the disclosures of which are hereby incorporated by reference herein. The spring block 72 and the firing rod 74 are adapted to move in distal and proximal directions along the longitudinal axis $A_1$-$A_1$.

Referring to FIG. 4C, in one embodiment, the trigger 38 is connected with the trigger rack 76 by means of a tab extending from the trigger 38 that protrudes between two bosses on the trigger rack 76. In one embodiment, the tolerance of the fit between the trigger tab and the trigger rack bosses is precise and close to allow minimal free play between the trigger and the trigger rack. The existence of two separate trigger parts allows for a stronger material (e.g., metal such as stainless steel) to be used for the trigger rack 76. In addition, the separation of the trigger tab from the trigger rack ensures that any rotational forces exerted by the user on the trigger 38 are limited to the trigger and are not exerted upon the trigger rack 76. In one embodiment, the trigger rack 76 is captured between the left and right handle halves and is in contact with the drive gear 78. The trigger rack 76 is adapted to slide along an axis that is parallel with the axis of movement $A_3$-$A_3$ of the trigger 38. In one embodiment, the trigger rack travel is limited to about 0.9 inches, with both distal and proximal stopping features being located within the left handle half. In one embodiment, the trigger rack has trigger rack gear teeth provided at an underside thereof. The drive gear 78 has two sets of gear teeth of differing radii to provide a two-step gear, and the trigger rack gear teeth engage the smaller of the gears of the drive gear 78.

The rotating links 110, 112 pivot about the respective first and second pivots 114, 126 protruding into opposing through holes in the trigger 38. The rotating links 110, 112 are preferably captured by and restricted in their rotational motion by features of the trigger. The rotating links are coupled to each other via paired opposing gear teeth 124, 130 positioned near the middle of the hand-squeezing area of the trigger 38. In one embodiment, these matching gear teeth 124, 130 have a face width of approximately 0.1 inch, and a pitch diameter of about 0.875 inches. These dimensions and features allow the first and second rotating links 110, 112 to mirror each other during movement. The first and second rotating links 110, 112 also have outer gear teeth 118, 134, respectively, with a face of about 0.1 inch and a pitch diameter that is about 1.042 inches. These outer gear teeth 118, 134 desirably mate with corresponding opposing rack gear features formed in the handle halves, one in the right handle half, and one in the left handle half.

The engagement and timing of the gear features for the first and second rotating links 110, 112 enables the trigger 38 to move in a linear fashion along the axis $A_3$-$A_3$, and also prevents the trigger from rotating about a center point when squeezing forces are applied unevenly along the hand-squeezing area of the trigger. The ability of the trigger mechanism to convert linear motion of the trigger into rotary motion through the drive gear 78 minimizes friction and any risk of binding. In one embodiment, the first and second rotating links 110, 112 are preferably made from a polymer such as a glass reinforced polycarbonate.

In one embodiment, the drive gear 78 desirably connects the trigger rack 76 to the yoke 82 of the firing system 70. The yoke 82 and the firing system 70 are preferably similar to that disclosed in the firing system of commonly assigned U.S. Patent Application Publication Nos. US 2010/0292715, US 2010/0292712, US 2010/0292710, US 2010/0292713, and US 2011/079627, the disclosures of which are hereby incorporated by reference herein. The drive gear preferably transfers the motion of the trigger along axis $A_3$-$A_3$ to the motion of the yoke along the axis $A_1$-$A_1$. In one embodiment, these two axes differ by about 15° such that proximal movement of the trigger 38 along axis $A_3$-$A_3$ results in distal movement of the yoke 82 along axis $A_1$-$A_1$. In one embodiment, the drive gear 78 has a gear ratio that results in 0.9 inches of trigger travel producing 1.5 inches of yoke travel. In one embodiment, the two-step drive gear 78 is preferably made of a metal such stainless steel. The gear may be mounted on a metal pin for rotating about the metal pin. In one embodiment, the pin about which the drive gear 78 rotates is located and constrained between the left and right handle halves.

In one embodiment, the trigger return spring 86 is positioned inside the handle so that the coils of the spring 86 are captured over a post that extends between the left and right handle halves. A first arm of the trigger return spring is fixed relative to the handle halves and is captured within a pocket, preferably formed within the left handle half. A second or moving arm of the trigger return spring, desirably has an L bend at its distal end, and is biased against the trigger such that the trigger is urged toward a forward distal position. The trigger return spring 86 desirably exerts a force upon the trigger that is about two pounds pre-loaded and nine pounds under final load. In one preferred embodiment, the trigger return spring 86 provides a force of about five pounds pre-loaded and seven pounds final load. In one embodiment, the trigger return spring 86 is desirably made of metal such as stainless steel.

Figure 5A:
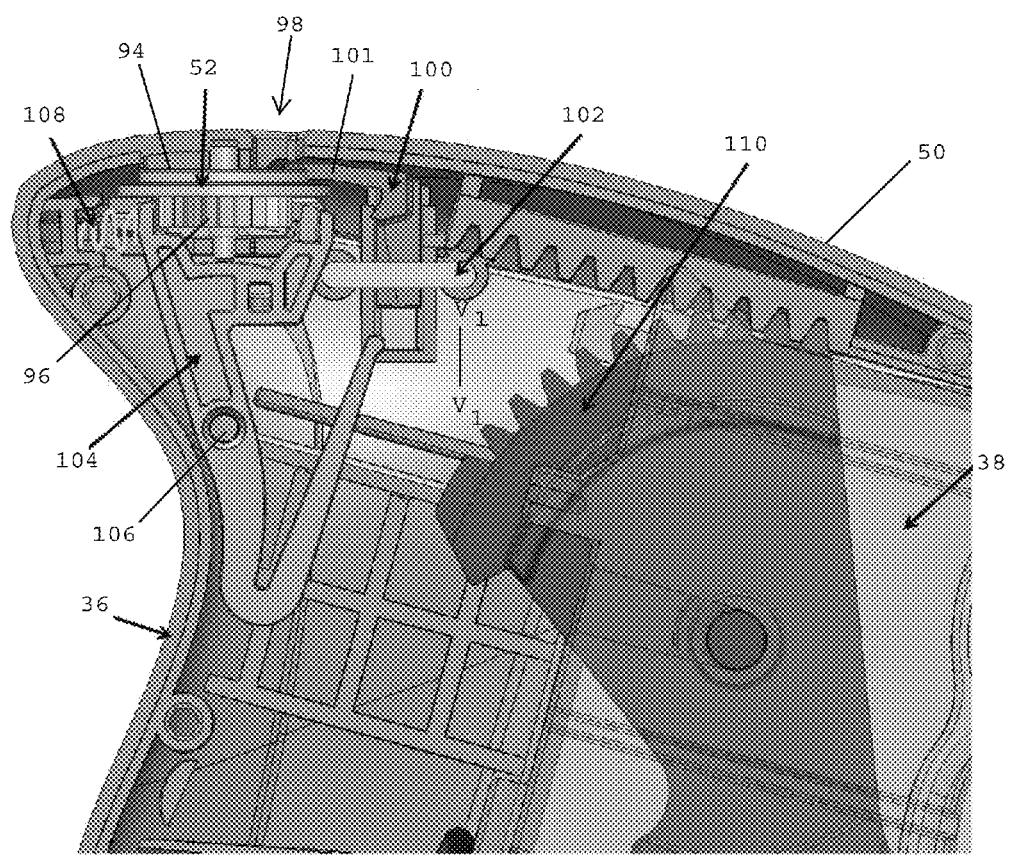
FIGS. 5A-5C show a counter for counting how many surgical fasteners have been dispensed from an applicator instrument for dispensing surgical fasteners, in accordance with one embodiment of the present invention.
Figure 5B:
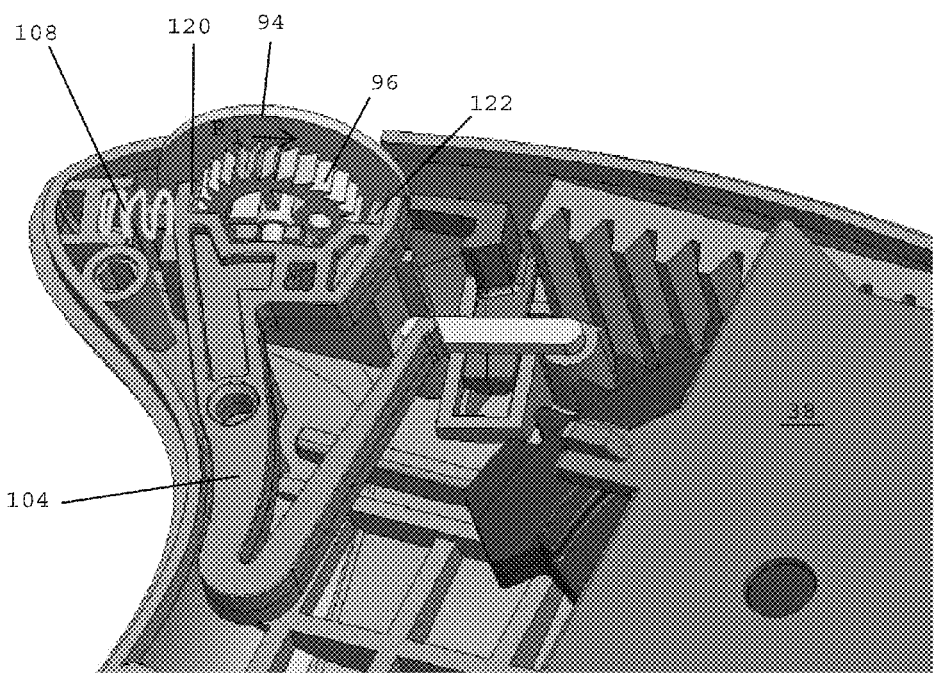
Figure 5C:
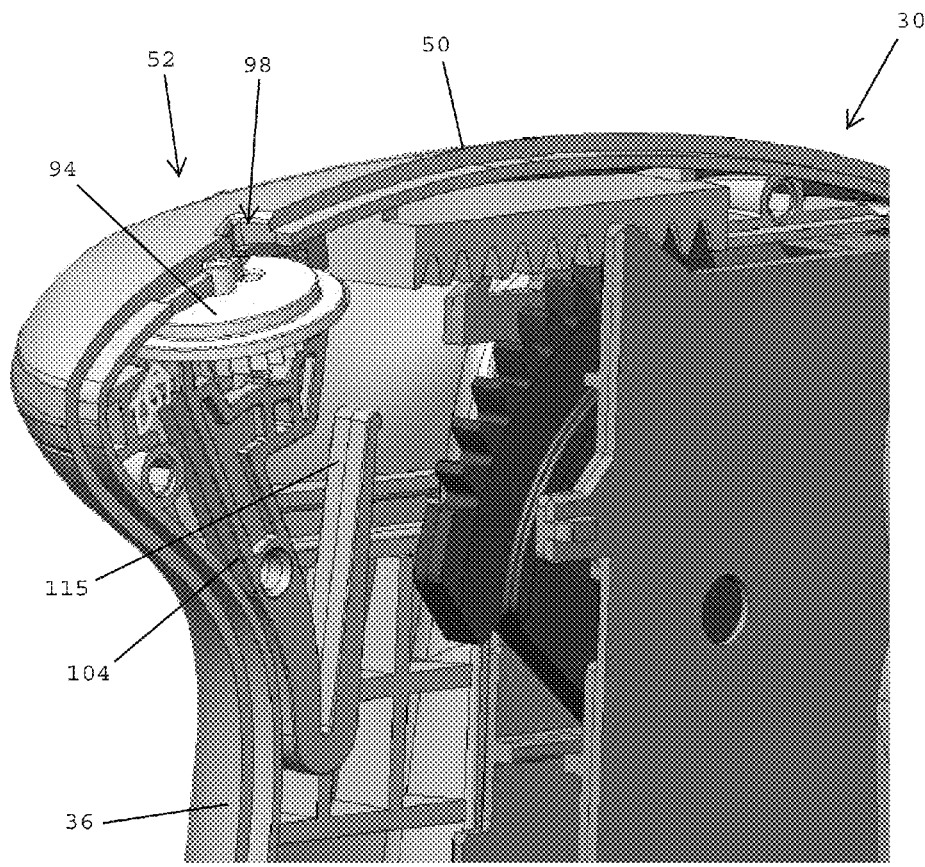

Referring to FIGS. 5A-5C, in one embodiment, the applicator instrument 30 includes the counter 52 having the rotatable disc 94 and the gear teeth 96 projecting below the rotatable disc 94. A window 98 is formed in the upper end 50 of the handle 36 to provide visual access to the top surface of the rotatable disc 94. The counter 52 includes a lock-out pin 100 that is adapted to drop along the axis $V_1$-$V_1$ (FIG. 5A) when a slot formed in the rotatable disc 94 has been rotated into alignment with an extension arm 101 of the lock-out pin 100. The counter 52 also includes a lock-out pin cover 102 that extends over a portion of the lock-out pin 100.

In one embodiment, the counter 52 has a lock-out counter 104 that is pivotally secured to the left handle half via a pivot point 106. A lock-out counter spring 108 normally urges the upper end of the lock-out counter 104 to pivot toward the distal end of the applicator instrument 30. The lock-out counter 104 toggles back and forth during a firing cycle for rotating the rotatable disc 94 one position to indicate that one surgical fastener has been fired. The rotatable disc 94 is adapted to be rotated one additional position each time another surgical fastener is dispensed. In one embodiment, the lock-out counter 104 has a flexible cantilever beam 115 that is engaged by the first rotating link 110 for toggling the lock-out counter 104 from the forward position to the rear position.

Referring to FIG. 5B, the lock-out counter 104 has a proximal tooth 120 and a distal tooth 122 that are adapted to engage the gear teeth 96 projecting below the rotatable disc 94. In one embodiment, as the lock-out counter 104 pivots distally, the proximal tooth 122 engages the gear teeth 96 for rotating the disc 94 one half of a position in the direction indicated $R_1$. In one embodiment, when the trigger 38 (FIG. 5A) is fully squeezed, the trigger contacts the lock-out counter 104 for pivoting the upper end of the lock-out counter in a proximal direction so that the distal tooth 122 engages the gear 96. When the trigger 38 is released and moves distally, the lock-out counter spring 108 pivots the upper end of the lock-out counter 104 in a distal direction so that the proximal tooth 120 engages the gear teeth 96 for rotating the disc 94 one half of a position in the direction $R_1$. In one embodiment, the rotatable disc 94 is rotated one position (indicating that one surgical fastener has been fired) each time the upper end of the lock-out counter 104 pivots proximally and then distally to the initial position shown in FIG. 5B. In one embodiment, when the last surgical fastener has been dispensed, the lock-out pin 100 drops for locking the trigger 38 in a proximal position.

FIG. 5C shows the window 98 formed at the upper end 50 of the handle 36. The window 98 provides visual access to the top surface of the rotatable disc 94 to provide an indication of how many surgical fasteners have been fired and/or how many surgical fasteners remain in the applicator instrument 30.

In one embodiment, the counter and lock-out assembly disclosed herein is generally similar to the structure disclosed in commonly assigned U.S. Patent Application Publication Nos. US 2010/0292715, US 2010/0292712, US 2010/0292710, US 2010/0292713, and US 2011/079627, the disclosures of which are hereby incorporated by reference herein.

In one embodiment, the lock-out pin spring and the lock-out counter spring are desirably made of a metal such as stainless steel. The components of the counter 52 are preferably made of polymer materials such as acetal, ABS, glass reinforced acetal, or combinations thereof.

Figure 6A:
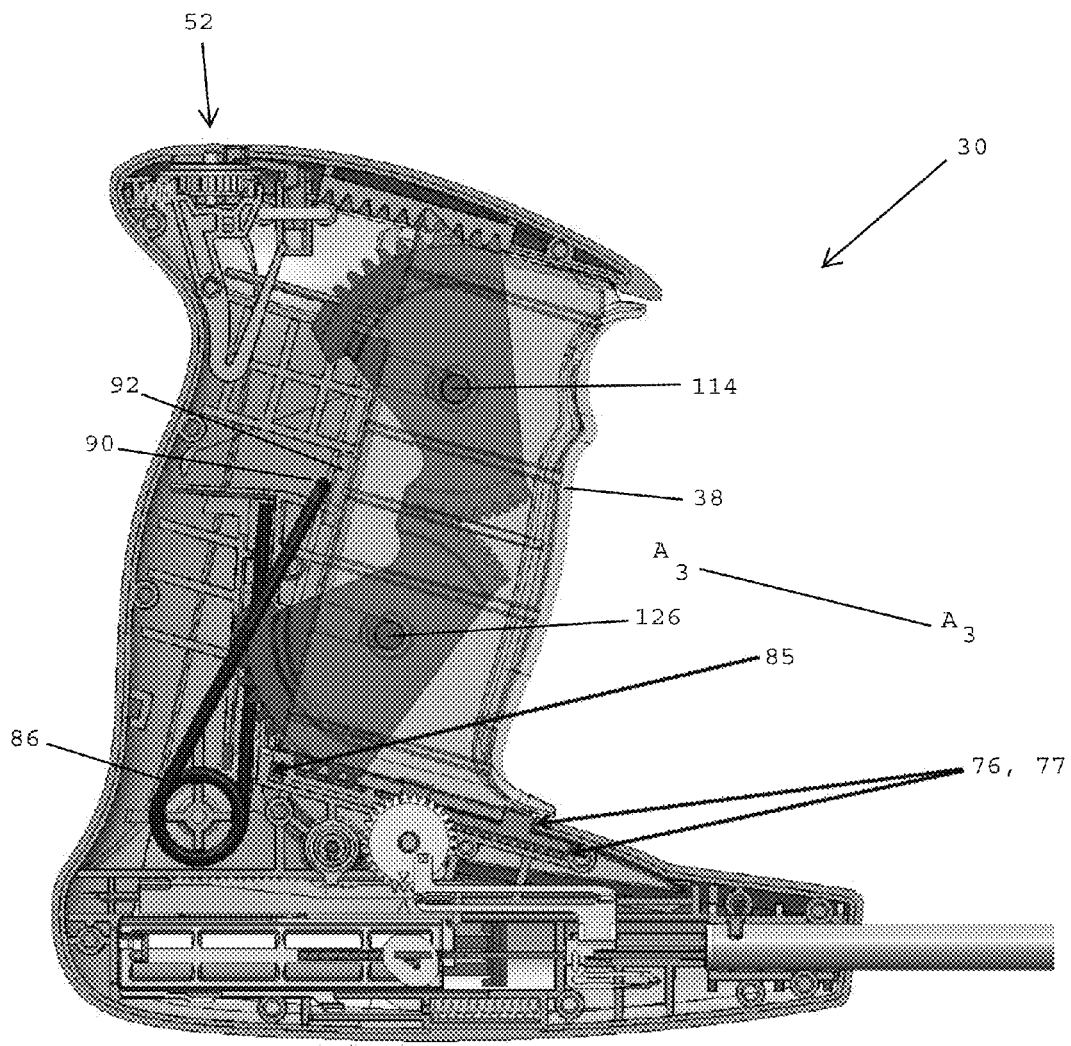
FIG. 6A shows an applicator instrument during a first stage of a firing cycle, in accordance with one embodiment of the present invention.
Figures 1, 6A:
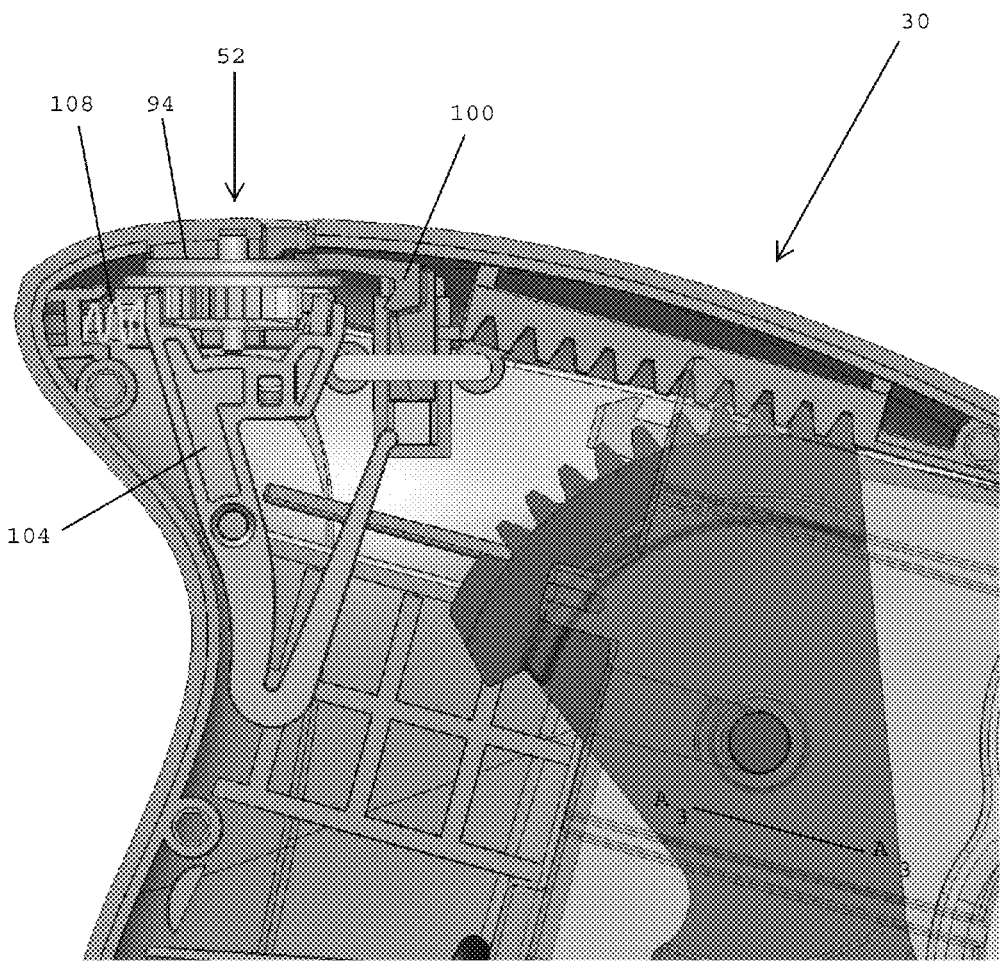

FIGS. 6A and 6A-1 show the applicator instrument 30 including the position of the trigger 38 and the counter 52 at the beginning of a firing cycle, which is also referred to herein as the first stage of the firing cycle. In FIG. 6A, the second arm 90 of the trigger return spring 86 rests against the tab 92 of the trigger 38 to provide a pre-load force that biases the trigger distally. The trigger 38 is constrained to move along the linear path of axis $A_3$-$A_3$ by the pivots 114, 126 and the trigger rack 76. In turn, the trigger rack 76 is constrained from distal movement by the distal stop 77 formed in the left handle half. Referring to FIG. 6A-1, at the beginning of the firing cycle, the lock-out counter 104 of the counter 52 is pivoted distally by the lock-out counter spring 108. The lock-out pin 100 is held up by the rotatable disc 94.

Figure 6B:
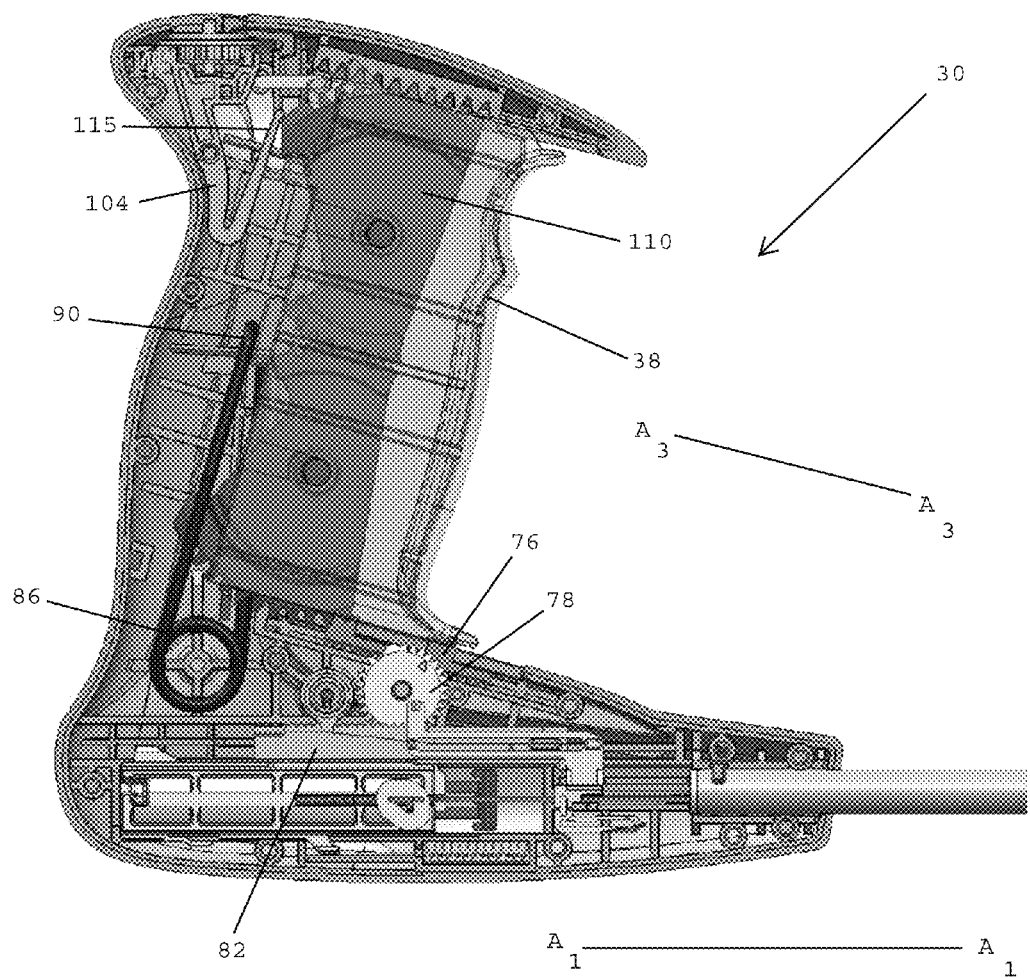
FIG. 6B shows an applicator during a second stage of a firing cycle, in accordance with one embodiment of the present invention.
Figures 1, 6B:
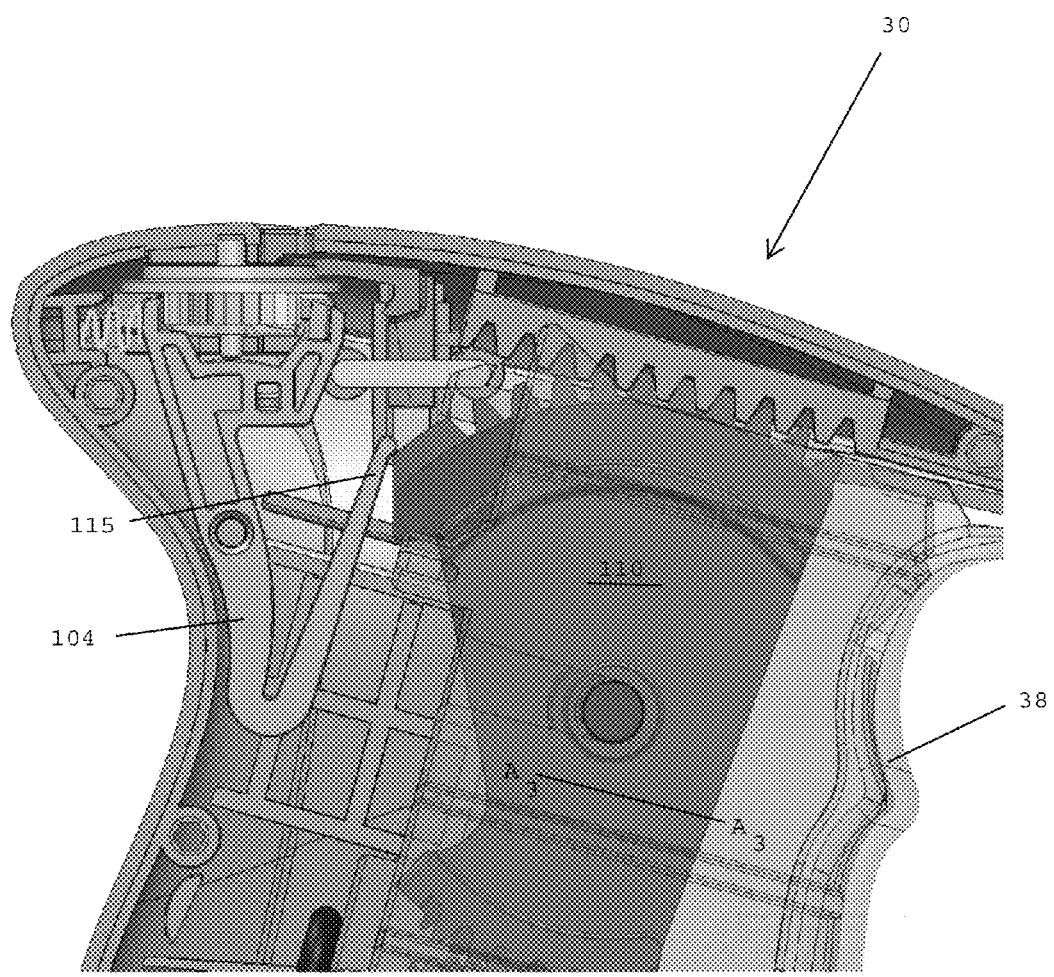

FIGS. 6B and 6B-1 show the applicator instrument 30 during a second stage of a firing cycle. The trigger 38 has been partially squeezed so that the trigger 38 and the trigger rack 76 have moved proximally about 0.486 inches from the start position shown in FIGS. 6A and 6A-1. The first rotating link 110 has made initial contact with the dwell beam 115 of the lock-out counter 104. The second arm 90 of the trigger return spring 86 has flexed proximally for increasing the spring force against the trigger 38. The proximal movement of the trigger rack 76 along axis $A_3$-$A_3$ rotates the drive gear 78 in a counter-clockwise direction, which, in turn, advances the yoke 82 distally along the axis $A_1$-$A_1$ for advancing the firing rod and storing energy in the firing spring of the firing system, as disclosed in commonly assigned U.S. Patent Application Publication Nos. US 2010/0292715, US 2010/0292712, US 2010/0292710, US 2010/0292713, and US 2011/079627, the disclosures of which are hereby incorporated by reference herein.

Figure 6C:
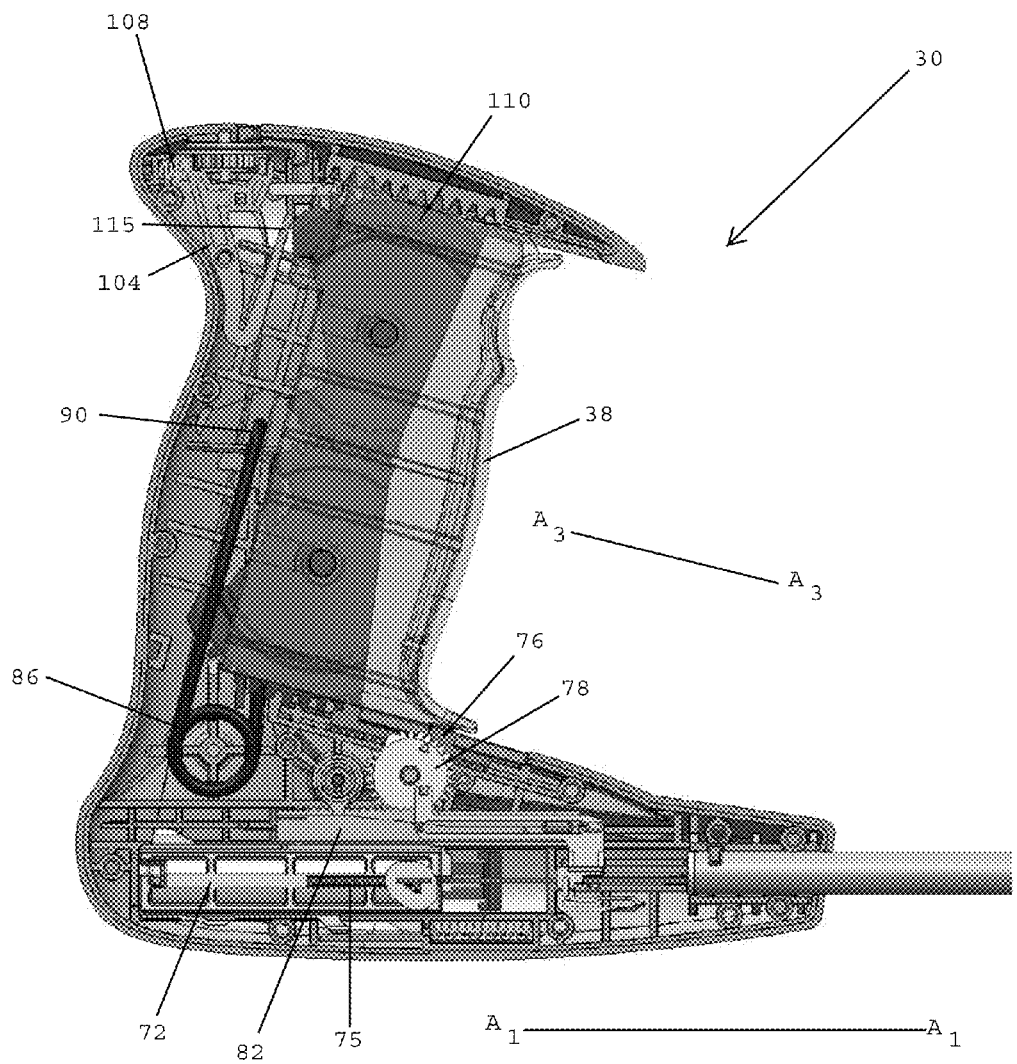
FIG. 6C shows an applicator during a third stage of a firing cycle, in accordance with one embodiment of the present invention.
Figures 1, 6C:
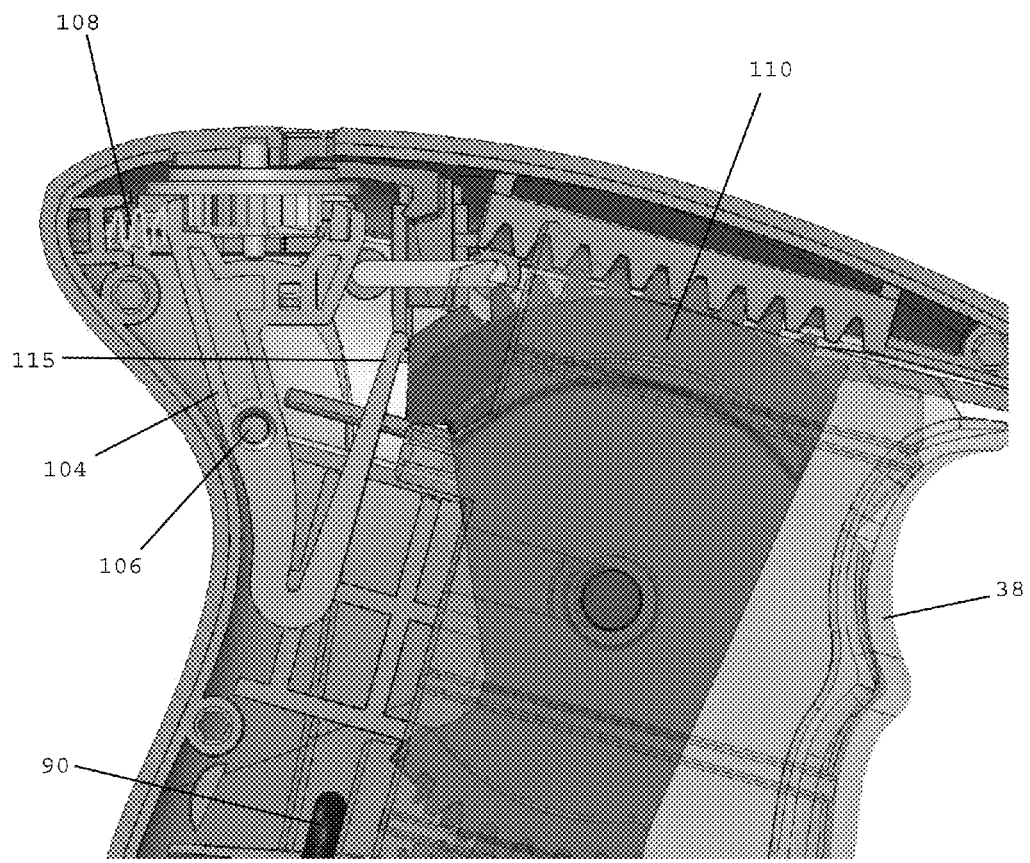

FIGS. 6C and 6C-1 show the applicator instrument 30 during a third stage of the firing cycle. The trigger 38 and the trigger rack 76 have moved proximally about 0.537 inches from the beginning the firing cycle (see FIG. 6A) due to continued squeezing of the trigger 38. Further proximal movement of the trigger rack 76 along the axis $A_3$-$A_3$ results in further rotation of the drive gear 78, which causes corresponding distal movement of the yoke 82 along the axis $A_1$-$A_1$. As the yoke 82 moves distally, energy may be stored in a firing spring located inside the spring block 72. The second arm 90 of the trigger return spring 86 has been further flexed proximally for increasing the return force against the trigger 38. During the third stage, the first rotating link 110 deflects the dwell beam 115 of the lock-out counter 104 proximally by about 0.029 inches. The force applied to the dwell beam 115 by the first rotating link 110 is in equilibrium with the counter force provided by the lock-out counter spring 108, so that the lock-out counter 104 is "primed" for toggling from the forward position shown in FIG. 6C-1 to a rear position.

Figure 6D:
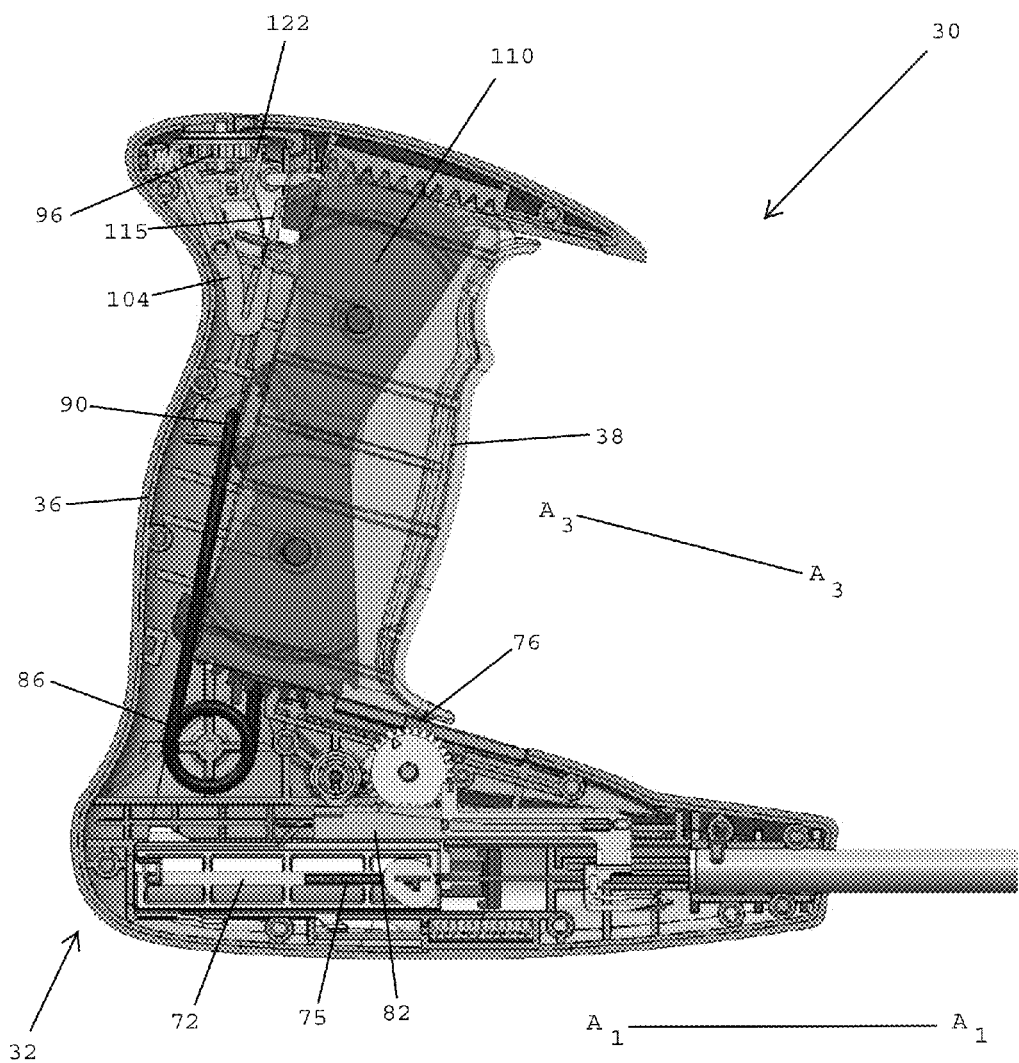
FIG. 6D shows an applicator during a fourth stage of a firing cycle, in accordance with one embodiment of the present invention.
Figures 1, 6D:
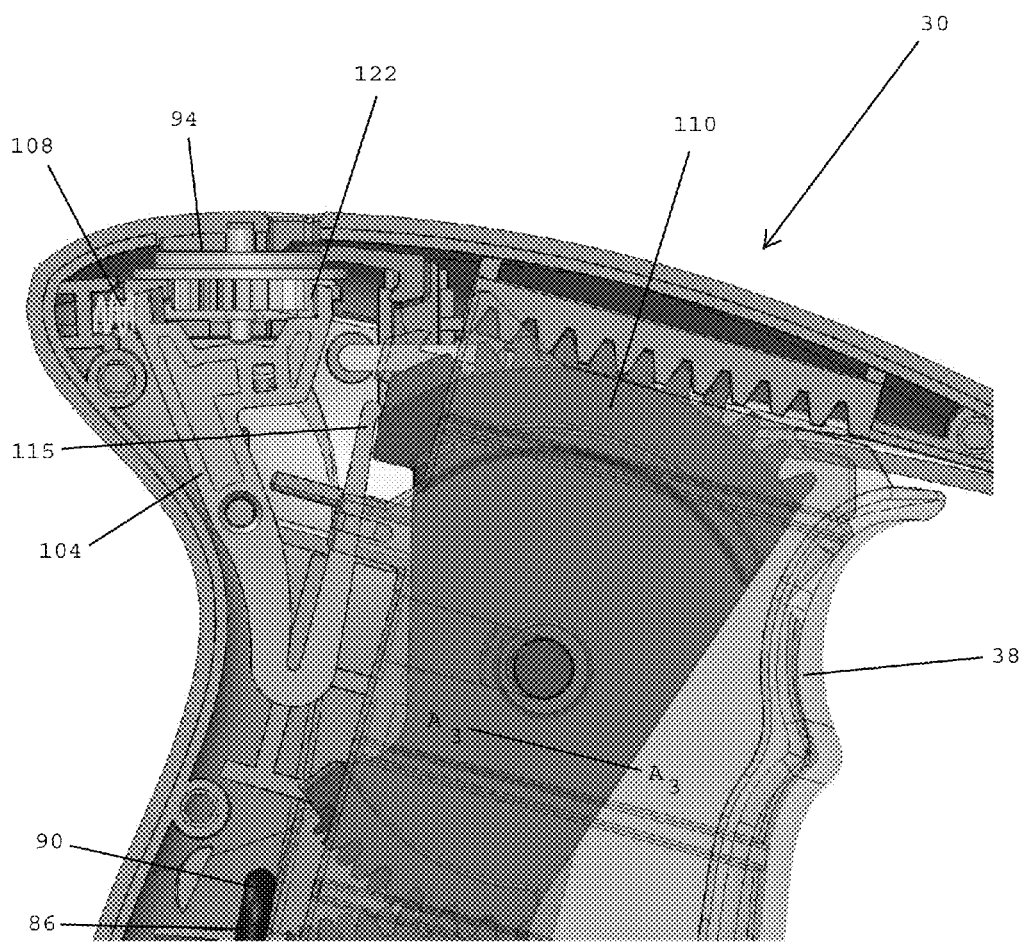

FIGS. 6D and 6D-1 show the applicator instrument 30 during a fourth stage of the firing cycle. The trigger 38 and the trigger rack 76 have moved proximally about 0.716 inches due to continued squeezing of the trigger 38. The second arm 90 of the trigger return spring 86 has further flexed proximally for increasing the return force against the trigger 38. Linear movement of the trigger rack 76 in a proximal direction along the axis $A_3$-$A_3$ results in continued counter-clockwise rotation of the drive gear 78, which causes corresponding distal sliding motion of the yoke 82 along the axis $A_1$-$A_1$ toward the distal end of the applicator instrument 30, and storing additional energy in the firing spring 75 inside the spring block 72. The first rotating link 110 has deflected the dwell beam 115 of the lock-out counter 104 by about 0.044 inches. At this point, the rearward force applied to the dwell beam 115 of the lock-out counter 104 has overcome the counter force provided by the lock-out counter spring 108 so that the upper end of the lock-counter 104 is biased proximally into the rear position. When the lock-out counter 104 toggles to the rear position, the distal tooth 122 engages the gear 96 for rotating the rotatable disc 94 by one-half tooth of the gear 96.

Figure 6E:
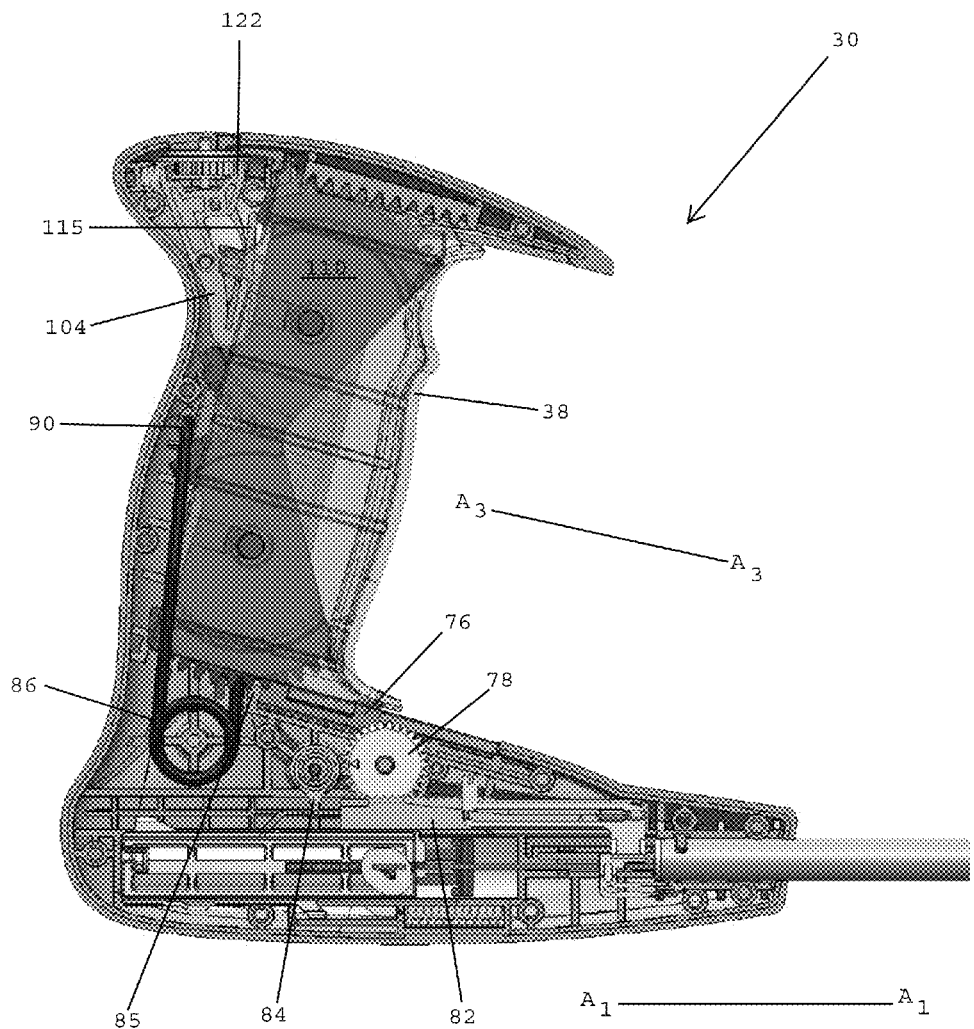
FIG. 6E shows an applicator during a fifth stage of a firing cycle, in accordance with one embodiment of the present invention.
Figures 1, 6E:
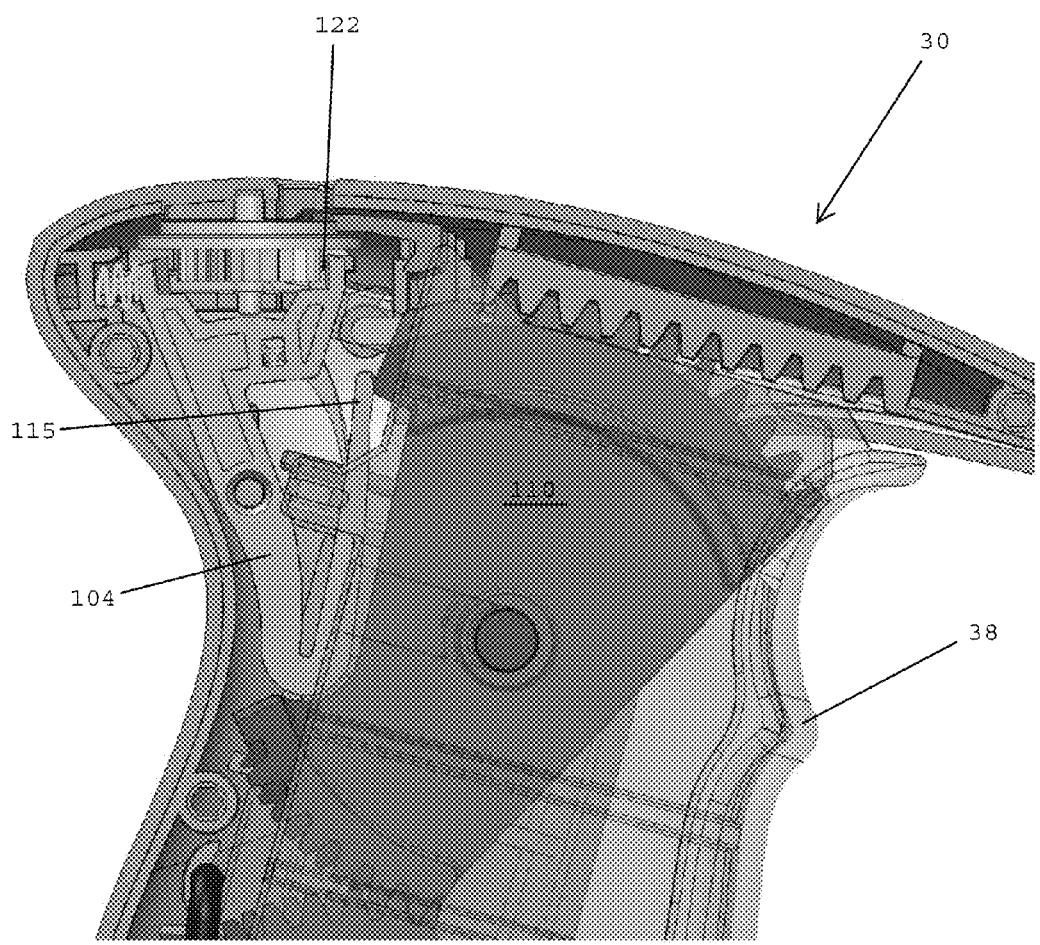

FIGS. 6E and 6E-1 show the applicator instrument 30 during a fifth stage of the firing cycle. The trigger 38 and the trigger rack 76 have moved proximally about 0.900 inches from the commencement of the firing cycle (FIG. 6A) due to continued squeezing of the trigger. The proximal sliding movement of the trigger rack 76 is halted by a proximal stop 85 (FIG. 6A) molded into the handle 36. At this stage, the trigger rack 76 has contacted the proximal stop 85 and the proximal movement of the trigger 38 and the trigger rack 76 is complete. The second arm 90 of the trigger return spring 86 has flexed further for increasing the return force against the trigger 38 to a peak value. Proximal movement of the trigger rack 76 along axis $A_3$-$A_3$ has resulted in continued rotation of the drive gear 78, which, in turn, causes distal movement of the yoke 82 along axis $A_1$-$A_1$ as described in commonly assigned U.S. Patent Application Publication Nos. US 2010/0292715, US 2010/0292712, US 2010/0292710, US 2010/0292713, and US 2011/079627, the disclosures of which are hereby incorporated by reference herein. Before the end of stage five, the firing rod is released and the energy in the firing spring is transferred to the firing rod to move the firing rod distally for dispensing a surgical fastener. The first rotating link 110 has deflected the dwell beam 115 of the lock-out counter 104 by about 0.115 inches. The upper end of the lock-out counter 104 remains toggled over to the rear position whereby the distal tooth 122 contacts the gear 96.

During the fifth stage of the firing cycle shown in FIG. 6E, the trigger 38 has been fully squeezed and the drive gear 78 has advanced the proximal end of the yoke 82 distally beyond the ratchet pawl 84. With the proximal end of the yoke 82 clear of the ratchet pawl 84, the ratchet pawl may re-set so that the yoke 82 is free to once more slide toward the proximal end 32 of the applicator instrument 30 for commencing another firing cycle.

In one embodiment, when the trigger 38 is released, the energy stored in the trigger return spring 86 is transferred to the trigger 38 for urging the trigger to move in a distal direction along the axis $A_3$-$A_3$ for returning the trigger to the initial trigger position shown in FIG. 6A. Corresponding resetting actions of the yoke 82 and the firing system 70 are similar to the movements disclosed in commonly assigned U.S. Patent Application Publication Nos. US 2010/0292715, US 2010/0292712, US 2010/0292710, US 2010/0292713, and US 2011/079627, the disclosures of which are hereby incorporated by reference herein.

When the trigger 38 is released, the first rotating link 110 moves distally for removing a compression force on the dwell beam 115 of the lock-out counter 104. The lock-out return spring 108 preferably toggles the upper end of the lock-out counter 104 in a distal direction and back to the forward position shown in FIG. 6A-1. The back and forth toggling of the lock-out counter 104 will result in incremental rotation of the rotatable disc 94 of the counter 52.

Figure 7A:
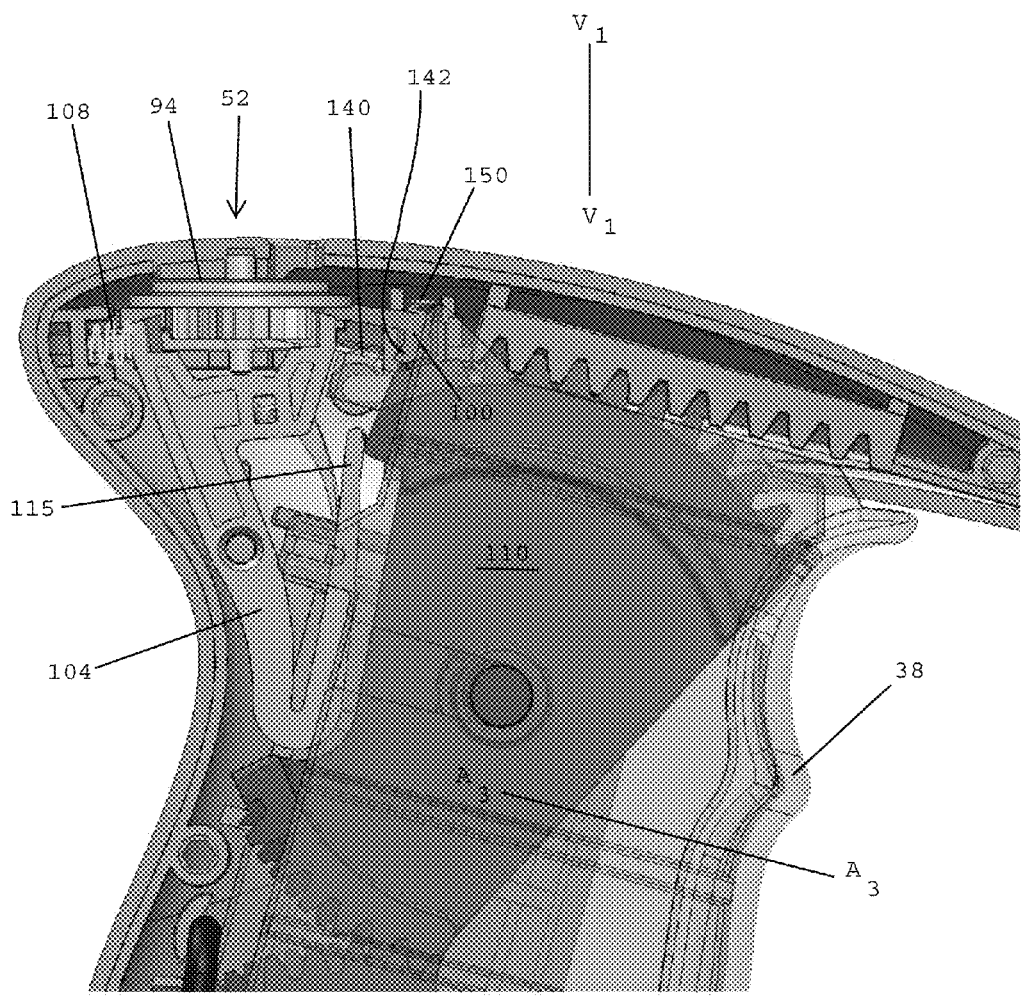
FIGS. 7A-7C show the movement of the counter of FIGS. 5A-5C during delivery of the last surgical fastener, in accordance with one embodiment of the present invention.

In one embodiment, the counter 52 locks the trigger in a proximal position (FIG. 6E) when the last surgical fastener has been fired. Referring to FIG. 7A, in one embodiment, the trigger 38 has a hook 140 projecting from a proximal end thereof. The hook 140 moves simultaneously with the trigger 38 as the trigger moves in proximal and distal directions along the axis $A_3$-$A_3$. In FIG. 7A, the trigger hook 140 is proximal to the lock-out pin hook 142.

The lock-out pin 100 has a lock-out pin hook 142 that is adapted to engage the trigger hook 140 when the last surgical fastener has been fired. In FIG. 7A, a radial slot provided in the rotatable disc 94 is aligned with the arm 101 of the lock-out pin 100. As a result, the lock-out pin 100 is free to fall toward the bottom of the applicator instrument along the axis $V_1$-$V_1$. The lock-out pin 100 is urged downward by a lock-out pin spring 150. The dwell beam 115 of the lock-out counter 104 ensures that the lock-out pin 100 drops before the trigger hook 140 passes beyond the lock-out pin hook 142. As the trigger 38 is pulled proximally, a ramp feature on the leading edge of the trigger hook 140 deflects the lock-out pin 100 upward along the axis $V_1$-$V_1$.

Figure 7B:
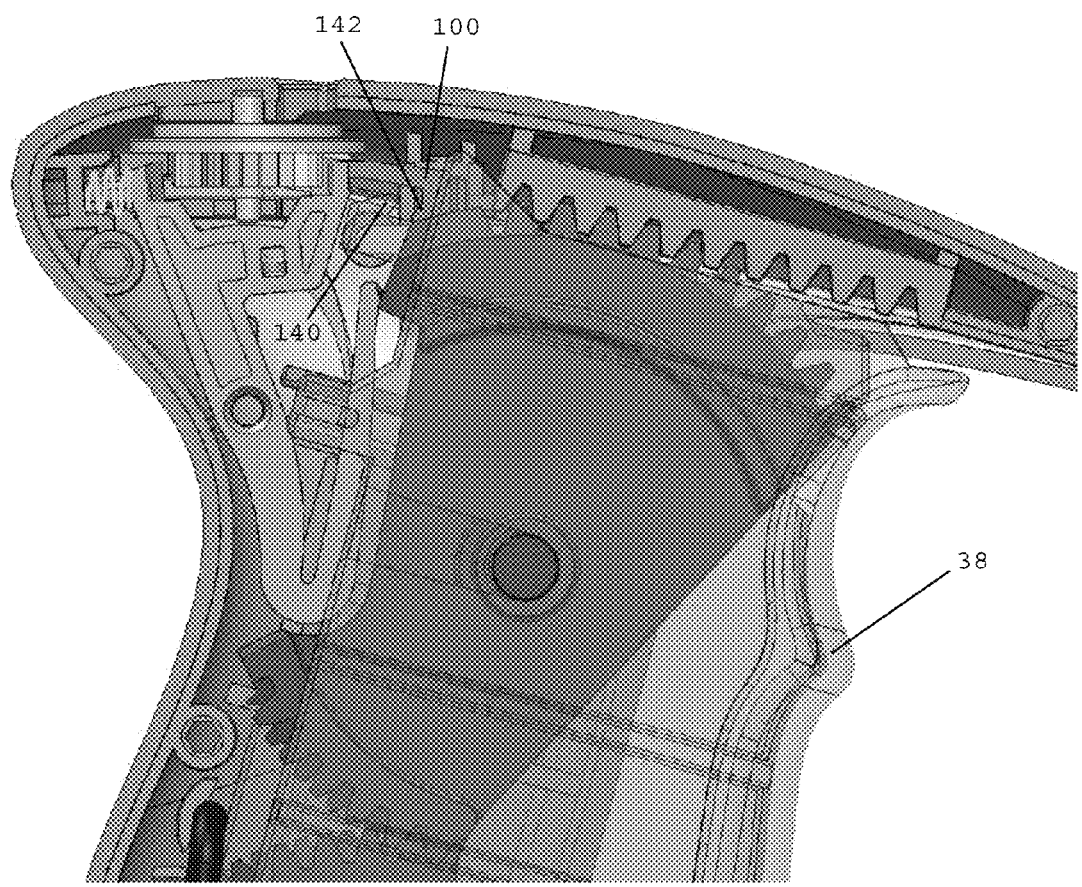
Figure 7C:
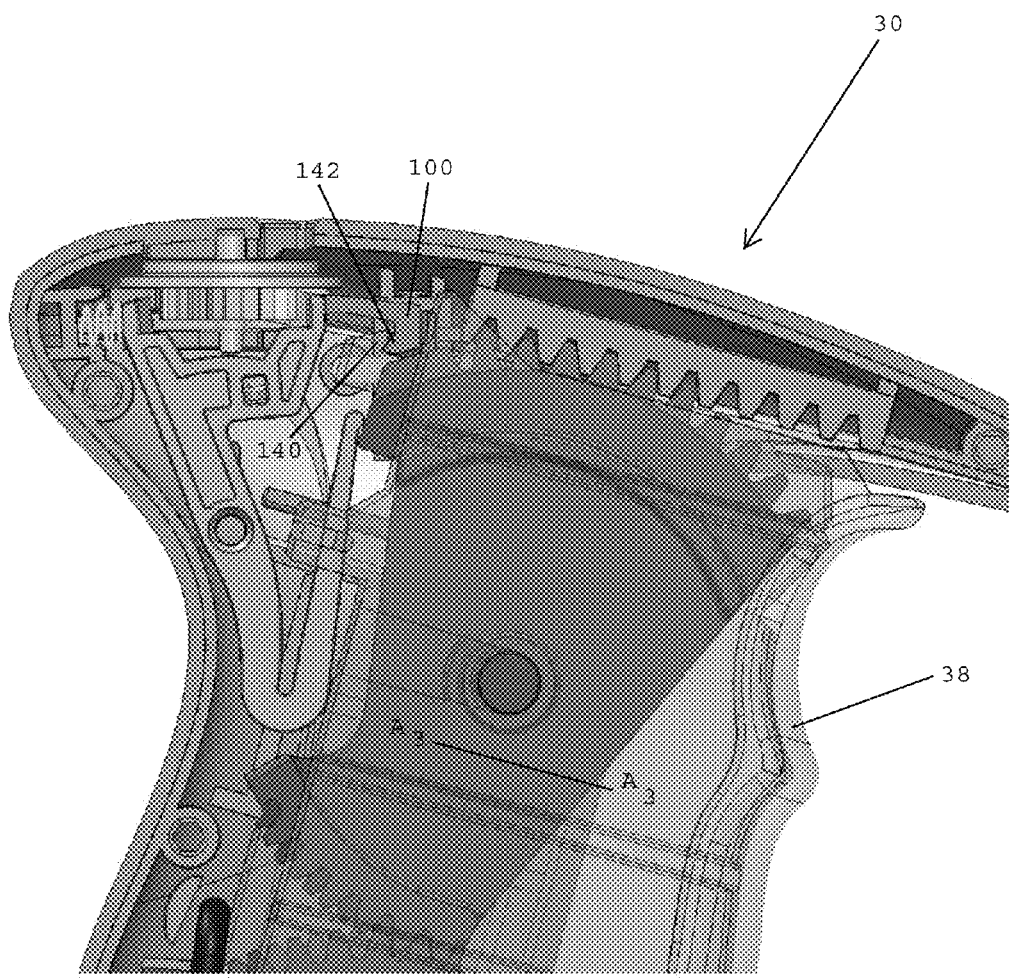

Referring to FIG. 7B, as the trigger continues to travel proximally, the lock-out pin 100 eventually drops again so that the hook 142 of the lock-out pin 100 is distal to the hook 140 connected with the trigger 38. Referring to FIG. 7C, when the trigger 38 is released, the trigger return spring 86 urges the trigger distally until the lock-out pin hook 142 engages the trigger hook 140 to halt the trigger 38 from moving further distally along the axis $A_3$-$A_3$. As a result, the trigger 38 is locked in the position shown in FIG. 7C and the applicator instrument 30 may no longer be used for dispensing surgical fasteners.

Figure 8:
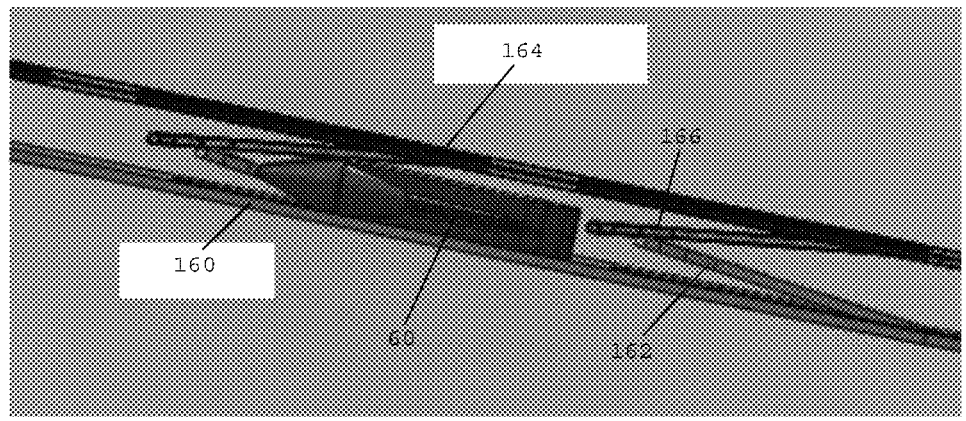
FIG. 8 shows a side elevation view of an advancer element that cycles back and forth for advancing surgical fasteners toward a distal end of an applicator instrument and an anti-backup member for preventing the surgical fasteners from moving proximally, in accordance with one embodiment of the present invention.

Referring to FIG. 8, in one embodiment, the firing system preferably includes an advancer element 160 having advancer element tabs 162 and an anti-backup member 164 having anti-backup tabs 166. During a complete firing cycle of the applicator instrument disclosed herein, the advancer element 160 cycles distally and proximally for advancing surgical fasteners 60 one segment toward the distal end of the applicator instrument. In one embodiment, when the trigger 38 (FIG. 1) is squeezed, the advancer element 160 moves distally (to the left in FIG. 8) whereupon the advancer element tab 162 abuts against a rear of the surgical fastener 60 for advancing the surgical fastener in a distal direction. When the trigger is released and moves distally for returning to the initial position, the advancer element 160 moves in a proximal direction toward the proximal end of the applicator instrument. The anti-backup tabs 166 prevent the surgical fasteners from moving proximally as the advancer element moves proximally. The advancer element 160 moves distally each time the trigger is squeezed and moves proximally when the trigger is released for returning to a start position at the beginning of a firing cycle. The anti-backup member 164 remains stationary during the firing cycles. The anti-backup tabs 166 preferably contact the surgical fasteners for preventing the surgical fasteners from moving proximally within the elongated shaft 40 (FIG. 1) of the applicator instrument. This system is also described in commonly assigned U.S. Patent Appln. Publication Nos. US 2010/0292715, US 2010/0292712, US 2010/0292710, US 2010/0292713, and US 2011/079627, the disclosures of which are hereby incorporated by reference herein.

Figure 9:
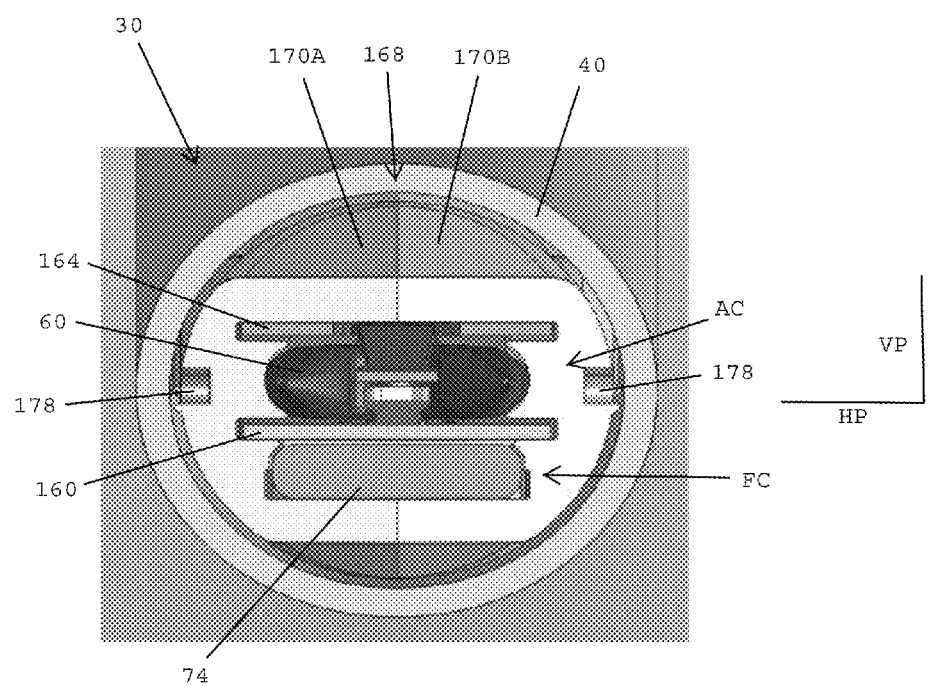
FIG. 9 shows a cross-sectional view of an elongated shaft of an applicator instrument including the advancer element and the anti-backup member shown in FIG. 8, in accordance with one embodiment of the present invention.

Referring to FIG. 9, in one embodiment, the applicator instrument 30 includes the elongated shaft 30, which is preferably angled or curved, and a guide member 168 that extends through the shaft. The guide member 168 may be a molded part including an advancer element channel AC and a firing channel FC. In one embodiment, the guide member 168 preferably has a first half 170A and a second half 170B that are assembled together. In one embodiment, the anti-backup member 164, the advancer element 160, and the surgical fasteners 60 are positioned within the advancer element channel AC of the first half 170A of the guide member, and the firing rod 74 and an insertion fork are positioned within the firing channel FC of the first half 170A of the guide member. The second half 170B of the guide member is assembled with the first half 170A for forming the assembled guide channel 168.

In one embodiment, the surgical fasteners 60 advance through the advancer element channel AC while lying within a laterally extending horizontal plane HP that is perpendicular to a vertical plane VP extending through the top and bottom of the applicator instrument. The orientation of the surgical fasteners within the guide member 168 enables the surgeon to control and/or be aware of the orientation of the surgical fasteners as they are dispensed from the shaft of the applicator instrument.

In one embodiment, the advancer element 160 advances the surgical fastener 60 distally through the advancer element channel AC and toward the distal end of the shaft 40. When the surgical fastener 60 becomes the lead surgical fastener at the distal end of the shaft 40, a staging leaf attached to the distal end of the anti-backup member 164 transfers the lead surgical fastener 60 from the advancer element channel AC to the firing channel FC for being aligned with the insertion fork at the distal end of the firing rod 74.

Figure 10A:
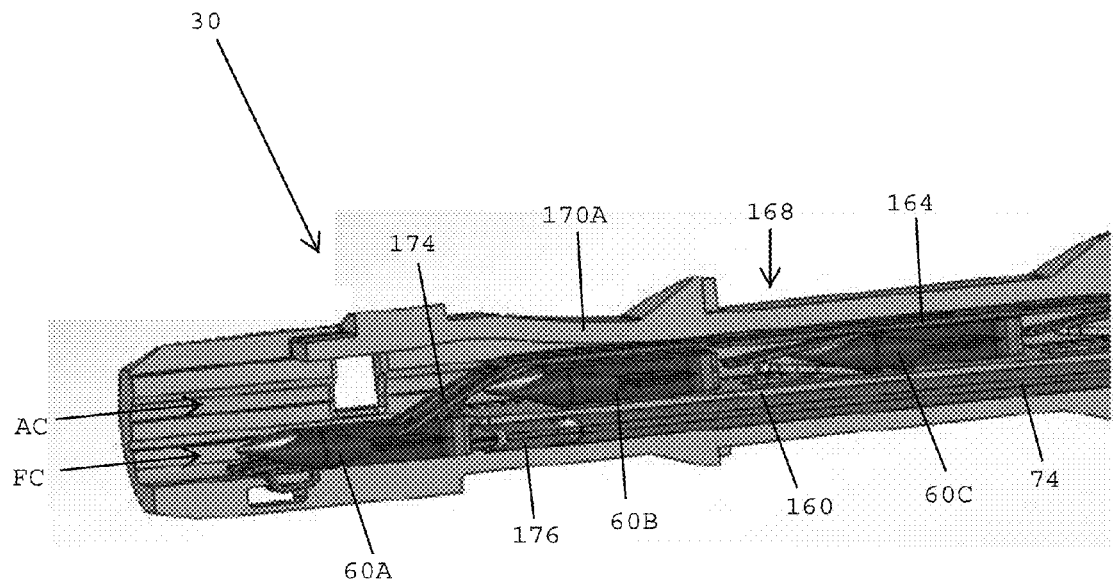
FIG. 10A shows a cross-sectional view of a distal end of a right guide member disposed inside a shaft of an applicator instrument including the advancer element and the anti-backup member shown in FIG. 8, in accordance with one embodiment of the present invention.

FIG. 10A shows the distal end of the first half 170A of the guide member 168. The second half 170B (FIG. 9) of the guide member has been removed to more clearly show the advancer element channel AC and the firing channel FC of the guide member 168. In one embodiment, twenty surgical fasteners 60A, 60B, 60C, . . . 60T are positioned between the advancer element 160 and the anti-backup member 164. The advancer element 160 cycles back and forth for advancing the surgical fasteners 60A, 60B, 60C, . . . 60T toward the distal end of the advancer element channel AC. The distal end of the anti-backup member 164 includes a staging leaf 174 that moves the lead surgical fastener 60A into the firing channel FC for alignment with the insertion fork 176 at the distal end of the firing rod 74.

Figure 10B:
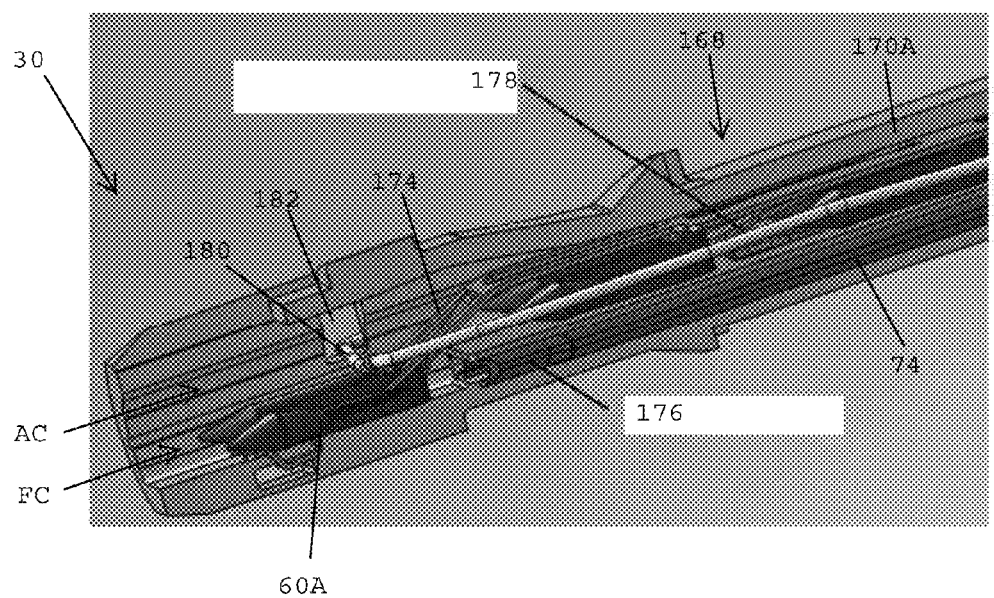
FIG. 10B shows the right guide member of FIG. 10A with a wire staging spring secured to the guide member, in accordance with one embodiment of the present invention.

Referring to FIGS. 9 and 10B, in one embodiment, the applicator instrument 30 includes a staging spring 178, such as a wire staging spring that is adapted to urge the staging leaf 174 to move into alignment with the insertion fork 176. In one embodiment, the wire staging spring 174 is U-shape and has a closed distal end 180 that passes through a window 182 formed in the distal end of the guide member 168. The closed distal end 180 of the wire staging spring 178 preferably engages the staging leaf 174 for urging the staging leaf to move into alignment with the insertion fork 176. As a result, after the lead surgical fastener 60A has been advanced onto the staging leaf 174 by the advancer element 160, and the advancer element is retracted, the wire staging spring 178 transfers the lead surgical fastener 60A from the advancer element channel AC to the firing channel FC for being aligned with the insertion fork 176 at the distal end of the firing rod 74. The firing rod and the insertion fork may then be extended for guiding the tines of the insertion fork onto the lead surgical fastener 60A.

Figure 11A:
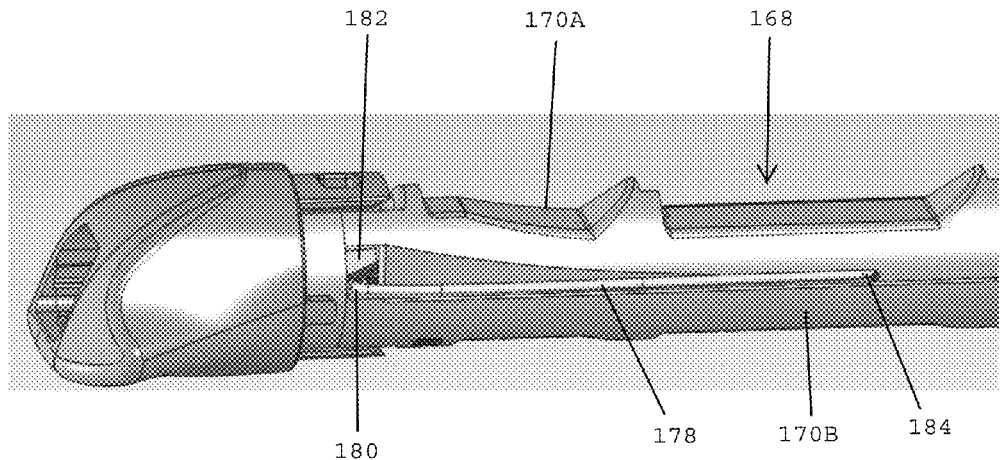
FIG. 11A shows a distal end of an applicator instrument including a left guide member, a wire staging spring and a cap having a surgical fastener dispensing window, in accordance with one embodiment of the present invention.
Figure 11B:
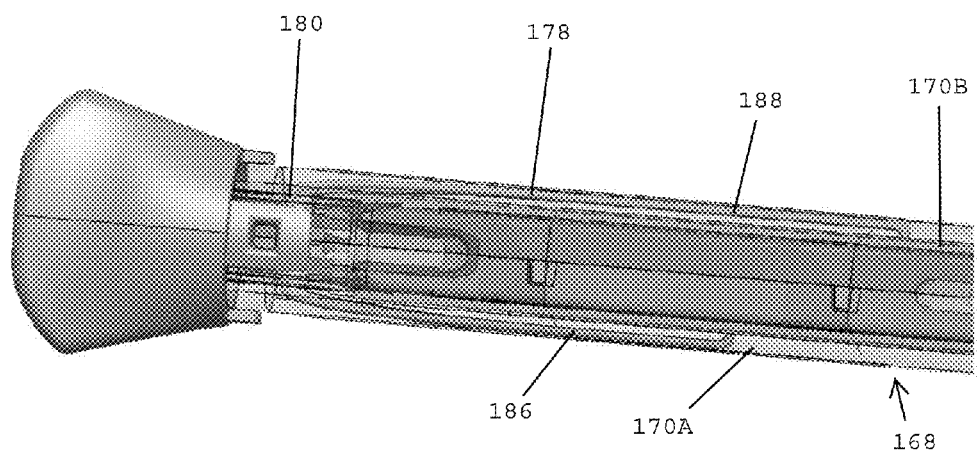
FIG. 11B shows a bottom view of FIG. 11A.

Referring to FIGS. 11A and 11B, in one embodiment, the wire staging spring 178 has a proximal end 184 that is secured to the guide member 168 and a closed distal end 180 that passes through the window 182 formed through the guide member adjacent the distal end of the guide member.

Referring to FIG. 11B, the wire staging spring 178 includes a first arm 186 that is secured to the first half 170A of the guide member 168 and a second arm 188 that is secured to the second half 170B of the guide member 168. The closed distal end 180 of the wire staging spring 178 passes through the window 182 (FIG. 11A) formed adjacent the distal end of the guide member 168.

Figure 12A:
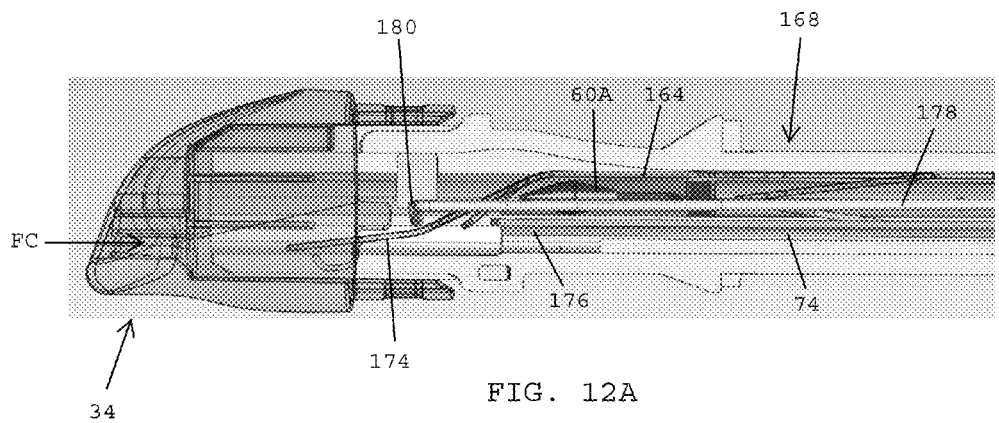
FIGS. 12A-12E show a method of aligning a lead surgical fastener with an insertion fork at a distal end of a firing rod, in accordance with one embodiment of the present invention.

FIGS. 12A-12E show the operation of the wire staging spring 178 for urging the staging leaf into alignment with the insertion fork at the distal end of the firing rod. Referring to FIG. 12A, the insertion fork 176 and the firing rod 74 are in a retracted position at the beginning of a firing cycle. A lead surgical fastener 60A has been advanced toward a distal end 34 of the applicator instrument. The distal end 180 of the wire staging spring 178 deflects the staging leaf 174 down into the firing channel FC of the guide member 168.

Figure 12B:
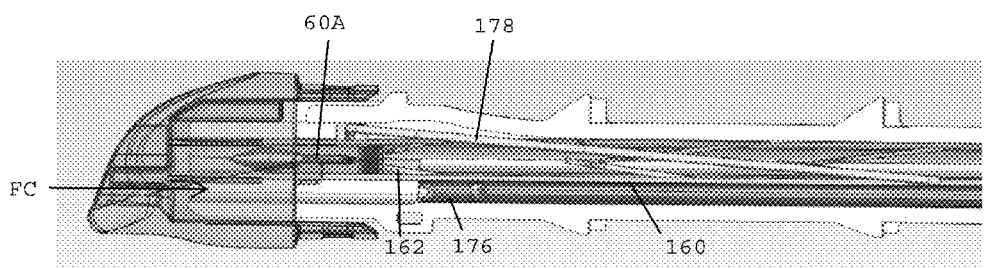

Referring to FIG. 12B, the trigger is pulled toward the proximal end of the device, which, in turn, moves the advancer element 160 toward the distal end 34 of the applicator instrument, whereby the advancer element tab 162 pushes the lead surgical fastener 60A distally for loading the lead surgical fastener onto the staging leaf at the distal end of the anti-backup member 164. The distal end of the extended advancer element 160 flexes the staging leaf and the wire staging spring 178 upwardly and away from the firing channel FC.

Figure 12C:
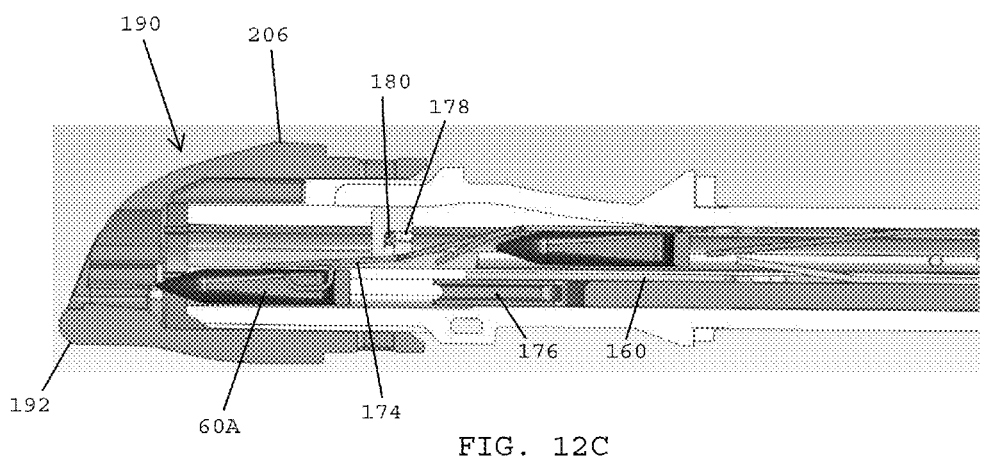

Referring to FIG. 12C, during a later stage of the firing cycle, the advancer element 160 is retracted whereupon the distal end 180 of the wire staging spring 178 urges the staging leaf 174 downwardly into the firing channel FC for aligning the lead surgical fastener 60A with the insertion fork 176. The staging leaf 174, which has been deflected downwardly into the firing channel, holds the lead surgical fastener 60A in position for being engaged by the insertion fork 176.

Figure 12D:
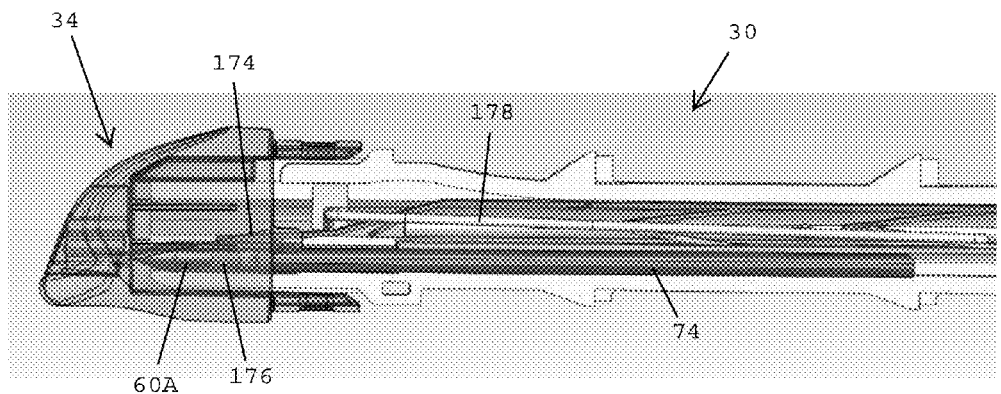

FIG. 12D shows a later stage of the firing cycle during which the insertion fork 176 and the firing rod 74 move distally whereupon the tines of the insertion fork 176 engage the lead surgical fastener 60A. As the insertion fork moves distally, the insertion fork 176 deflects the staging leaf 174 and the wire staging spring 178 out of the firing channel FC and into the advancer element channel AC.

Figure 12E:
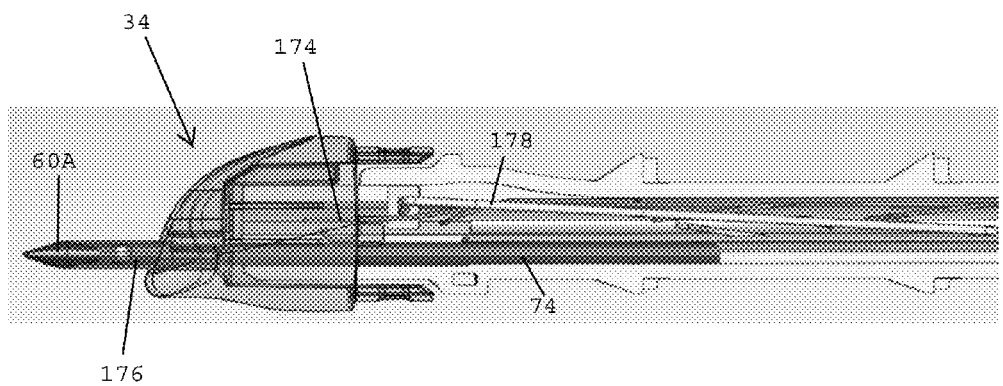

FIG. 12E shows the firing rod 74 and the insertion fork 176 fully extended in a distal-most position for dispensing the lead surgical fastener 60A from the distal end of the applicator instrument. The fully extended insertion fork 176 and firing rod 74 continue to deflect the staging leaf 174 and the wire staging spring 178 into the advancer element channel AC.

Figure 13A:
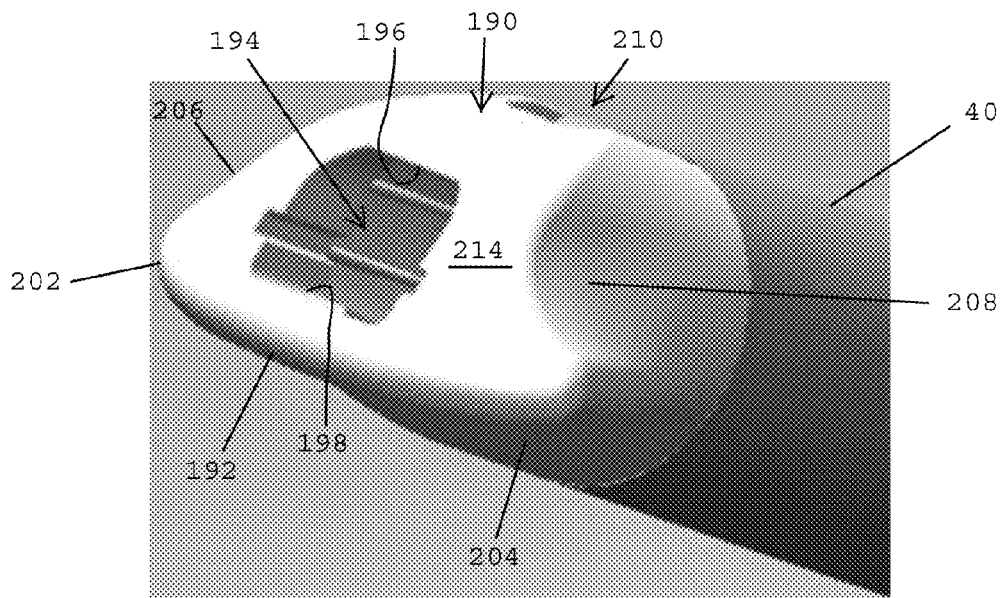
FIG. 13A shows a perspective view of a cap secured to a distal end of an elongated shaft of an applicator instrument, in accordance with one embodiment of the present invention.
Figure 13B:
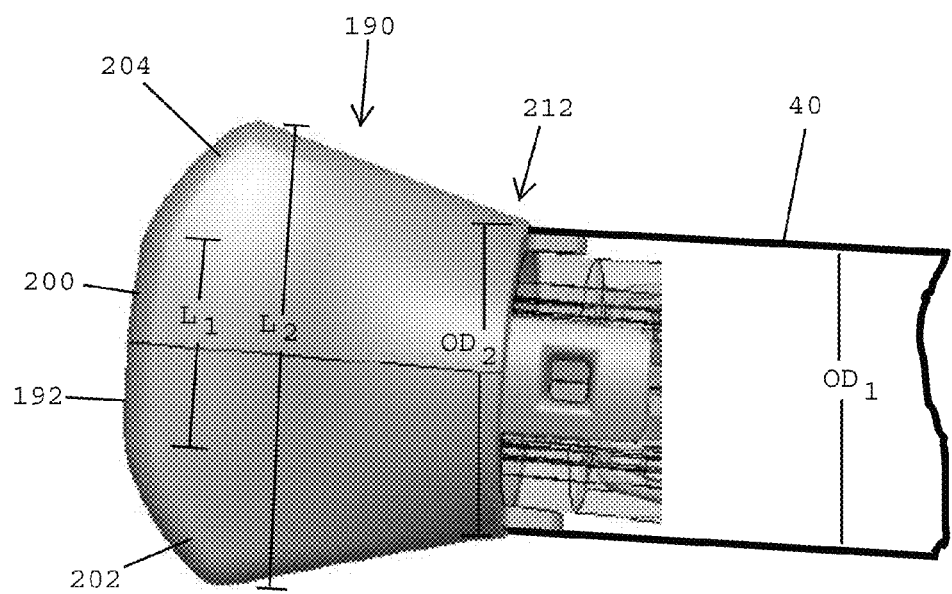
FIG. 13B shows a bottom plan view of FIG. 13A.
Figure 13C:
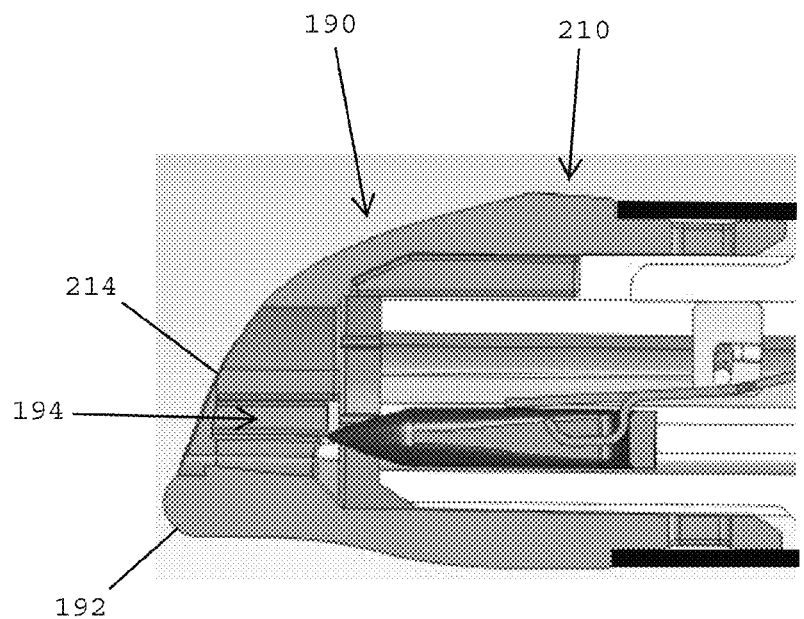
FIG. 13C shows a cross-sectional view of the cap shown in FIG. 13A.

Referring to FIGS. 13A-13C, in one embodiment, a cap 190 is secured to the distal end of the outer shaft 40. In one embodiment, the cap 190 is affixed to the distal end of the outer shaft so that the cap 190 does not rotate or translate relative to the shaft 40. In one embodiment, the shaft 40 has an outer diameter $OD_1$ of about 6-12 mm and more preferably about 8 mm. The cap 190 preferably has a smooth, curved and contoured outer surface that has no sharp edges so that the cap will not snare or damage the mesh fabric of a mesh implant.

In one embodiment, the cap 190 has a lower distal edge 192 that extends along the bottom of the cap and a delivery window 194 for dispensing a surgical fastener. In one embodiment, the cap 190 is adapted for insertion into the pocket of an open skirt mesh having a top mesh piece and a bottom mesh piece joined at a peripheral seam, whereby the lower distal edge 192 is advanced into contact with the inside of the seam and the cap may be easily slid along the inside of the seam between the top and bottom layers without snagging or damaging the mesh material. The lower distal edge 192 is adapted to sit atop the bottom mesh piece of an open skirt mesh to ensure that the delivery window 194 of the cap 190 is a set distance above the seam of the skirted mesh.

In one embodiment, the delivery window 194 has an upper end 196 and a lower end 198. The lower end 198 of the delivery window 194 is preferably spaced from the lower distal edge 192 to ensure that surgical fasteners are dispensed above the seam of the open skirt mesh and into the top mesh piece of the implant. Referring to FIG. 13B, in one embodiment, the lower distal edge 192 includes a central section 200 having a length $L_1$ of about 6-10 mm that generally matches the outer diameter $OD_1$ of the shaft 40 and first and second extensions 202, 204 that extend beyond the outer diameter $OD_1$ of the shaft 40 about 2-3 mm. With the addition of the first and second extensions 202, 204, the lower distal edge 192 has a total length $L_2$ of about 10-20 mm that is greater than the outer diameter $OD_1$ of the shaft 40. In one embodiment, the first and second extensions 202, 204 have bottom surfaces that are convex and that extend laterally from the bottom surface of the lower distal edge, and first and second top surfaces 206, 208 that are concave and that extend toward an upper end 210 of the cap 190. The first and second extensions 202, 204 preferably distribute forces over a broader area of mesh, such as a bottom mesh piece of an open skirt mesh, such as when a physician applies forward forces on the applicator instrument handle and counter-pressure on opposing tissue.

In one embodiment, the cap has a proximal end 212 that that is secured to the distal end of the shaft 40 and that transitions into a cylindrical shape to match the outer diameter $OD_1$ of the shaft 40. In one embodiment, the proximal end 212 of the cap 190 has an outer diameter $OD_2$ of about 6-12 mm and more preferably about 8 mm that generally matches and conforms to the outer diameter $OD_1$ of the shaft 40.

Referring to FIGS. 13A and 13C, in one embodiment, the cannula cap 190 has a distal face 214 that slopes upwardly and proximally from the lower distal edge 192 to the upper end 210 of the cannula cap 190. When the cap 190 is inserted into the pocket of an open skirt mesh having a peripheral seam, the lower distal edge 192 is preferably abutted against a bottom mesh piece of the open skirt mesh and advanced toward an inside of a seam until the sloping distal face 214 engages the top mesh piece of the open skirt mesh to ply the top mesh piece of the skirt away from the bottom mesh adjacent the inside of the seam. The delivery window 194 is desirably spaced from the lower distal edge 192 to insure that the surgical fasteners 60 dispensed through the delivery window pass through the top mesh piece and not the peripheral seam or the bottom mesh piece of the open skirt mesh. The first and second extensions 202, 204 further ensure that the cap orients the device relative to the seam of the mesh such that surgical fasteners are delivered into the top mesh piece.

In one embodiment, the cap 190 is contoured to ensure there are no sharp edges at the distal end of an applicator instrument that may catch or damage the mesh fabric of an implant. The contoured cap ensures that a physician may slide a distal end of an applicator instrument along the inside of a seam of an open skirt mesh when positioning or re-positioning the distal end of the application instrument for initial and subsequent deployment of surgical fasteners.

Figure 14A:
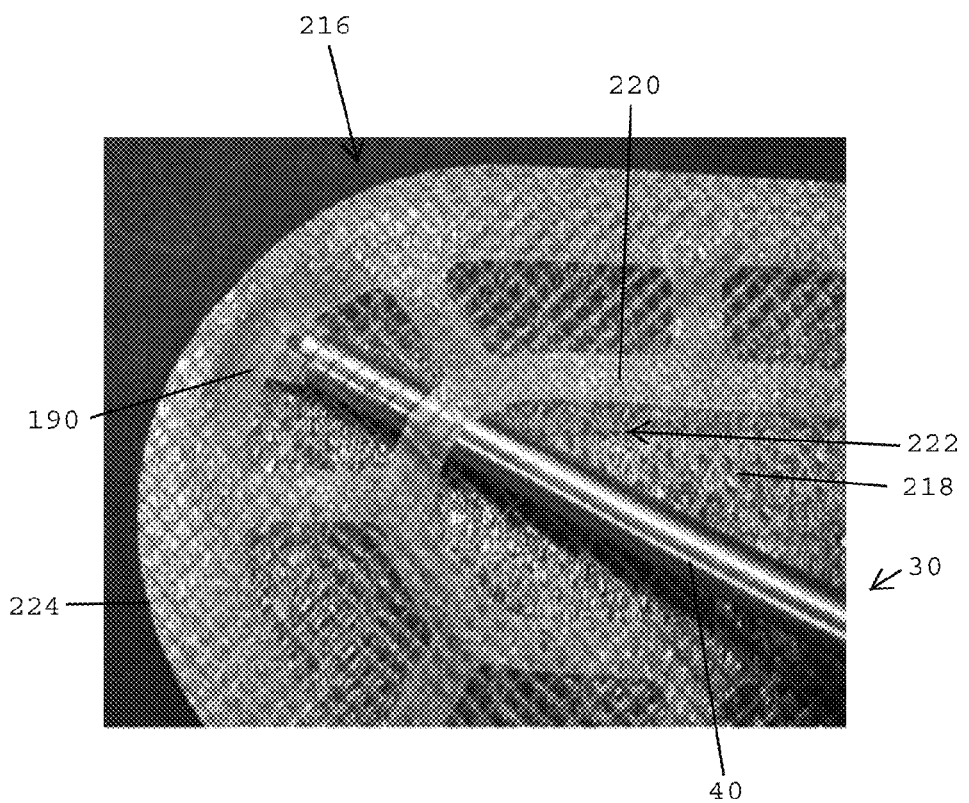
FIG. 14A shows a top view of an open skirt mesh having a distal end of an applicator instrument inserted into a central opening of the open skirt mesh, in accordance with one embodiment of the present invention.
Figure 14C:
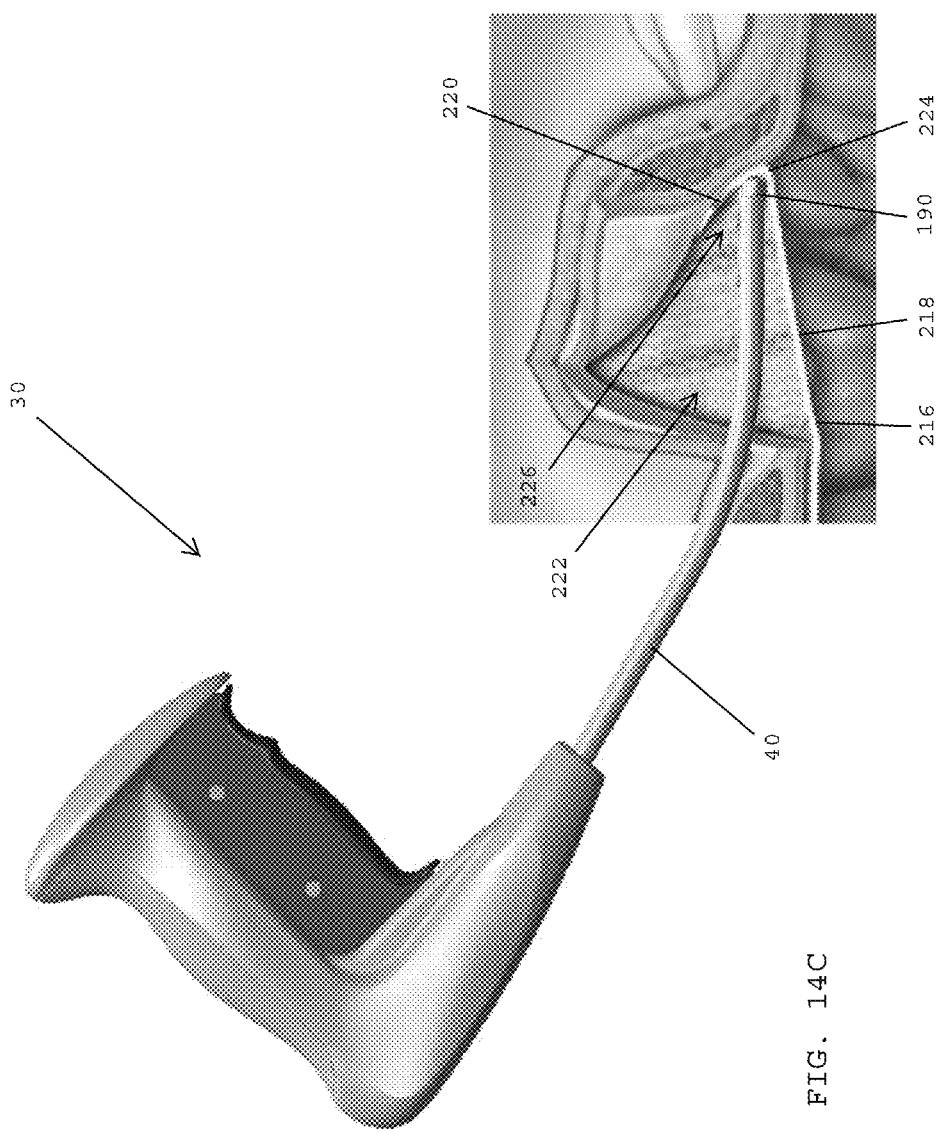
FIG. 14C shows a view of a stage of an open hernia repair procedure with an open skirt mesh inserted into a surgical opening and an applicator instrument used for mesh fixation, in accordance with one embodiment of the present invention.

Referring to FIGS. 14A-14C, in one embodiment, an applicator instrument 30 having the elongated shaft 40 and the cap 190 is used to secure an open skirt mesh 216 to soft tissue. In one embodiment, the open skirt mesh 216 has a bottom mesh piece 218, a top mesh piece 220 with a central opening 222, and a peripheral seam 224 that joins the outer edges of the bottom mesh piece 218 and the top mesh piece 220 to define a pocket 226 that extends between the top and bottom mesh pieces.

In one embodiment, the cap 190 and the distal end of the shaft 40 of an applicator instrument 30 are inserted through the central opening 222 of the top mesh piece 220 and advanced into the pocket 226 and toward the peripheral seam 224 of the open skirt mesh 216. The lower distal edge 192 (FIG. 14B) of the cap 190 is abutted against the bottom mesh piece 218 and advanced toward the peripheral seam 224, whereupon the lower distal edge 192 and the sloping distal face 214 (FIG. 14B) of the cap 190 ply the top mesh piece 220 away from the bottom mesh piece 218 at the peripheral seam 216. The lower distal edge 192 of the cap 190 spaces the dispensing window 194 of the cap 190 above the seam 224 and in alignment with the top mesh piece 220 so that the surgical fastener 60 (FIGS. 3 and 12E) passes through the top mesh piece 220 and does not pass through the seam 224 or the bottom mesh piece 218.

In one embodiment, a patient with a ventral hernia is prepared for an open hernia repair procedure. The skin area surrounding the hernia is scrubbed with a conventional antimicrobial solution, such as betadine. The patient is administered conventional general anesthesia in a conventional manner by induction and inhalation. In one embodiment, the surgeon initiates the surgical procedure by making an incision in the skin and subcutaneous tissue overlying the hernia. In the case of planned intra-peritoneal mesh placement, the hernia sac is opened. The edges of the healthy fascia around the defect are examined and any attachments of the viscera to the abdominal wall are divided to create a free space for fixation of the mesh.

At this stage of the surgical procedure, the surgeon prepares a surgical mesh. The surgical mesh may be a shirted hernia mesh having a bottom repair layer and a top fixation layer, or any suitable mesh such as the mesh disclosed in commonly assigned U.S. patent application Ser. No. 13/443,347, filed Apr. 10, 2012, entitled "SINGLE PLANE TISSUE REPAIR PATCH," the disclosure of which is hereby incorporated by reference herein. In one embodiment, the bottom repair layer of a skirted hernia mesh may be referred to as a bottom mesh piece and the top fixation layer may be referred to as a top mesh piece. The outer peripheries of the respective bottom repair layer and the top fixation layer are preferably joined together at a peripheral seam that extends around the outer perimeter of the skirted hernia mesh. In one embodiment, the top fixation layer desirably has an opening in the center. In one embodiment, four sutures may be placed at the four compass points of the mesh (i.e., North, South, East, and West).

In one embodiment, the mesh is inserted through the skin incision and through the fascia defect into the pre-peritoneal space. The surgeon desirably deploys the mesh into the abdominal cavity by hand. The mesh is oriented such that the bottom repair layer is facing the patient's abdominal contents and the top fixation layer is facing the abdominal wall. The sutures may be secured trans-abdominally using suture passers, as desired.

In one embodiment, an applicator instrument is used for dispensing surgical fasteners for mesh fixation. In one embodiment, the applicator instrument is desirably oriented so that the handle and trigger are above the body of the applicator instrument for being clear of the patient's abdomen. The elongated outer shaft of the applicator instrument is preferably inserted through the central opening formed in the top fixation layer so that the distal end of the shaft is disposed between the top fixation layer and the bottom repair layer. In one embodiment, the outer shaft of the applicator instrument is curved and the curvature of the outer shaft is pointed upward and away from the posterior end of the patient (i.e., toward the top fixation layer). With the cap of the applicator instrument between the top fixation layer and the bottom repair layer, the cap is advanced toward the outer periphery of the mesh implant until the cap reaches the peripheral seam of the mesh. In one embodiment, while the applicator instrument is held with the surgeon's first hand, the second hand may be used to apply external counter pressure to the skin, opposing the cap at the distal end of the applicator instrument. The cap has a lower distal edge that contacts the bottom repair layer and the inside of the peripheral seam. The cap preferably has a distal face that slope upwardly and away from the lower distal edge. When the lower distal edge of the cap is advanced to the seam, the sloping distal face of the cap plies the top fixation layer away from the bottom repair layer. The lower distal edge desirably functions as a spacer that ensures that the surgical fastener dispensing window in the cap is above the peripheral seam of the mesh implant and is aligned with the top fixation layer.

In one embodiment, with the dispensing window of the cap aligned with the top fixation layer, the trigger is squeezed with a single stroke action to deploy a surgical fastener or strap through the cap dispensing window for securing the top fixation layer to the abdominal wall. The trigger returns itself to an initial start position for a firing cycle. The applicator instrument is preferably repositioned to another point along the seam of the mesh and another surgical fastener is delivered. The process is repeated until the entire perimeter of the mesh is secured, with the surgical fasteners desirably spaced about 1-2 mm apart around the periphery of the mesh implant. In one embodiment, a second series of straps may optionally be applied closer to the center of the mesh in what is called a double crown technique.

In one embodiment, after 20 surgical fasteners have been dispensed, the applicator instrument will lock out with the trigger closed. If needed, a new applicator instrument may be used to complete the remainder of the repair procedure. After a desired number of surgical fasteners have been deployed, the applicator instrument is removed from the patient. The hernia defect may be primarily closed if desired. The skin incision may be closed using appropriate suturing or closure techniques, and the incision is appropriately bandaged. After the repair procedure is complete, the patient may be moved to a recovery room.

Figure 15A:
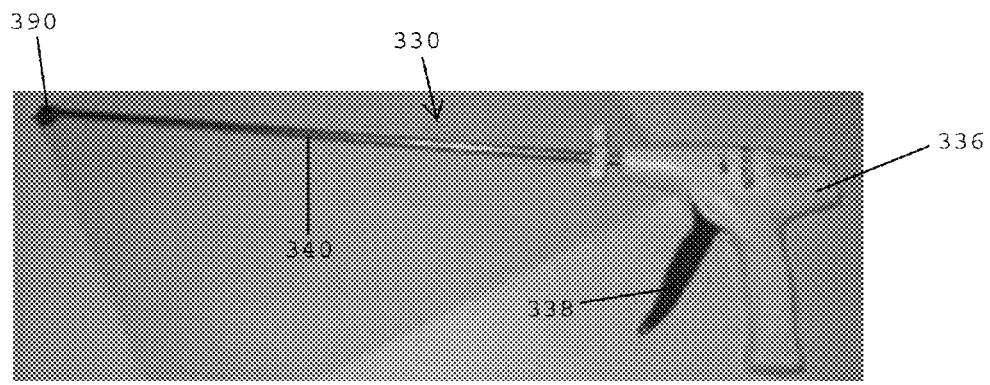
FIG. 15A shows a left side view of an applicator instrument having an elongated shaft and a cap secured to a distal end of the elongated shaft, in accordance with one embodiment of the present invention.
Figure 15B:
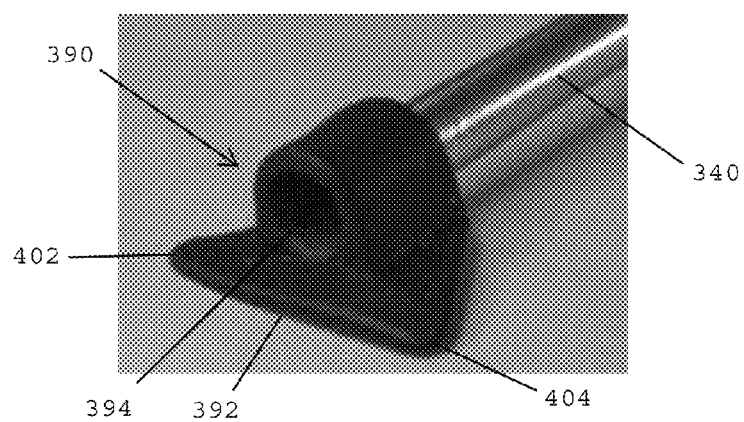
FIG. 15B shows a perspective view of the cap shown in FIG. 15A.
Figure 15C:
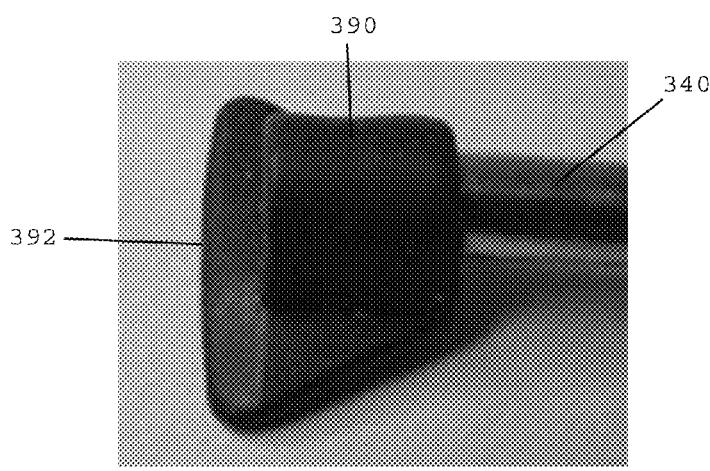
FIG. 15C shows a top perspective view of the cap shown in FIG. 15B.

Referring to FIGS. 15A-15C, in one embodiment, an applicator instrument 330 includes a handle 336 having a trigger 338 and a shaft 340 extending from a distal end of the handle 336. A cap 390 is desirably secured to a distal end of the shaft. The cap 390 preferably includes a delivery window 394 for dispensing surgical fasteners from the distal end of the applicator instrument 330. In one embodiment, the cap 390 has a lower distal edge 392 and first and second lateral extensions 402, 404 that extend laterally from the lower distal edge 392. The first and second lateral extensions 402, 404 preferably extend beyond the outer diameter of the outer shaft 340 to define a length that is greater than the outer diameter of the shaft.

Figure 16:
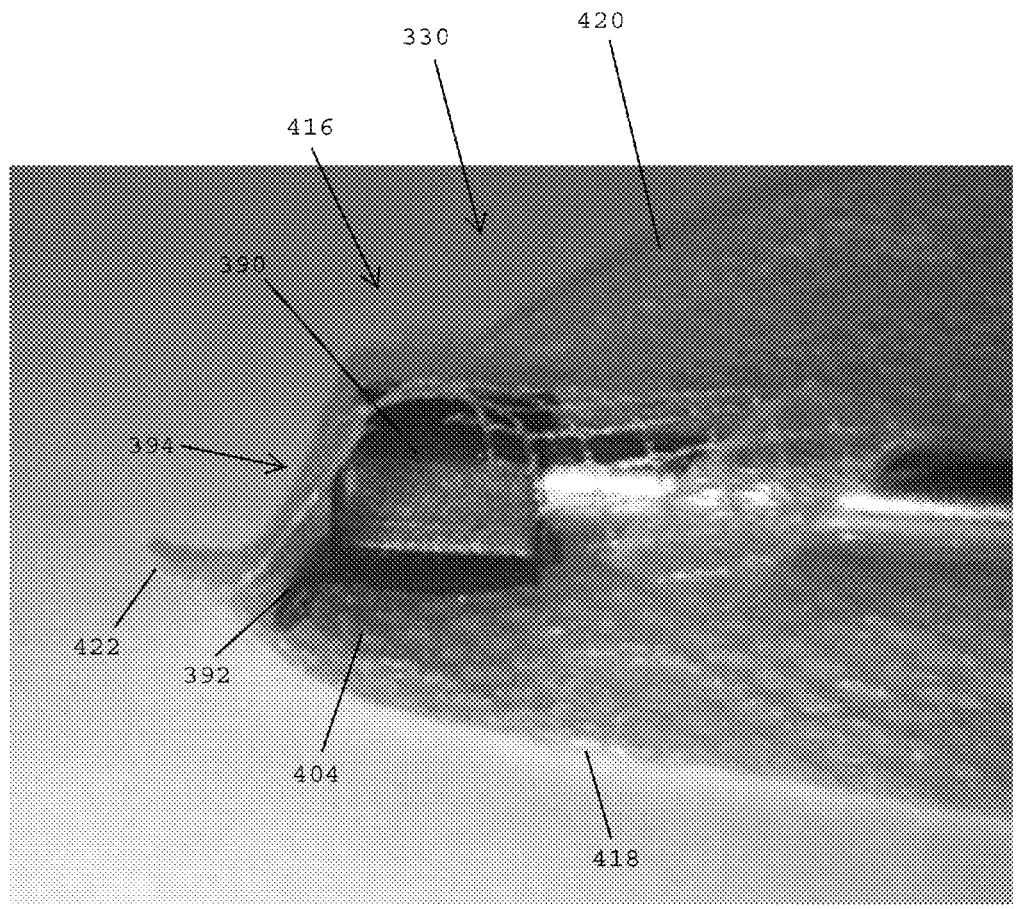
FIG. 16 shows the cap at the distal end of the applicator instrument of FIGS. 15A-15C inserted between top and bottom mesh pieces of an open skirt mesh, in accordance with one embodiment of the present invention.

Referring to FIG. 16, in one embodiment, the distal end of the applicator instrument 330 is adapted for being inserted into a pocket of an open skirt mesh 416. In one embodiment, the open skirt mesh 416 preferably includes a bottom mesh piece 418 and a top mesh piece 420 that opposes the bottom mesh piece 418. The outer edges of the bottom and top mesh pieces 418, 420 are joined together at a peripheral seam 422. When the cap 390 is inserted into the pocket of the skirted mesh 416, the lower distal edge 392 and the first and second lateral extensions 402, 404 preferably engage the inner surface of the bottom mesh piece 418 for flattening the bottom mesh piece in the vicinity of the cap 390. The lower distal edge 392 preferably has a thickness that spaces the delivery window 394 above the seam 422 to ensure that the surgical fasteners are dispensed through the top mesh piece 420 and not the seam 424 or the bottom mesh piece 418.

Figure 17:
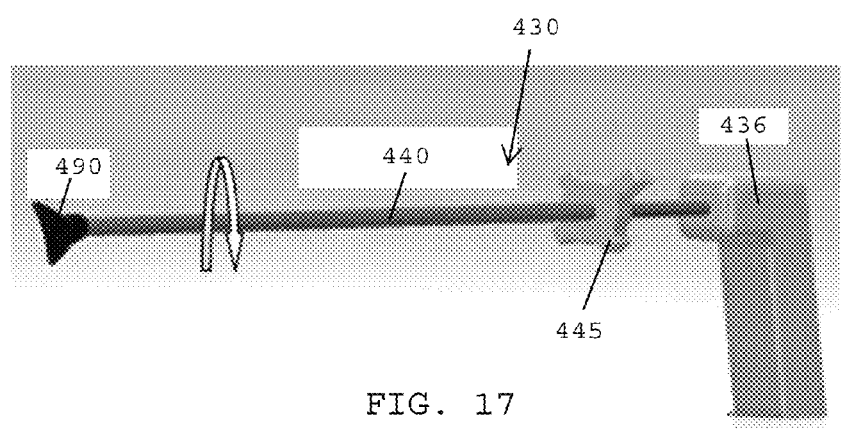
FIG. 17 shows an applicator instrument having an elongated shaft that is rotatable, in accordance with one embodiment of the present invention.

Referring to FIG. 17, in one embodiment, an applicator instrument 430 includes a handle 436 and an elongated shaft 440 extending distally from the handle 436. The applicator instrument 430 includes a rotating element 445 secured to the outer shaft 440. A cap 490 is secured to a distal end of the outer shaft 440. The cap 490 may include one or more of the features disclosed in the embodiments shown in FIGS. 13A-13C or FIGS. 15B-15C. In one embodiment, the rotating element 445 may be engaged for rotating the elongated shaft 440 about its longitudinal axis. The cap 490 preferably rotates simultaneously with the shaft 440.

Figure 18A:
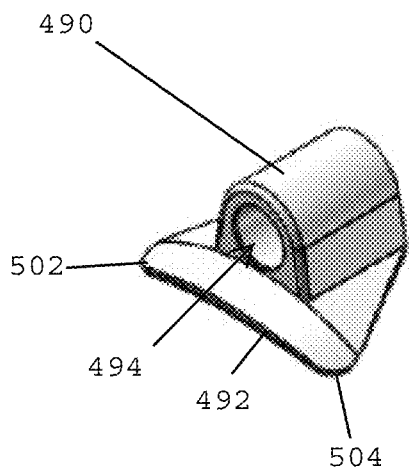
FIGS. 18A-18C show an edge adapter cap with a living hinge that is securable to a distal end of an elongated shaft of an applicator instrument, in accordance with one embodiment of the present invention.
Figure 18B:
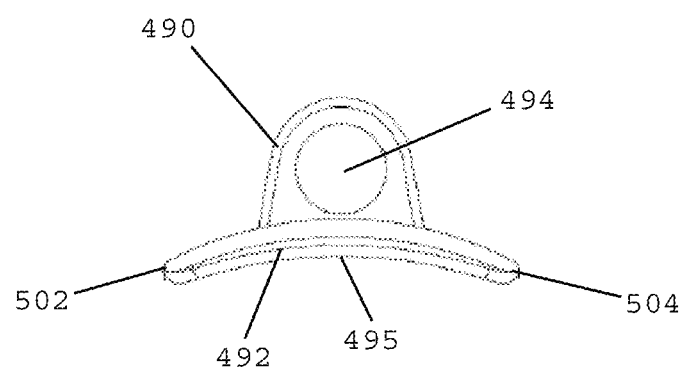
Figure 18C:
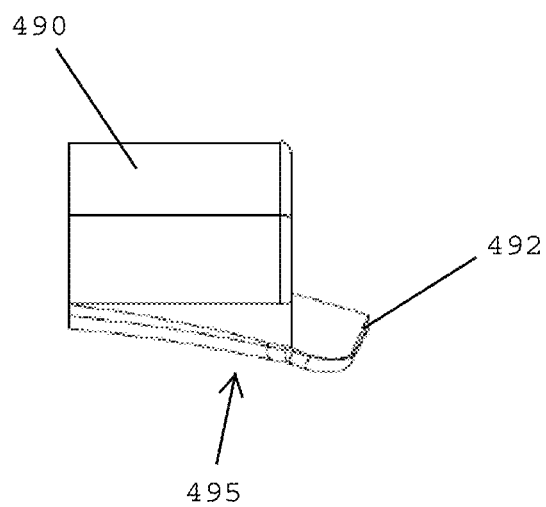

Referring to FIGS. 18A-18C, in one embodiment, an applicator instrument desirably includes a cap 490 secured to a distal-most end of an outer shaft. The cap 490 includes a distal-lower edge 492 having a concave bottom surface 495. The cap 490 includes first and second extensions 502, 504 that extend laterally from the lower distal edge 492. The cap 490 preferably includes a delivery window 494 that is aligned with the firing chamber of the applicator instrument for dispensing surgical fasteners through the delivery window.

In one embodiment, the distal-lower end 492 of the cap 490 has a thickness that spaces the delivery window 494 from the concave bottom surface 495 of the distal-lower edge. After the lower distal edge 492 is abutted against the inside of the peripheral seam of a mesh implant, the thickness of the lower distal edge ensures that the delivery window 494 of the cap 490 is spaced above and away from the peripheral seam so that the surgical fasteners are dispensed into the top mesh piece of a skirted mesh, and not into the seam or the bottom mesh piece.

In one embodiment, when the cap 490 is inserted into the pocket of a skirted mesh, the lower distal edge 492 is advanced toward the peripheral seam of the skirted mesh with the concave bottom surface 495 facing the bottom mesh piece and the delivery window aligned with the top mesh piece. In one embodiment, the concave bottom surface 495 of the lower distal edge 492 desirably provides a living hinge that is flexible so that the lower distal edge may flatten out for stretching a mesh piece (e.g., a bottom mesh piece) of an implant during positioning of the cap 490 for dispensing a surgical fastener.

Figure 19:
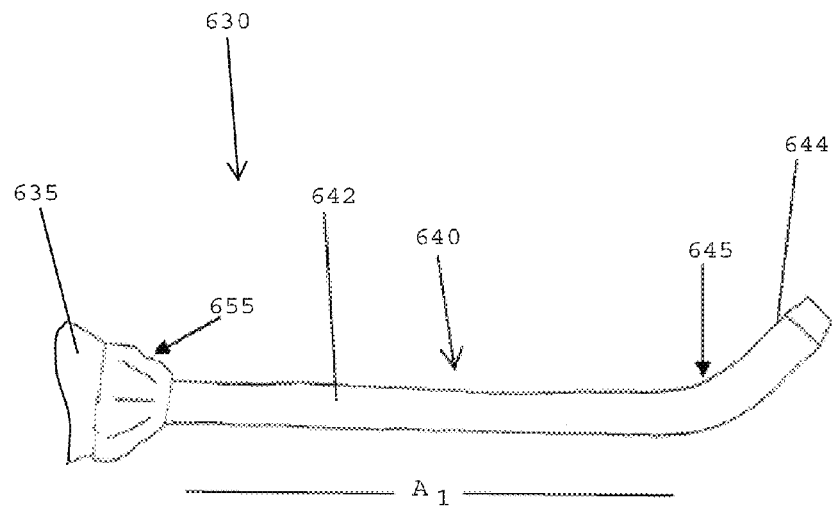
FIG. 19 shows a side view of a distal end of an applicator instrument for dispensing surgical fasteners including a curved outer shaft and a shaft rotating element for changing the orientation of a distal end of the curved outer shaft relative to a proximal end of the curved outer shaft, in accordance with one embodiment of the present invention.

Referring to FIG. 19, in one embodiment, an applicator instrument 630 for dispensing surgical fasteners includes a curved outer shaft 640, similar to the structure described above in FIG. 1, having a proximal section 642 and a distal section 644 that is coupled with the proximal section via a curved section 645. In one embodiment, the applicator instrument 630 preferably includes an outer shaft rotating element 655 rotatably mounted to a distal end of a device housing 635. The outer shaft rotating element 635 is connected with the proximal section 642 of the outer shaft 640 for selectively rotating the outer shaft 640. As a result, the outer shaft rotating element 655 enables an operator to selectively rotate the proximal section 642 of the curved outer shaft 640 along a longitudinal axis $A_1$ for changing the orientation of the distal end section 644.

Figure 20:
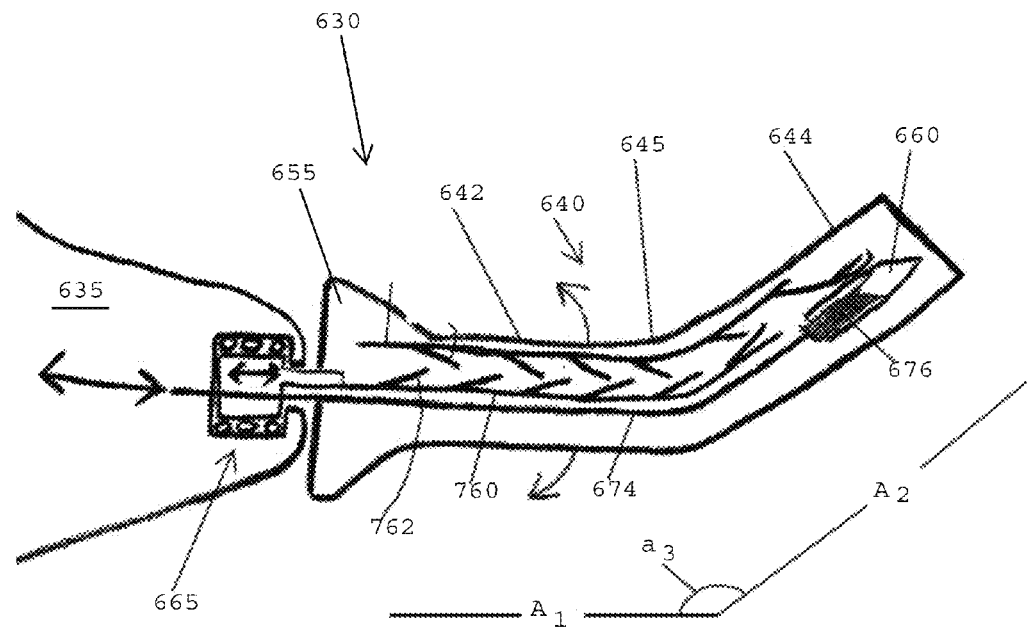
FIG. 20 shows a cross-sectional view of the distal end of the applicator instrument including the curved outer shaft shown in FIG. 19.

FIG. 20 shows a cross-section of the applicator instrument 630 in FIG. 19. Referring to FIG. 20, in one embodiment, the curved outer shaft 640 includes the proximal section 642 extending along the axis $A_1$ and the distal section 644 extending along the axis $A_2$. The curved section 645 defines the angle $\alpha_3$ between the proximal section 642 and the distal section 644. The curved outer shaft 640 has an elongated internal conduit through which surgical fasteners 660 may advance distally. The applicator instrument 630 preferably includes an advancer 760 having advancer tabs 762 for advancing the surgical fasteners 660 one position toward the distal end of the curved outer shaft 640 each time the trigger is pulled. The applicator instrument also desirably includes an anti-backup element 664 having anti-backup tabs 666 for preventing the surgical fasteners from moving proximally. The applicator instrument 630 also includes a flexible firing element 674, such as a flexible cable, that is able to transfer forces from the firing system, which operates as described herein, to the distal-most surgical fastener 660 in the outer shaft 640. The flexible firing element 674 is resistant to compression along its longitudinal axis. The flexible firing element 674 may also be twisted. In one embodiment, as the outer shaft rotating element 655 is rotated relative to the housing 635 for changing the orientation of the distal section 644 of the curved outer shaft 640, the flexible firing element 674 is able to flex, twist and bend to maintain a linkage between the firing system and a rigid insertion fork 676 having tines at a distal end thereof that are adapted to engage the sides of a surgical fastener 660. The flexible firing element 674 preferably transfers energy from the firing system to the rigid insertion fork 676 that engages the sides of a surgical fastener for driving the surgical fastener into soft tissue as described in more detail above.

In one embodiment, the firing system is the same as that described above but acts along the central axis of the proximal section 642 of the shaft. The flexible element of the firing system 674 extends through a rotary advancing system 665. The rotary advancing system 665 is preferably aligned with the proximal section 642 of the curved outer shaft 640. The rotary advancing system 665 is adapted to rotate with the curved outer shaft 640 around a central axis. The advancing system is actuated from the above-described indexing system of the applicator instrument 640 that interfaces with the rotary firing system 665.

Figure 21:
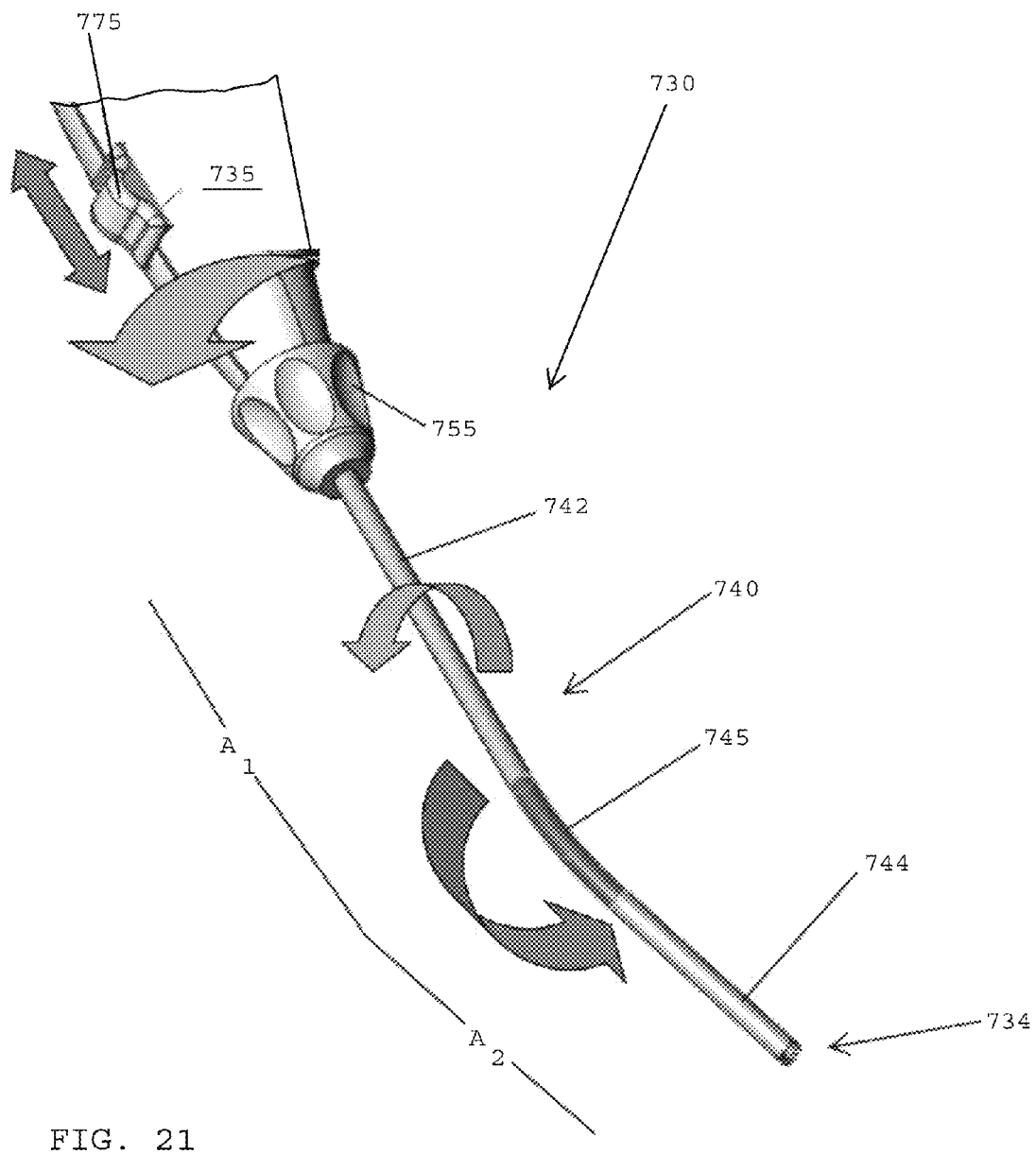
FIG. 21 shows a perspective view of a distal end of an applicator instrument for dispensing surgical fasteners including an articulating element and an outer shaft rotating element for changing the orientation of the distal end of the outer shaft relative to a proximal end of the outer shaft, in accordance with one embodiment of the present invention.

Referring to FIG. 21, in one embodiment, an applicator instrument 730 for dispensing surgical fasteners preferably includes a flexible, articulatable outer shaft 740 having a proximal section 742 that extends along an axis $A_1$, a distal section 744 that extends along an axis $A_2$ and a flexible, articulatable intermediate section 745 that enables the distal section 744 to articulate relative to the proximal section 742 for changing the angle therebetween. In one embodiment, the proximal and distal sections 742, 744 of the articulating outer shaft 740 are less flexible and the intermediate section 745 is more flexible for enabling the articulating movement.

The applicator instrument 730 desirably includes an outer shaft rotating element 755 that is mounted at a distal end of the housing 735 and that is secured with the proximal section 742 of the outer shaft 740. Rotation of the outer shaft rotating element 755 results in simultaneous rotation of the proximal section 742 of the outer shaft 740 about the longitudinal axis $A_1$, which, in turn, changes the orientation of the distal section 744 of the curved outer shaft 740 relative to the proximal section.

Figure 22:
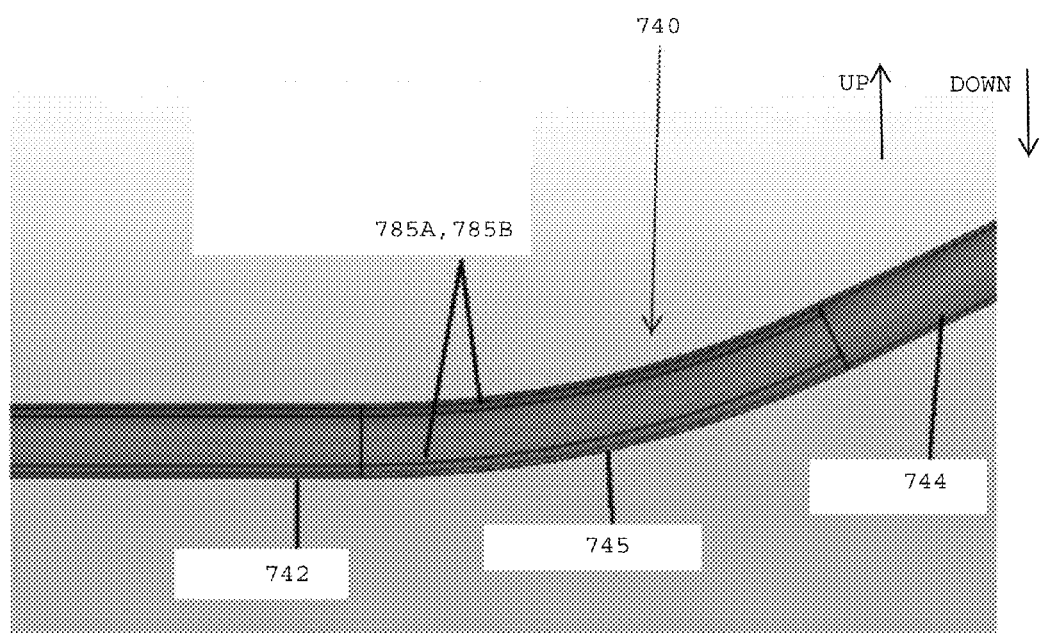
FIG. 22 shows a cross-sectional view of the outer shaft shown in FIG. 21.

In one embodiment, the applicator instrument 730 also desirably includes an articulation control element 775 that is mounted on the housing 735. In one embodiment, the articulation control element 775 is preferably slideably mounted on the housing 735 for moving distally and proximally. Referring to FIGS. 21 and 22, in one embodiment, the applicator instrument includes flexible linkages 785A, 785B having proximal ends coupled with the articulation control element 775 and distal ends coupled with the distal section 744 of the curved outer shaft 740. As shown in FIG. 22, the outer shaft 740 includes the proximal section 742, the distal section 744, and the intermediate flexible section 745 that extends between the proximal section 742 and the distal section 744. The first and second linkages 785A, 785B extend through the proximal section 742 and the flexible section 745, with the distal ends of the linkages coupled with the distal section 744. As the articulation control element 775 (FIG. 21) is moved toward the distal end of the applicator instrument 730, the first and second linkages 785A, 785B cooperate for changing the angle of the distal section 744 of the outer shaft relative to the proximal section 742 of the outer shaft. In one embodiment, as the articulation control element 775 moves toward the distal end 734 of the applicator instrument 730, the distal section 744 moves up. As the articulation control element 775 is moved towards the proximal end 732 of the applicator instrument 730, the first and second linkages 785A, 785B cooperate to move the distal section 744 down. Thus, the angle of the distal section 744 of the flexible outer shaft 740 may be changed relative to the proximal section 742 by moving the articulating control element 755 in proximal and distal directions until a desired angle is obtained. In one embodiment, the articulation control element enables an operator to toggle the outer shaft 740 between a straight configuration and a curved or angled configuration. After a desired straight, curved, or angled configuration is obtained, the orientation of the distal section 744 relative to the proximal section 742 of the outer shaft 740 may be changed by rotating the outer shaft rotating element 755, which, in turn, changes the orientation of the distal section 744.

The applicator instrument 730 of FIGS. 21 and 22 preferably includes a flexible firing element, a flexible advancer, and a flexible anti-backup element as described above in FIG. 20 to maintain an operating linkage with both the firing system and the surgical fastener advancing system as the outer shaft is rotated and/or articulated.

The headings used herein are for organizational purposes only and are not meant to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. An applicator instrument for dispensing surgical fasteners comprising:
    a housing;
    a firing system disposed in said housing and being moveable in distal and proximal directions along a first axis;
    an elongated shaft extending from said housing, said elongated shaft having a proximal section and a distal section that is oriented at an angle relative to the proximal section;
    a plurality of surgical fasteners disposed in said elongated shaft for being dispensed from a distal end of said elongated shaft;
    a handle extending upwardly from said housing along a second axis that defines an acute angle with said first axis;
    a trigger mounted on said handle;
    a linkage coupling said trigger with said handle and said firing system, wherein when said trigger is squeezed toward said handle, said linkage guides said trigger along a linear path of movement relative to said handle, wherein said trigger has a longitudinal axis that is parallel to the second axis of said handle, and wherein the second axis of said handle and the longitudinal axis of said trigger slope toward the distal end of said elongated shaft.

2. The applicator instrument as claimed in claim 1, wherein the proximal section of said elongated shaft extends along the first axis, and wherein said elongated shaft has a curved section located between the proximal section and the distal section.

3. The applicator instrument as claimed in claim 1, wherein said surgical fasteners are arranged in series within said elongated shaft for being dispensed one at a time from the distal end of said elongated shaft.

4. The applicator instrument as claimed in claim 3, wherein said trigger is squeezed toward said handle and a proximal end of said applicator instrument for activating said linkage, which, in turn, moves said firing system along the first axis toward the distal end of said elongated shaft.

5. The applicator instrument as claimed in claim 4, further comprising a guide member disposed inside said elongated shaft and extending along the length of said elongated shaft, wherein said guide member curves and has a curved conduit that extends along the length of said guide member.

6. The applicator instrument as claimed in claim 5, wherein said curved conduit comprises:
    an advancing channel for advancing said surgical fasteners toward the distal end of said elongated shaft; and
    a firing channel for dispensing said surgical fasteners one at a time from the distal end of said elongated shaft.

7. The applicator instrument as claimed in claim 6, further comprising:
    an advancer element disposed in said advancer element channel and being moveable in distal and proximal directions for advancing said surgical fasteners toward the distal end of said elongated shaft;
    an anti-backup member disposed in said advancer element channel and opposing said advancer element for preventing said surgical fasteners from moving toward the proximal end of said elongated shaft;
    a firing rod disposed in said firing channel and being moveable between a retracted position and an extended position for dispensing a lead surgical fastener from the distal end of said elongated shaft;
    a distal-most end of said anti-backup member including a staging leaf that receives a leading one of said surgical fasteners from said advancer element and transfers the leading one of said surgical fasteners from said advancer element channel to said firing channel for being aligned with said firing rod;
    a wire staging spring attached to said guide member and having a distal end that contacts said staging leaf for applying a spring force for urging said staging leaf into alignment with said firing channel.

8. The applicator instrument as claimed in claim 1, wherein said linkage comprises:
    a first rotating link having upper gear teeth and lower gear teeth, said first rotating link being disposed inside an upper portion of said trigger;
    a first pivot pivotally securing said first rotating link to the upper portion of said trigger;
    a second rotating link having upper gear teeth and lower gear teeth, said second rotating link being disposed inside a lower portion of said trigger;
    a second pivot pivotally securing said second rotating link to the lower portion of said trigger;
    the lower gear teeth of said first rotating link meshing with the upper gear teeth of said second rotating link so that when said trigger is squeezed said first and second rotating links rotate at the same rate.

9. The applicator instrument as claimed in claim 8, further comprising a first rack located near the upper end of said handle for meshing with the upper gear teeth of said first rotating link and a second rack located near an upper end of said housing of said applicator instrument for meshing with the lower gear teeth of said second rotating link.

10. The applicator instrument as claimed in claim 1, further comprising a counter located at an upper end of said handle and remote from said housing for indicating the number of surgical fasteners dispensed from or remaining in said applicator instrument.

11. The applicator instrument as claimed in claim 1, wherein said elongated shaft has an articulating section between the proximal section and the distal section thereof.

12. The applicator instrument as claimed in claim 1, wherein said elongated shaft is rotatable relative to said housing.

13. An applicator instrument for dispensing surgical fasteners comprising:
   a housing;
   a firing system disposed in said housing and being moveable in distal and proximal directions along a first axis;
   an elongated shaft extending from said housing, said elongated shaft having a proximal section and a distal section that is oriented at an angle relative to the proximal section;
   a plurality of surgical fasteners disposed in said elongated shaft for being dispensed from a distal end of said elongated shaft;
   a handle extending upwardly from said housing along a second axis that defines an acute angle with said first axis;
   a trigger mounted on said handle;
   a linkage coupling said trigger with said handle and said firing system, wherein when said trigger is squeezed toward said handle, said linkage guides said trigger along a linear path of movement relative to said handle, wherein the linear path of movement of said trigger defines a third axis that forms an acute angle with the first axis and is perpendicular to the second axis.

14. An applicator instrument for dispensing surgical fasteners comprising:
   a housing defining a bottom of said applicator instrument;
   a firing system disposed in said housing and being moveable in distal and proximal directions;
   a handle extending upwardly from said housing and sloping toward a distal end of said applicator instrument, said handle having an upper end that defines a top of said applicator instrument;
   a shaft extending distally from said housing near the bottom of said applicator instrument, said shaft having a proximal section that extends along a longitudinal axis of said applicator instrument and a distal section that is oriented at an angle relative to the proximal section for extending upwardly toward the top of said applicator instrument;
   a plurality of surgical fasteners loaded into said shaft;
   a trigger mounted on said handle for moving along a linear path relative to said handle for actuating said firing system so as to dispense said surgical fasteners from a distal end of said shaft, wherein said handle and said trigger have respective longitudinal axes that are parallel to one another, and wherein the respective longitudinal axes slope toward the distal end of said shaft.

15. The applicator instrument as claimed in claim 14, further comprising a linkage coupling said trigger with said handle and said firing system, wherein when said trigger is squeezed toward said handle, said linkage guides movement of said trigger along the linear path relative to said handle.

16. The applicator instrument as claimed in claim 15, wherein said linkage comprises:
   a first rotating link having upper gear teeth and lower gear teeth, said first rotating link being disposed inside an upper portion of said trigger;
   a first pivot pivotally securing said first rotating link to the upper portion of said trigger;
   a second rotating link having upper gear teeth and lower gear teeth, said second rotating link being disposed inside a lower portion of said trigger;
   a second pivot pivotally securing said second rotating link to the lower portion of said trigger;
   the lower gear teeth of said first rotating link meshing with the upper gear teeth of said second rotating link so that when said trigger is squeezed said first and second rotating links rotate at the same rate for guiding movement of said trigger along the linear path.

17. An applicator instrument for dispensing surgical fasteners comprising:
   a housing defining a bottom of said applicator instrument;
   a firing system disposed in said housing and being moveable in distal and proximal directions;
   a handle extending upwardly from said housing and sloping toward a distal end of said applicator instrument, said handle having an upper end that defines a top of said applicator instrument;
   a shaft extending distally from said housing near the bottom of said applicator instrument, said shaft having a proximal section that extends along a longitudinal axis of said applicator instrument and a distal section that is oriented at an angle relative to the proximal section for extending upwardly toward the top of said applicator instrument;
   a plurality of surgical fasteners loaded into said shaft;
   a trigger mounted on said handle for moving along a linear path relative to said handle for actuating said firing system so as to dispense said surgical fasteners from a distal end of said shaft, further comprising a cap secured to the distal end of said shaft, said cap having a lower distal edge and a distal face that slopes upwardly and proximally from said lower distal edge, said cap including a delivery window formed in said distal face, said delivery window having a lower end that is spaced from said lower distal edge.

18. An applicator instrument comprising:
   a housing defining a bottom of said surgical instrument;
   an elongated shaft extending from said housing along the bottom of said surgical instrument, said elongated shaft having a proximal end secured to said housing and a distal end remote therefrom;
   a plurality of surgical fasteners disposed in said elongated shaft;
   a handle extending upwardly from said housing along an axis that slopes toward the distal end of said elongated shaft, said handle having an upper end that defines a top of said surgical instrument;
   a trigger mounted on said handle for moving relative to said handle along a linear path;
   a linkage coupling said trigger with said handle for guiding movement of said trigger along the linear path relative to said handle, wherein said linkage comprises
   a first rotating link having upper gear teeth and lower gear teeth, said first rotating link being disposed inside an upper portion of said trigger;
   a first pivot pivotally securing said first rotating link to the upper portion of said trigger;
   a second rotating link having upper gear teeth and lower gear teeth, said second rotating link being disposed inside a lower portion of said trigger;

a second pivot pivotally securing said second rotating link to the lower portion of said trigger; and the lower gear teeth of said first rotating link meshing with the upper gear teeth of said second rotating link, wherein when said trigger is squeezed toward said trigger, said first and second rotating links rotate at the same rate for moving said trigger along the linear path relative to said handle.

\* \* \* \* \*